US011223018B2

United States Patent
Kim et al.

(10) Patent No.: US 11,223,018 B2
(45) Date of Patent: *Jan. 11, 2022

(54) CONDENSED CYCLIC COMPOUND AND ORGANIC LIGHT-EMITTING DEVICE INCLUDING THE SAME

(71) Applicant: SAMSUNG DISPLAY CO., LTD., Yongin-si (KR)

(72) Inventors: Sooyon Kim, Yongin-si (KR); Youngkook Kim, Yongin-si (KR); Jongwoo Kim, Yongin-si (KR); Jeonga Oh, Yongin-si (KR); Hyejin Jung, Yongin-si (KR); Seokhwan Hwang, Yongin-si (KR); Jaeyong Lee, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 551 days.

This patent is subject to a terminal disclaimer.

(21) Appl. No.: 15/167,813

(22) Filed: May 27, 2016

(65) Prior Publication Data

US 2017/0125688 A1    May 4, 2017

(30) Foreign Application Priority Data

Nov. 3, 2015    (KR) .................. 10-2015-0153802

(51) Int. Cl.
*H01L 51/00* (2006.01)
*C07D 405/14* (2006.01)
(Continued)

(52) U.S. Cl.
CPC ........ *H01L 51/0061* (2013.01); *C07D 221/18* (2013.01); *C07D 401/12* (2013.01);
(Continued)

(58) Field of Classification Search
CPC ... H01L 51/5056–5064; H01L 51/0059–0061; C07D 219/00–16
See application file for complete search history.

(56) References Cited

U.S. PATENT DOCUMENTS 6,465,115 B2   10/2002   Shi et al.
6,596,415 B2    7/2003   Shi et al.
(Continued)

FOREIGN PATENT DOCUMENTS

CN    103589420 A   *   2/2014
JP    2006-151930 A       6/2006
(Continued)

OTHER PUBLICATIONS

Machine Translation of CN-103589420-A.*
Machine translation of WO-2015122711-A1.*

*Primary Examiner* — William E McClain
(74) *Attorney, Agent, or Firm* — Lewis Roca Rothgerber Christie LLP

(57) ABSTRACT

An organic light-emitting device includes: a first electrode; a second electrode facing the first electrode; and an organic layer between the first electrode and the second electrode, the organic layer including an emission layer, wherein the organic layer includes a condensed cyclic compound of Formula 1:

(Continued)

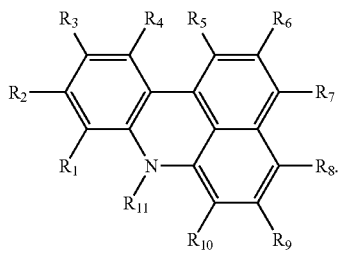

Formula 1

An organic light-emitting device including the condensed cyclic compound of Formula 1 may have high efficiency, low driving voltage, high luminance, and a long lifespan.

13 Claims, 1 Drawing Sheet

(51) Int. Cl.
  *C07D 401/12* (2006.01)
  *C07D 221/18* (2006.01)
  *C07D 409/14* (2006.01)
  *H01L 51/50* (2006.01)

(52) U.S. Cl.
  CPC ......... *C07D 405/14* (2013.01); *C07D 409/14* (2013.01); *H01L 51/006* (2013.01); *H01L 51/0052* (2013.01); *H01L 51/0072* (2013.01); *H01L 51/0073* (2013.01); *H01L 51/0074* (2013.01); *H01L 51/0056* (2013.01); *H01L 51/5056* (2013.01); *H01L 51/5088* (2013.01); *H01L 51/5096* (2013.01)

(56) References Cited

U.S. PATENT DOCUMENTS

| | | | |
|---|---|---|---|
| 9,842,995 B2* | 12/2017 | Jung | H01L 51/0061 |
| 10,600,969 B2 | 3/2020 | Mun et al. | |
| 2005/0221124 A1 | 10/2005 | Hwang et al. | |
| 2008/0169755 A1* | 7/2008 | Kim | C07D 403/12 313/504 |
| 2009/0004485 A1 | 1/2009 | Zheng et al. | |
| 2010/0001636 A1 | 1/2010 | Yabunouchi | |
| 2012/0248426 A1 | 10/2012 | Kato | |
| 2013/0306958 A1 | 11/2013 | Ito et al. | |
| 2014/0155592 A1* | 6/2014 | Takada | H01L 51/0061 544/38 |
| 2015/0048323 A1 | 2/2015 | Kim et al. | |
| 2015/0280139 A1* | 10/2015 | Ichihashi | C07D 213/74 257/40 |
| 2016/0149141 A1* | 5/2016 | Jung | H01L 51/006 257/40 |
| 2017/0092869 A1* | 3/2017 | Mun | C07D 333/76 |
| 2017/0141311 A1* | 5/2017 | Lee | C07D 401/10 |

FOREIGN PATENT DOCUMENTS

| | | | | |
|---|---|---|---|---|
| JP | 2007-123863 A | 5/2007 | | |
| KR | 10-2005-0097670 A | 10/2005 | | |
| KR | 10-2011-0011647 A | 2/2011 | | |
| KR | 10-2012-0066076 A | 6/2012 | | |
| KR | 10-2012-0081539 A | 7/2012 | | |
| KR | 10-2014-0032948 A | 3/2014 | | |
| KR | 10-2015-0019391 A | 2/2015 | | |
| KR | 10-1512058 B1 | 4/2015 | | |
| WO | WO 2012/157474 A1 | 11/2012 | | |
| WO | WO-2015122711 A1 * | 8/2015 | ......... | H01L 51/0067 |
| WO | WO 2016/003202 A2 | 1/2016 | | |

* cited by examiner

10

| 190 |
|---|
| 150 |
| 110 |

CONDENSED CYCLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2015-0153802, filed on Nov. 3, 2015, in the Korean Intellectual Property Office, the entire content of which is incorporated herein by reference.

BACKGROUND

1. Field

One or more aspects of embodiments of the present disclosure relate to a compound for an organic light-emitting device, and an organic light-emitting device including the same.

2. Description of the Related Art

Organic light-emitting devices are self-emission devices that have wide viewing angles, high contrast ratios, short response times, and excellent brightness, driving voltage, and/or response speed characteristics, and can produce full-color images.

An organic light-emitting device may include a first electrode disposed (e.g., positioned) on a substrate, and a hole transport region, an emission layer, an electron transport region, and a second electrode, which are sequentially disposed on the first electrode. Holes provided from the first electrode, for example, may move toward the emission layer through the hole transport region, and electrons provided from the second electrode, for example, may move toward the emission layer through the electron transport region. Carriers, such as holes and electrons, can then recombine in the emission layer to produce excitons. These excitons transition from an excited state to a ground state, thereby generating light.

SUMMARY

One or more aspects of embodiments of the present disclosure are directed toward a condensed cyclic compound having a novel structure and an organic light-emitting device including the condensed cyclic compound.

Additional aspects will be set forth in part in the description which follows and, in part, will be apparent from the description, or may be learned by practice of the presented embodiments.

According to one or more embodiments, a condensed cyclic compound is represented by Formula 1:

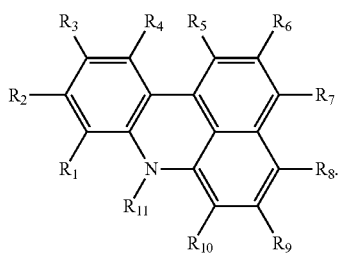

Formula 1

In Formula 1, $R_1$ to $R_{11}$ may each independently be selected from a group represented by Formula 2, hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$), provided that $R_{11}$ is not the group represented by Formula 2, and a substituent selected from $R_1$ to $R_{10}$ may be represented by Formula 2:

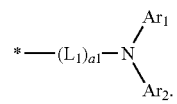

Formula 2

In Formula 2, $L_1$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a1 may be an integer selected from 0 to 3, wherein when a1 is two or more, two or more $L_1$(s) may be identical to or different from each other;

$Ar_1$ and $Ar_2$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, provided that at least one selected from $Ar_1$ and $Ar_2$ may each independently be selected from a substituted or unsubstituted fluorenyl group, a substituted or unsubstituted spiro-bifluorenyl group, a substituted or unsubstituted carbazolyl group, a substituted or unsubstituted dibenzofuranyl group, a substituted or unsubstituted dibenzothiophenyl group, and a substituted or unsubstituted dibenzosilolyl group.

At least one substituent of the substituted fluorenyl group, substituted spiro-bifluorenyl group, a substituted carbazolyl group, a substituted dibenzofuranyl group, a substituted dibenzothiophenyl group, a substituted dibenzosilolyl group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, a substituted divalent non-aromatic condensed polycyclic group, a substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from the group consisting of:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, $C_6$-$C_{60}$ arylthio group, $C_1$-$C_{60}$ heteroaryl group, a monovalent non-aromatic condensed polycyclic group, a monovalent non-aromatic condensed heteropolycyclic group, and —Si($Q_{11}$)($Q_{12}$)($Q_{13}$), a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, and —Si($Q_{21}$)($Q_{22}$)($Q_{23}$), and —Si($Q_{31}$)($Q_{32}$)($Q_{33}$), wherein $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

According to one or more embodiments, an organic light-emitting device includes a first electrode; a second electrode facing the first electrode; and an organic layer between the first electrode and the second electrode, the organic layer including an emission layer, wherein the organic layer includes the condensed cyclic compound as described above.

BRIEF DESCRIPTION OF THE DRAWING

These and/or other aspects will become apparent and more readily appreciated from the following description of the embodiments, taken in conjunction with the drawing, which is a schematic diagram of a structure of an organic light-emitting device according to an embodiment of the present disclosure.

DETAILED DESCRIPTION

Reference will now be made in more detail to embodiments, examples of which are illustrated in the accompanying drawing, wherein like reference numerals refer to like elements throughout. In this regard, the present embodiments may have different forms and should not be construed as being limited to the descriptions set forth herein. Accordingly, the embodiments are merely described below, by referring to the drawing, to explain aspects of the present description. As used herein, the term "and/or" includes any and all combinations of one or more of the associated listed items. Expressions such as "at least one of," "one of," and "selected from," when preceding a list of elements, modify the entire list of elements and do not modify the individual elements of the list. Further, the use of "may" when describing embodiments of the present invention refers to "one or more embodiments of the present invention."

A condensed cyclic compound according to embodiments of the present disclosure is represented by Formula 1:

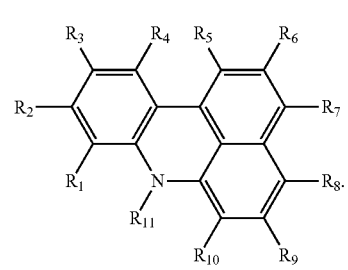

Formula 1

R$_1$ to R$_{11}$ in Formula 1 may each independently be selected from a group represented by Formula 2, hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, a substituted or unsubstituted monovalent non-aromatic condensed heteropolycyclic group, and —Si(Q$_1$)(Q$_2$)(Q$_3$), provided that R$_{11}$ is not the group represented by Formula 2.

A substituent selected from R$_1$ to R$_{10}$ in Formula 1 may be the group represented by Formula 2.

Formula 2

In Formula 2,

L$_1$ may be selected from a substituted or unsubstituted C$_3$-C$_{10}$ cycloalkylene group, a substituted or unsubstituted C$_1$-C$_{10}$ heterocycloalkylene group, a substituted or unsubstituted C$_3$-C$_{10}$ cycloalkenylene group, a substituted or unsubstituted C$_1$-C$_{10}$ heterocycloalkenylene group, a substituted or unsubstituted C$_6$-C$_{60}$ arylene group, a substituted or unsubstituted C$_1$-C$_{60}$ heteroarylene group, a substituted or unsubstituted divalent non-aromatic condensed polycyclic group, and a substituted or unsubstituted divalent non-aromatic condensed heteropolycyclic group.

For example, L$_1$ in Formula 2 may be selected from the group consisting of:

a phenylene group, a pentalenylene group, an indenylene group, a naphthylene group, an azulenylene group, a heptalenylene group, an indacenylene group, an acenaphthylene group, a fluorenylene group, spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a benzocarbazolylene group, a dibenzocarbazolylene group, a thiadiazolylene group, an imidazopyridinylene group, and an imidazopyrimidinylene group, and a phenylene group, a pentalenylene group, an indenylene group, a naphthylene group, an azulenylene group, a heptalenylene group, an indacenylene group, an acenaphthylene group, a fluorenylene group, spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolylene group, a benzocarbazolyl group, a dibenzocarbazolyl group, a thiadiazolyl group, an imidazopyridinyl group, and an imidazopyrimidinyl group.

In various embodiments, $L_1$ in Formula 2 may be selected from groups represented by Formula 3-1 to Formula 3-42:

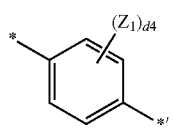

Formula 3-1

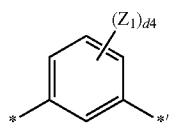

Formula 3-2

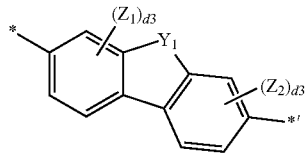

Formula 3-3

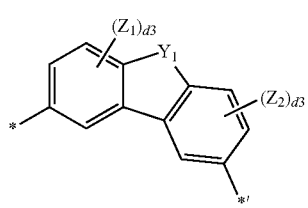

Formula 3-4

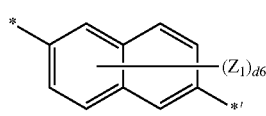

Formula 3-5

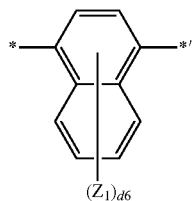

Formula 3-6

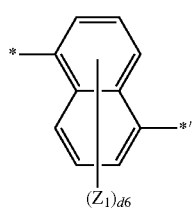

Formula 3-7

-continued

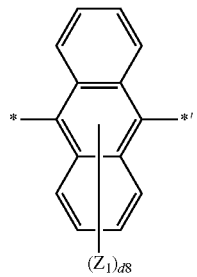

Formula 3-8

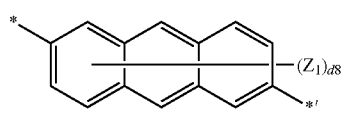

Formula 3-9

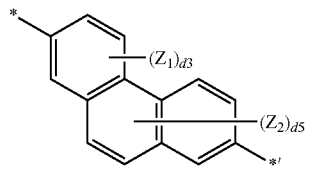

Formula 3-10

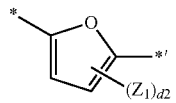

Formula 3-11

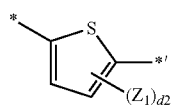

Formula 3-12

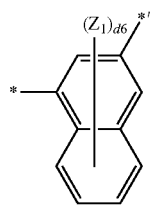

Formula 3-13

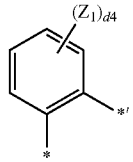

Formula 3-14

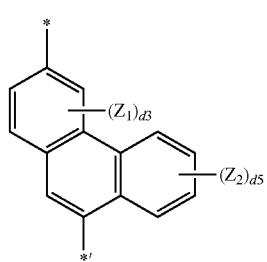

Formula 3-15

-continued
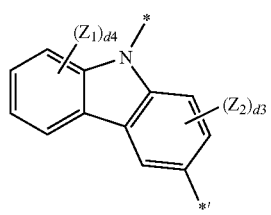
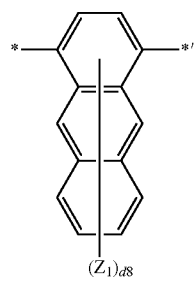
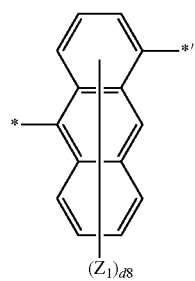
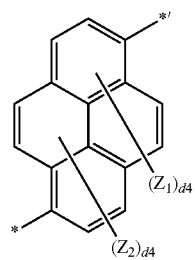
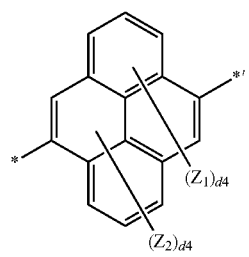
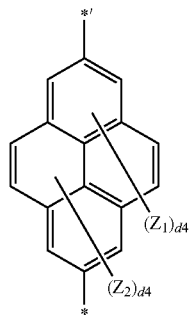
Formula 3-16
Formula 3-17
Formula 3-18
Formula 3-19
Formula 3-20
Formula 3-21
-continued
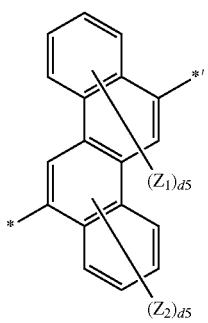
Formula 3-22
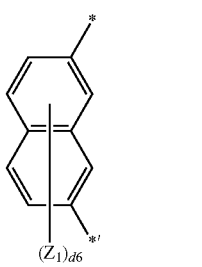
Formula 3-23
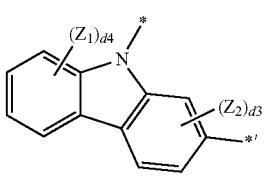
Formula 3-24
Formula 3-25
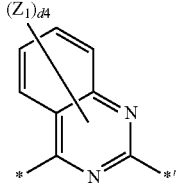
Formula 3-26
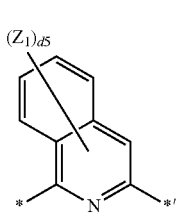
Formula 3-27
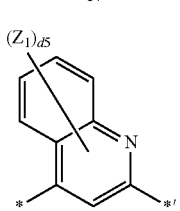
Formula 3-28
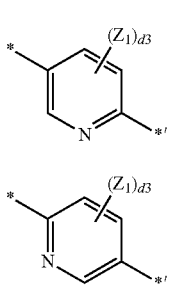
Formula 3-29

-continued

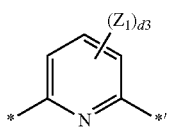
Formula 3-30

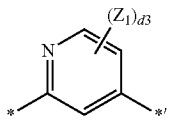
Formula 3-31

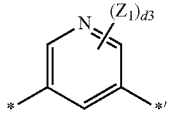
Formula 3-32

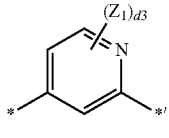
Formula 3-33

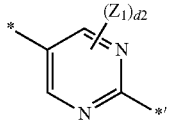
Formula 3-34

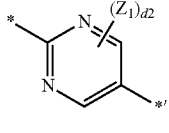
Formula 3-35

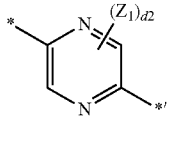
Formula 3-36

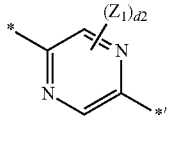
Formula 3-37

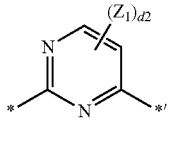
Formula 3-38

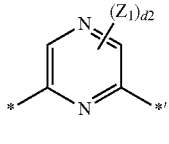
Formula 3-39

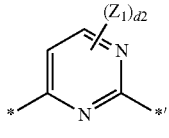
Formula 3-40

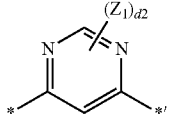
Formula 3-41

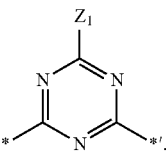
Formula 3-42

In Formulae 3-1 to 3-42, $Y_1$ may be selected from O, S, $C(Z_3)(Z_4)$, $N(Z_5)$, and $Si(Z_6)(Z_7)$;

$Z_1$ to $Z_7$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —$Si(Q_{31})(Q_{32})(Q_{33})$;

$Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group;

d2 may be 1 or 2;
d3 may be an integer selected from 1 to 3;
d4 may be an integer selected from 1 to 4;
d5 may be an integer selected from 1 to 5;
d6 may be an integer selected from 1 to 6;
d8 may be an integer selected from 1 to 8; and
* and *' each indicate a binding site to a neighboring atom.

In various embodiments, $L_1$ in Formula 2 may be selected from the group consisting of:

a phenylene group, a naphthylene group, a fluorenylene group, a phenanthrenylene group, an anthracenylene group, a triphenylenylene group, and a pyrenylene group, and a phenylene group, a naphthylene group, a fluorenylene group, a phenanthrenylene group, an anthracenylene group, a triphenylenylene group, and a pyrenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, and a naphthyl group, but $L_1$ is not limited thereto.

In various embodiments, $L_1$ in Formula 2 may be selected from groups represented by Formula 4-1 to Formula 4-29, but is not limited thereto:

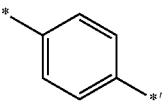
Formula 4-1

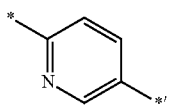
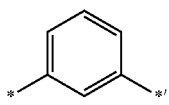
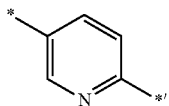
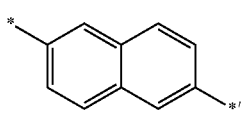
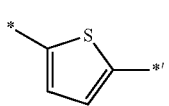
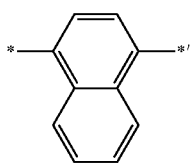
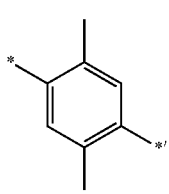
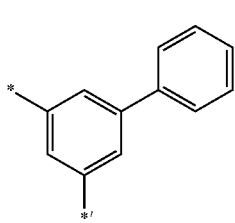
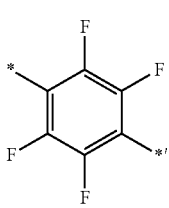
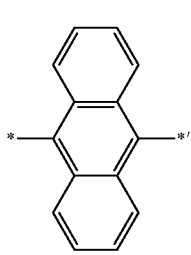
Formula 4-2
Formula 4-3
Formula 4-4
Formula 4-5
Formula 4-6
Formula 4-7
Formula 4-8
Formula 4-9
Formula 4-10
Formula 4-11
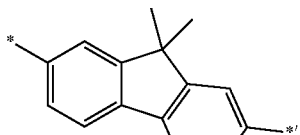
Formula 4-12
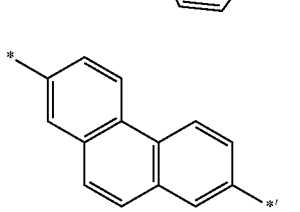
Formula 4-13
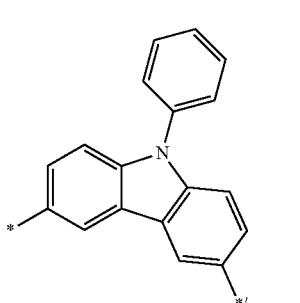
Formula 4-14
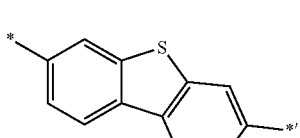
Formula 4-15
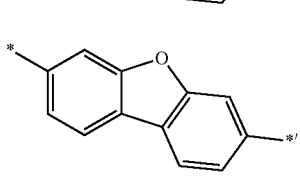
Formula 4-16
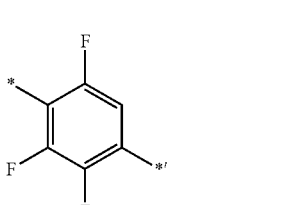
Formula 4-17
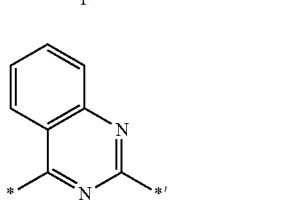
Formula 4-18
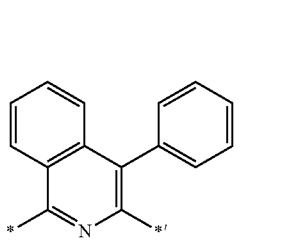
Formula 4-19

-continued

Formula 4-20
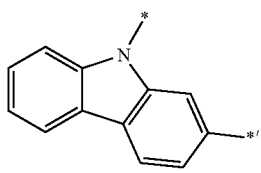

Formula 4-21
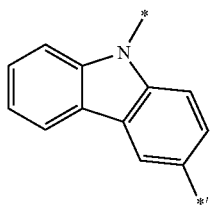

Formula 4-22
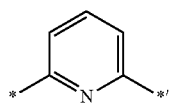

Formula 4-23
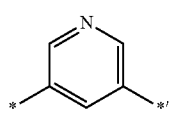

Formula 4-24
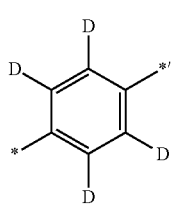

Formula 4-25
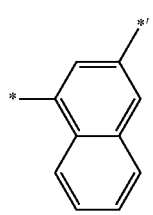

Formula 4-26
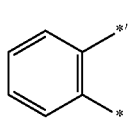

Formula 4-27
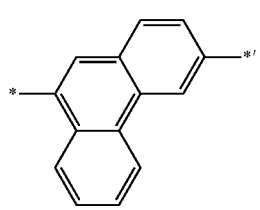

Formula 4-28
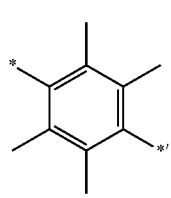

Formula 4-29
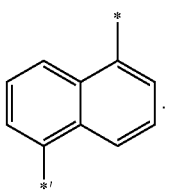

* and *' in Formulae 4-1 to 4-29 each indicate a binding site to a neighboring atom, and "D" may refer to deuterium.

a1 in Formula 2 may be an integer selected from 0 to 3. a1 indicates the number of $L_1$(s) in Formula 2, and when a1 is two or more, two or more $L_1$(s) may be identical to or different from each other. For example, when a1 is 0, *-$(L_1)_{a1}$-*' indicates a single bond. In various embodiments, a1 may be 0, 1, or 2. For example, a1 may be 0 or 1.

$Ar_1$ and $Ar_2$ in Formula 2 may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, provided that at least one selected from $Ar_1$ and $Ar_2$ may each independently be selected from a substituted or unsubstituted fluorenyl group, a substituted or unsubstituted spiro-bifluorenyl group, a substituted or unsubstituted carbazolyl group, a substituted or unsubstituted dibenzofuranyl group, a substituted or unsubstituted dibenzothiophenyl group, and a substituted or unsubstituted dibenzosilolyl group.

For example, $Ar_1$ and $Ar_2$ in Formula 2 may each independently be selected from:

a substituted or unsubstituted phenyl group, a substituted or unsubstituted biphenyl group, a substituted or unsubstituted terphenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted spiro-bifluorenyl group, a substituted or unsubstituted benzofluorenyl group, a substituted or unsubstituted dibenzofluorenyl group, a substituted or unsubstituted phenalenyl group, a substituted or unsubstituted phenanthrenyl group, a substituted or unsubstituted anthracenyl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pentacenyl group, a substituted or unsubstituted rubicenyl group, a substituted or unsubstituted coronenyl group, a substituted or unsubstituted ovalenyl group, a substituted or unsubstituted pyrrolyl group, a substituted or unsubstituted thiophenyl group, a substituted or unsubstituted furanyl group, a substituted or unsubstituted imidazolyl group, a substituted or unsubstituted pyrazolyl group, a substituted or unsubstituted thiazolyl group, a substituted or unsubstituted isothiazolyl group, a substituted or unsubstituted oxazolyl group, a substituted or unsubstituted isoxazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted isoquinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzoimidazolyl group, a substituted or unsubstituted benzofuranyl group, a substituted or unsubstituted dibenzofuranyl group, a substituted or unsubstituted benzothiophenyl group, a substituted or unsubstituted dibenzothiophenyl group, a substituted or unsubstituted isobenzothiazolyl group, a substituted or unsubstituted benzoxazolyl group, a substituted or unsubstituted isobenzoxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted benzocarbazolyl group, a substituted or unsubstituted dibenzocarbazolyl group, a substituted or unsubstituted thiadiazolyl group, a substituted or unsubstituted imidazopyridinyl group, and a substituted or unsubstituted imidazopyrimidinyl group, where at least one substituent of the substituted phenyl group, the substituted biphenyl group, the substituted terphenyl group, the substituted pentalenyl group, the substituted indenyl group, the substituted naphthyl group, the substituted azulenyl group, the substituted heptalenyl group, the substituted indacenyl group, the substituted acenaphthyl group, the substituted fluorenyl group, substituted spiro-bifluorenyl group, the substituted benzofluorenyl group, the substituted dibenzofluorenyl group, the substituted phenalenyl group, the substituted phenanthrenyl group, the substituted anthracenyl group, the substituted fluoranthenyl group, the substituted triphenylenyl group, the substituted pyrenyl group, the substituted chrysenyl group, the substituted naphthacenyl group, the substituted picenyl group, the substituted perylenyl group, the substituted pentaphenyl group, the substituted hexacenyl group, the substituted pentacenyl group, the substituted rubicenyl group, the substituted coronenyl group, the substituted ovalenyl group, the substituted pyrrolyl group, the substituted thiophenyl group, the substituted furanyl group, the substituted imidazolyl group, the substituted pyrazolyl group, the substituted thiazolyl group, the substituted isothiazolyl group, the substituted oxazolyl group, the substituted isoxazolyl group, the substituted pyridinyl group, the substituted pyrazinyl group, the substituted pyrimidinyl group, the substituted pyridazinyl group, the substituted isoindolyl group, the substituted indolyl group, the substituted indazolyl group, the substituted purinyl group, a substituted quinolinyl group, the substituted isoquinolinyl group, the substituted benzoquinolinyl group, the substituted phthalazinyl group, the substituted naphthyridinyl group, the substituted quinoxalinyl group, the substituted quinazolinyl group, the substituted cinnolinyl group, the substituted carbazolyl group, the substituted phenanthridinyl group, the substituted acridinyl group, the substituted phenanthrolinyl group, the substituted phenazinyl group, the substituted benzoimidazolyl group, the substituted benzofuranyl group, the substituted dibenzofuranyl group, the substituted benzothiophenyl group, the substituted dibenzothiophenyl group, the substituted isobenzothiazolyl group, the substituted benzoxazolyl group, the substituted isobenzoxazolyl group, the substituted triazolyl group, the substituted tetrazolyl group, the substituted oxadiazolyl group, the substituted triazinyl group, the substituted benzocarbazolyl group, the substituted dibenzocarbazolyl group, the substituted thiadiazolyl group, the substituted imidazopyridinyl group, and the substituted imidazopyrimidinyl group may be selected from the group consisting of:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group, a phenyl group, a biphenyl group, a terphenyl group, a naphthyl group, a pyridinyl group, a fluorenyl group, spiro-bifluorenyl group, a benzofluorenyl group, a dibenzofluorenyl group, a phenanthrenyl group, an anthracenyl group, a pyrenyl group, a chrysenyl group, a carbazolyl group, a benzocarbazolyl group and a dibenzocarbazolyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group and a pyridinyl group, and —Si($Q_{31}$)($Q_{32}$)($Q_{33}$), wherein $Q_{31}$ to $Q_{33}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a pyrenyl group, a chrysenyl group, and a carbazolyl group.

In various embodiments, $Ar_1$ and $Ar_2$ in Formula 2 may each independently be selected from groups represented by Formula 5-1 to Formula 5-18, provided that at least one selected from Ar₁ and Ar₂ may each independently be selected from groups represented by Formulae 5-14 to 5-18:

Formula 5-1
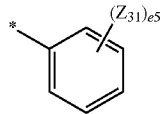

Formula 5-2
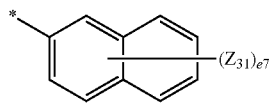

Formula 5-3
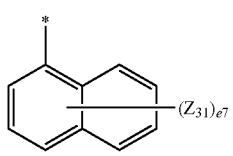

Formula 5-4
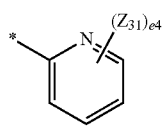

Formula 5-5
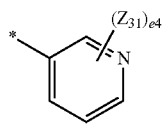

Formula 5-6
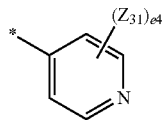

Formula 5-7
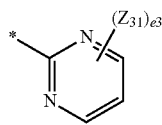

Formula 5-8
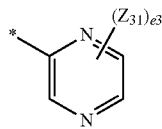

Formula 5-9
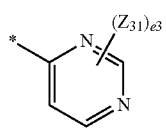

Formula 5-10
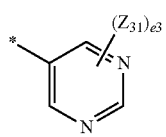

Formula 5-11
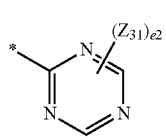

-continued

Formula 5-12
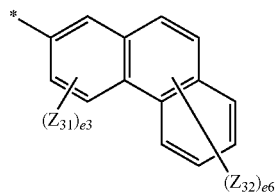

Formula 5-13
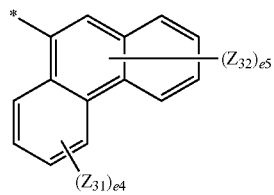

Formula 5-14
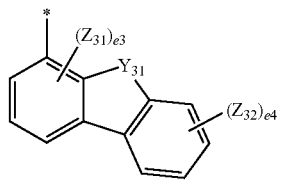

Formula 5-15
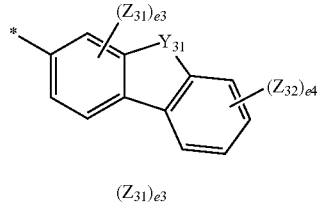

Formula 5-16
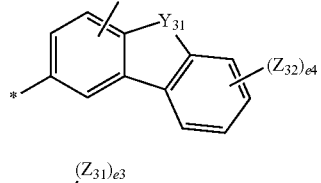

Formula 5-17
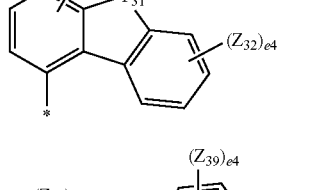

Formula 5-18
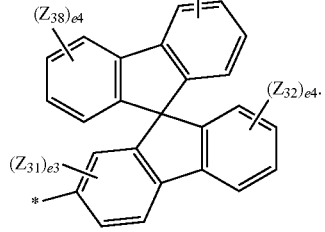

In Formulae 5-1 to 5-18, $Y_{31}$ may be selected from O, S, $C(Z_{33})(Z_{34})$, $N(Z_{35})$, and $Si(Z_{36})(Z_{37})$;

$Z_{31}$ to $Z_{39}$ may each independently be selected from the group consisting of:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a pyrenyl group, a chrysenyl group, a carbazolyl group, a benzocarbazolyl group and a dibenzocarbazolyl group, a phenyl group, a biphenyl group, a terphenyl group, a naphthyl group, a pyridinyl group, a fluorenyl group, spiro-bifluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, and a pyridinyl group, and —Si($Q_{31}$)($Q_{32}$)($Q_{33}$), wherein $Q_{31}$ to $Q_{33}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a pyrenyl group, a chrysenyl group, and a carbazolyl group;

e2 may be 1 or 2;
e3 may be an integer selected from 1 to 3;
e4 may be an integer selected from 1 to 4;
e5 may be an integer selected from 1 to 5;
e6 may be an integer selected from 1 to 6;
e7 may be an integer selected from 1 to 7; and
* indicates a binding site to a neighboring atom.

In various embodiments, $Ar_1$ and $Ar_2$ in Formula 2 may each independently be selected from groups represented by Formula 6-1 to Formula 6-42, provided that at least one selected from $Ar_1$ and $Ar_2$ may each independently be selected from groups represented by Formula 6-25 to Formula 6-42:

Formula 6-1

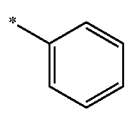

Formula 6-2

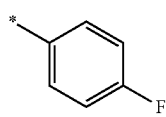

Formula 6-3

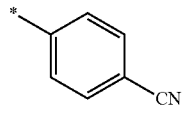

Formula 6-4

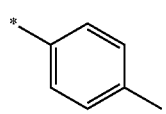

Formula 6-5

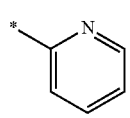

Formula 6-6

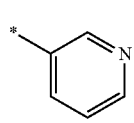

Formula 6-7

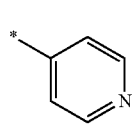

Formula 6-8

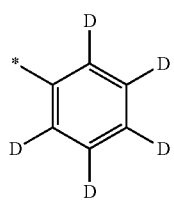

Formula 6-9

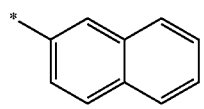

Formula 6-10

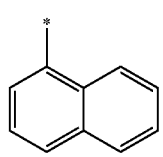

Formula 6-11

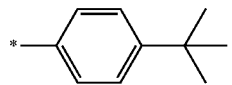

Formula 6-12

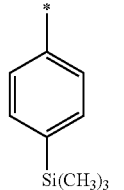

Formula 6-13

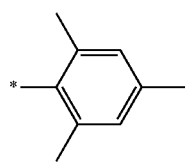

Formula 6-14
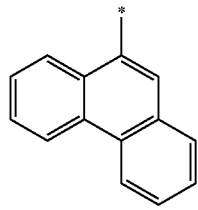
Formula 6-15
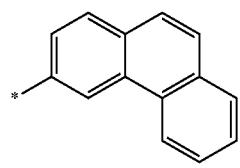
Formula 6-16
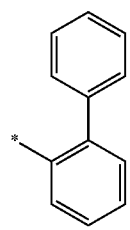
Formula 6-17
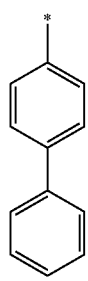
Formula 6-18
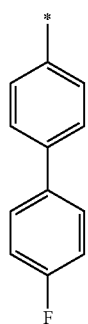
Formula 6-19
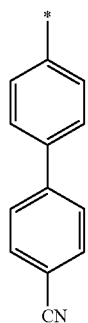
Formula 6-20
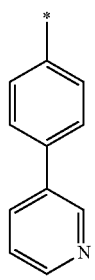
Formula 6-21
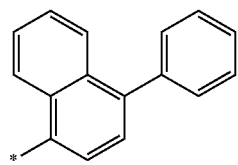
Formula 6-22
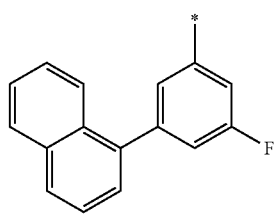
Formula 6-23
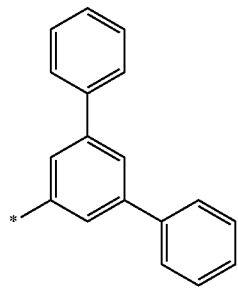
Formula 6-24
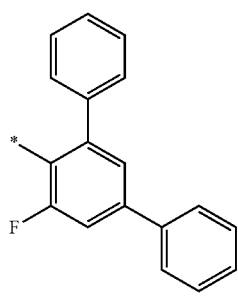
Formula 6-25
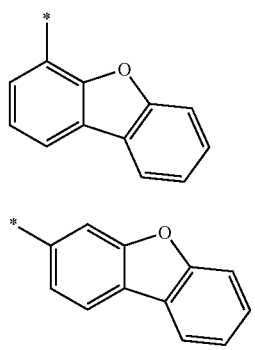
Formula 6-26

Formula 6-27
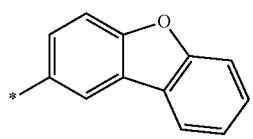
Formula 6-28
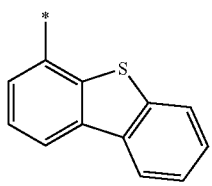
Formula 6-29
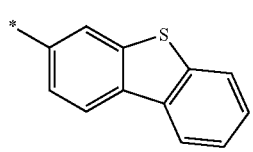
Formula 6-30
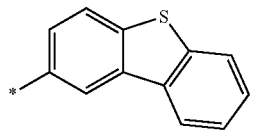
Formula 6-31
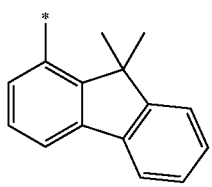
Formula 6-32
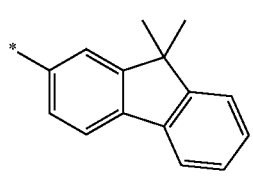
Formula 6-33
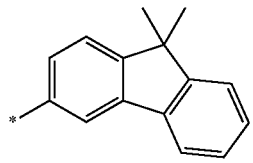
Formula 6-34
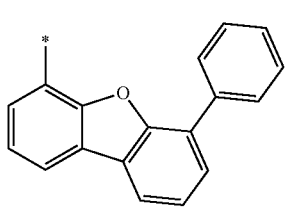
Formula 6-35
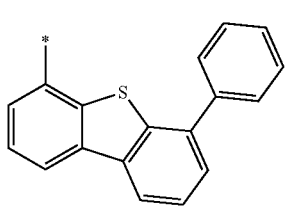
Formula 6-36
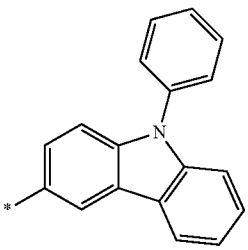
Formula 6-37
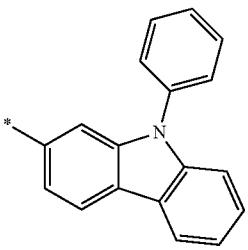
Formula 6-38
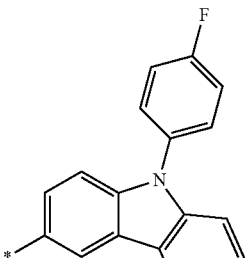
Formula 6-39
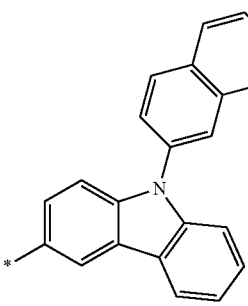
Formula 6-40
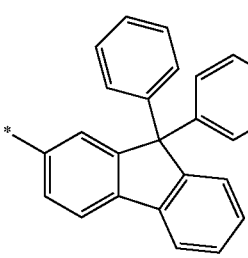
Formula 6-41
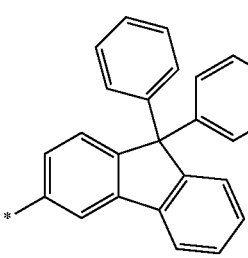

-continued

Formula 6-42

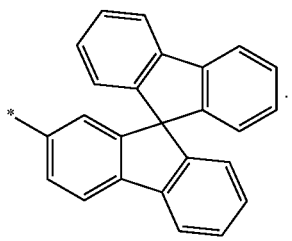

* in Formulae 6-1 to 6-42 indicates a binding site to a neighboring atom, and "D" may refer to deuterium.

$R_1$ to $R_{10}$ in Formula 1 may each independently be selected from the group consisting of:

the group represented by Formula 2, hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, a dibenzosilolyl group, an imidazopyridinyl group, and an imidazopyrimidinyl group, a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, a dibenzosilolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, a dibenzosilolyl group, an imidazopyridinyl group, an imidazopyrimidinyl group, and —Si($Q_{31}$)($Q_{32}$)($Q_{33}$), and
—Si($Q_1$)($Q_2$)($Q_3$), wherein $Q_1$ to $Q_3$ and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but $R_1$ to $R_{10}$ are not limited thereto.

In various embodiments, $R_1$ to $R_{10}$ may each independently be selected from the group consisting of:

the group represented by Formula 2, hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, a phenyl group, a biphenyl group, a terphenyl group, a naphthyl group, a pyridinyl group, a pyrimidinyl group, and a triazinyl group, a phenyl group, a biphenyl group, a terphenyl group, a naphthyl group, a pyridinyl group, a pyrimidinyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a triazinyl group, and —Si($Q_{31}$)($Q_{32}$)($Q_{33}$), and
—Si($Q_1$)($Q_2$)($Q_3$), wherein $Q_1$ to $Q_3$ and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but $R_1$ to $R_{10}$ are not limited thereto.

In various embodiments, $R_{11}$ may be selected from the group consisting of:

a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, a dibenzosilolyl group, an imidazopyridinyl group, and an imidazopyrimidinyl group, and a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, a dibenzosilolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, a dibenzosilolyl group, an imidazopyridinyl group, an imidazopyrimidinyl group, and —$Si(Q_{31})(Q_{32})(Q_{33})$, where $Q_{31}$ to $Q_{33}$ are as defined above, but $R_{11}$ is not limited thereto.

A substituent selected from $R_1$ to $R_{10}$ in Formula 1 may be the group represented by Formula 2.

In various embodiments, $R_2$ or $R_7$ in Formula 1 may be the group represented by Formula 2.

In various embodiments, the condensed cyclic compound represented by Formula 1 may be represented by one of Formulae 1-1(A), 1-1(B), 1-2(A), and 1-2(B), but is not limited thereto:

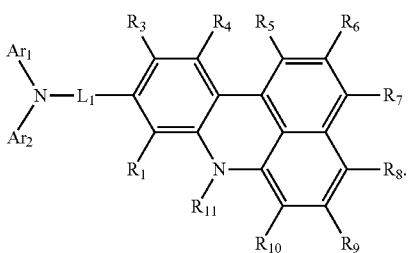

Formula 1-1(A)

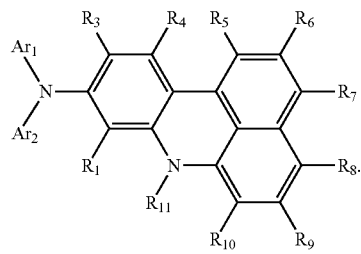

Formula 1-1(B)

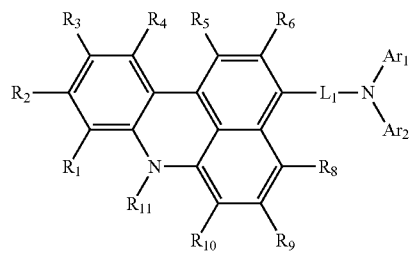

Formula 1-2(A)

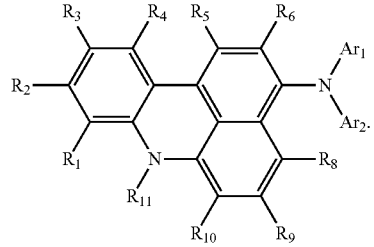

Formula 1-2(B)

$L_1$, $Ar_1$, $Ar_2$, and $R_1$ to $R_{11}$ in the Formulae 1-1(A), 1-1(B), 1-2(A), and 1-2(B) are the same as described above.

In various embodiments, in the Formulae 1-1(A), 1-1(B), 1-2(A), and 1-2(B) above, $R_1$ to $R_{10}$ may each be hydrogen;

$L_1$ may be selected from a substituted or unsubstituted phenylene group, a substituted or unsubstituted naphthylene group, a substituted or unsubstituted fluorenylene group, a substituted or unsubstituted phenanthrenylene group, a substituted or unsubstituted anthracenylene group, a substituted or unsubstituted triphenylenylene group, and a substituted or unsubstituted pyrenylene group;

$R_{11}$, $Ar_1$, and $Ar_2$ may each independently be selected from a substituted or unsubstituted phenyl group, a substituted or unsubstituted biphenyl group, a substituted or unsubstituted terphenyl group, a substituted or unsubstituted naphthyl group, a substituted or unsubstituted fluorenyl group, a substituted or unsubstituted phenanthrenyl group, a substituted or unsubstituted anthracenyl group, a substituted or unsubstituted triphenylenyl group, a substituted or unsubstituted pyrenyl group, a substituted or unsubstituted fluorenyl group, a substituted or unsubstituted spiro-bifluorenyl group, a substituted or unsubstituted carbazolyl group, a substituted or unsubstituted dibenzofuranyl group, a substituted or unsubstituted dibenzothiophenyl group, and a substituted or unsubstituted dibenzosilolyl group, provided that at least one selected from $Ar_1$ and $Ar_2$ may each independently be selected from a substituted or unsubstituted fluorenyl group, a substituted or unsubstituted spiro-bifluorenyl group, a substituted or unsubstituted carbazolyl group, a substituted or unsubstituted dibenzofuranyl group, a substituted or unsubstituted dibenzothiophenyl group, and a substituted or unsubstituted dibenzosilolyl group; and at least one substituent of the substituted phenylene group, substituted naphthylene group, substituted fluorenylene group, substituted phenanthrenylene group, substituted anthracenylene group, substituted triphenylenylene group, substituted pyrenylene group, substituted phenyl group, substituted biphenyl group, substituted terphenyl group, substituted naphthyl group, substituted fluorenyl group, substituted phenanthrenyl group, substituted anthracenyl group, substituted triphenylenyl group, substituted pyrenyl group, substituted fluorenyl group, substituted spiro-bifluorenyl group, substituted carbazolyl group, substituted dibenzofuranyl group, substituted dibenzothiophenyl group, and a substituted dibenzosilolyl group may be selected from the group consisting of:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group, a phenyl group, a biphenyl group, a terphenyl group, a naphthyl group, a pyridinyl group, a fluorenyl group, spiro-bifluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, and a pyridinyl group, and —Si($Q_{31}$)($Q_{32}$)($Q_{33}$), wherein $Q_{31}$ to $Q_{33}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a pyrenyl group, a chrysenyl group, and a carbazolyl group, but embodiments of the present disclosure are not limited thereto.

For example, the condensed cyclic compound represented by Formula 1 may be one of Compounds 1 to 96, but is not limited thereto:

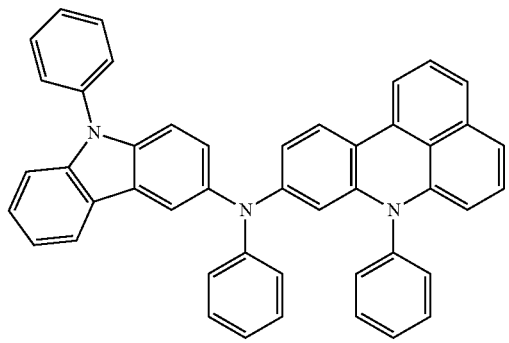

1

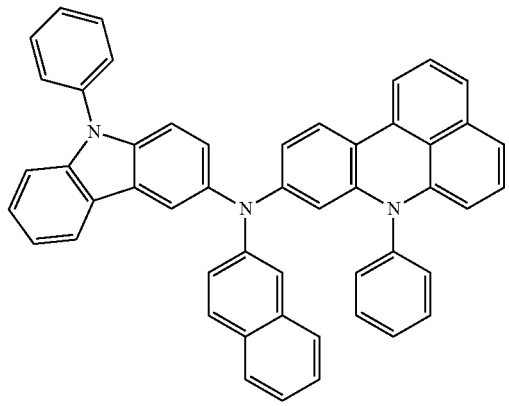

2

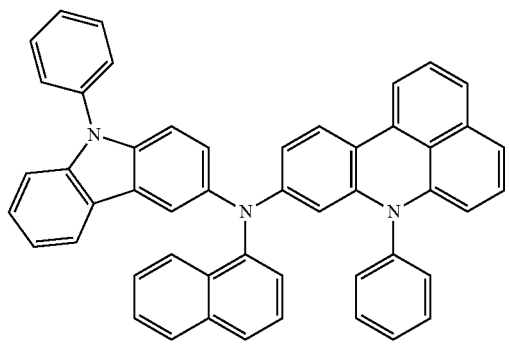

3

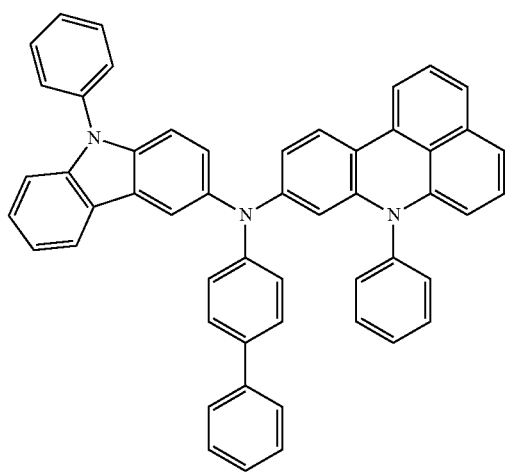

4

US 11,223,018 B2
33
-continued
5
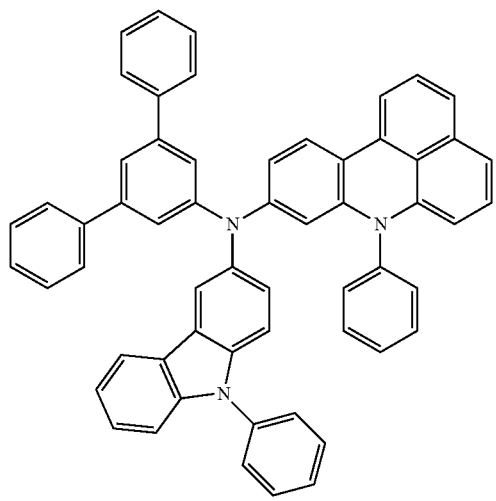
6
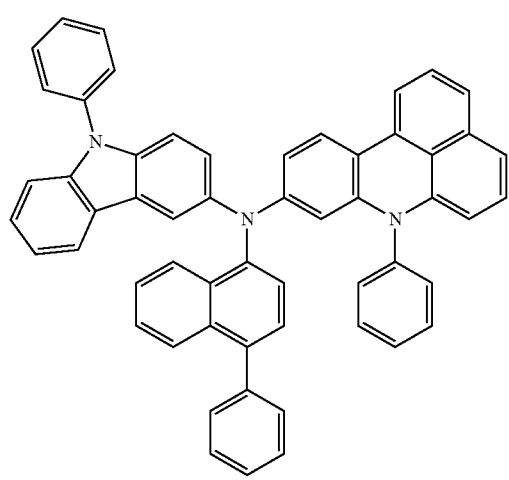
7
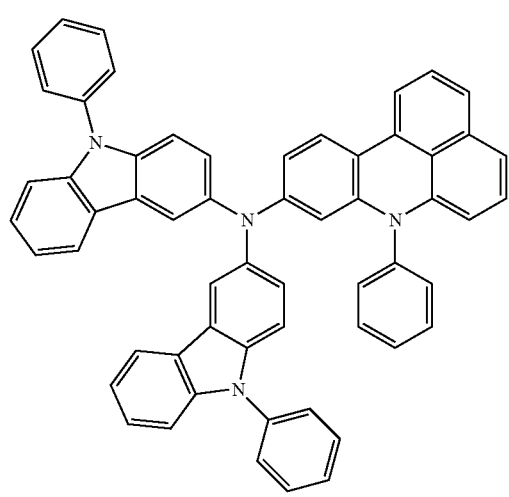
34
-continued
8
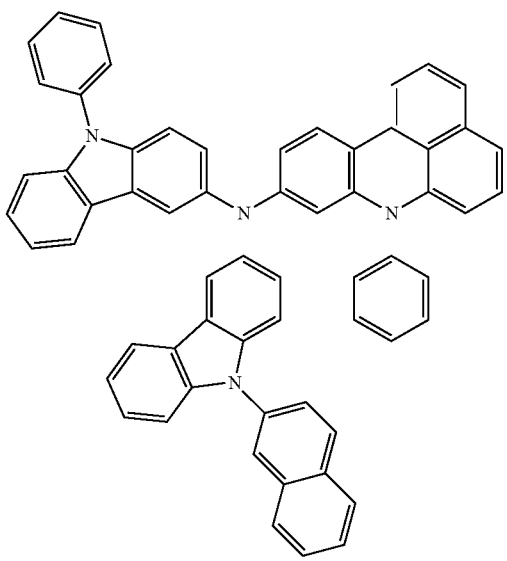
9
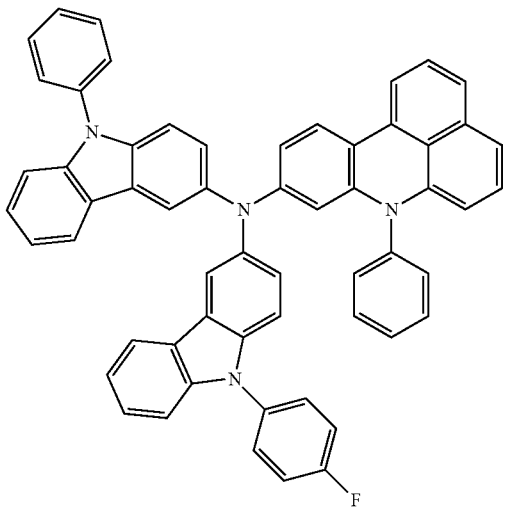
10

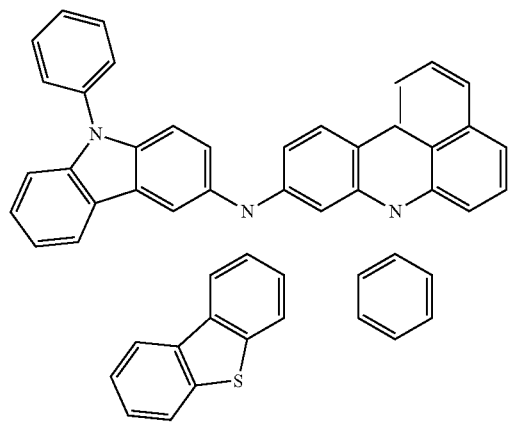
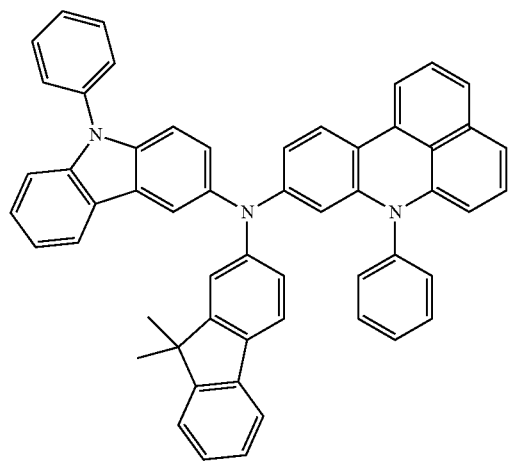
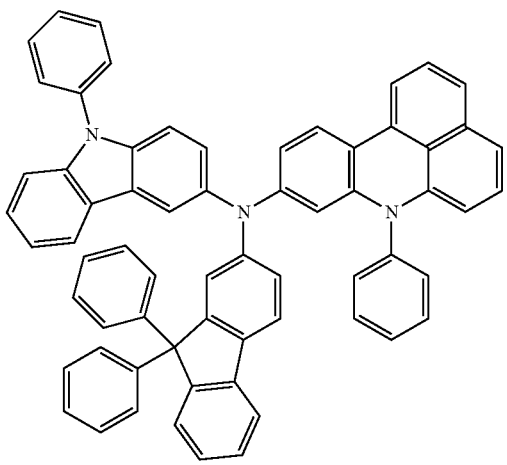
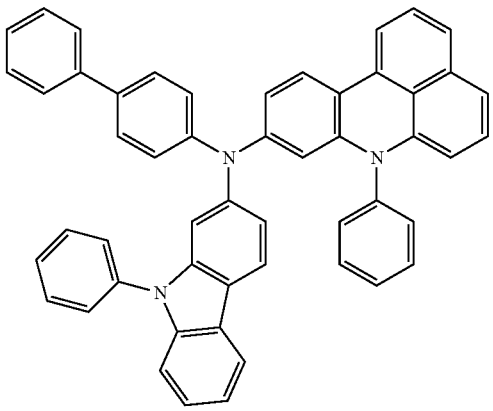

-continued
17
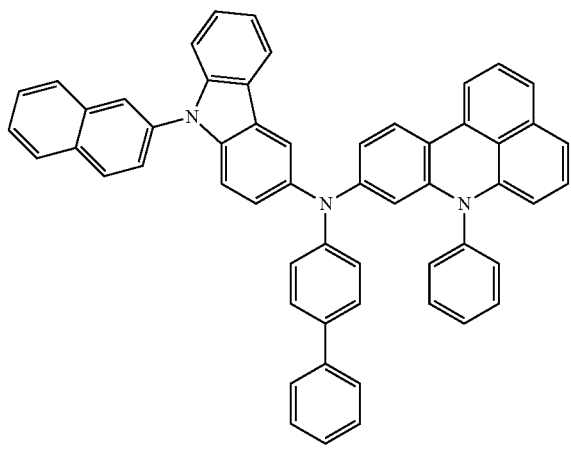
18
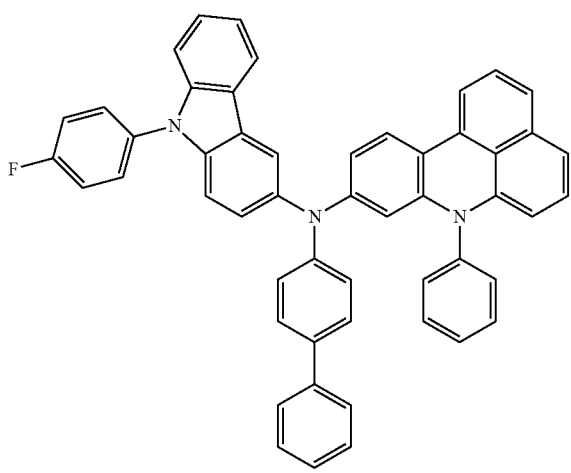
19
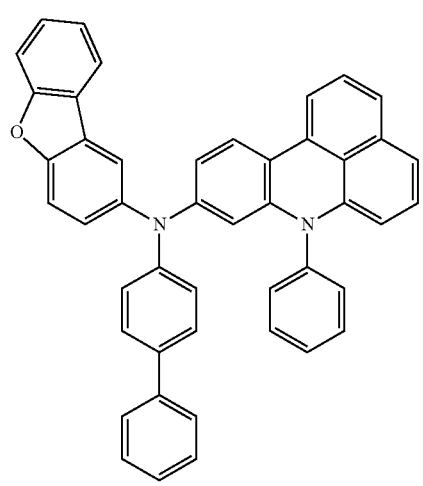
-continued
20
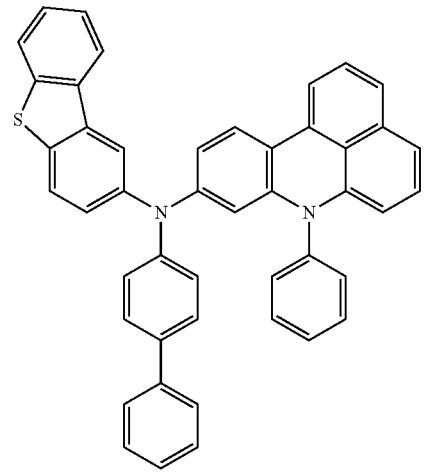
21
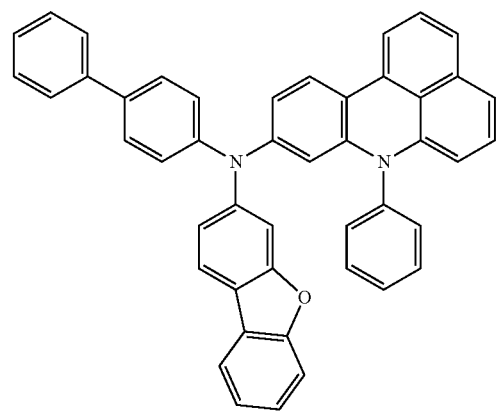
22
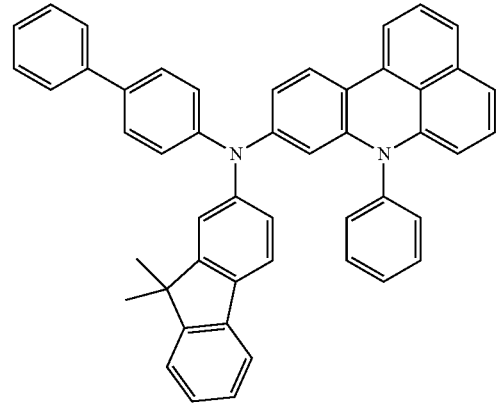

23
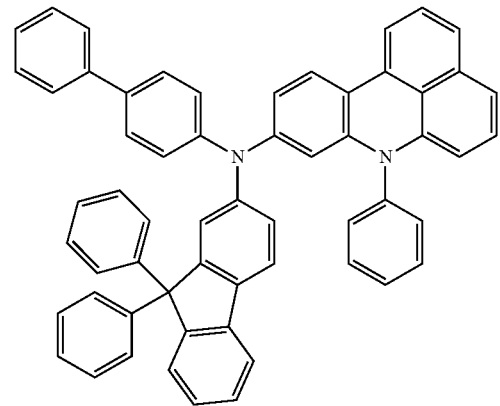
24
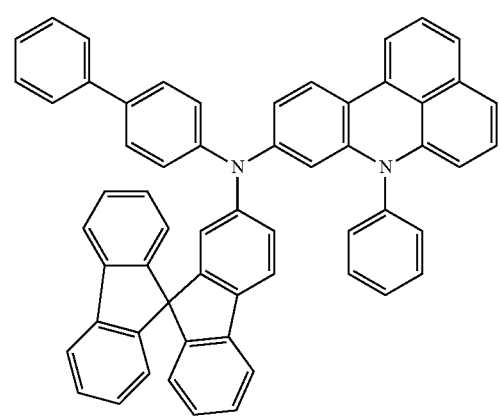
25
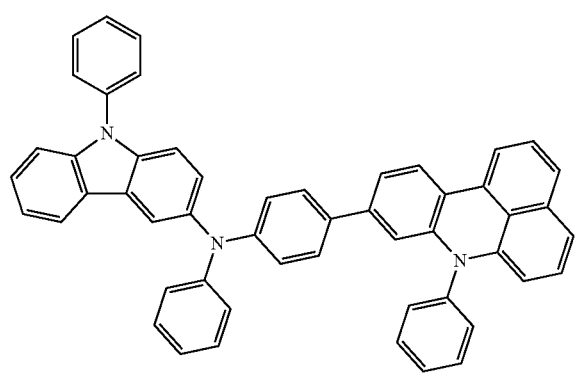
26
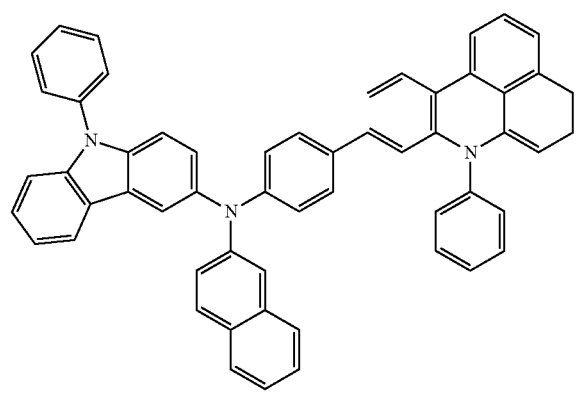
27
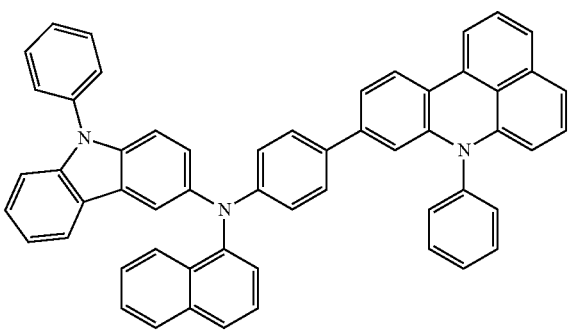
28
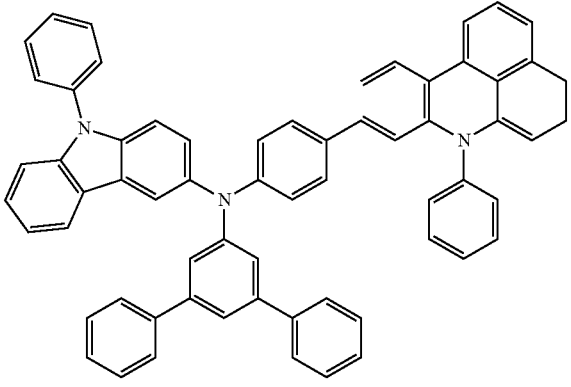
29

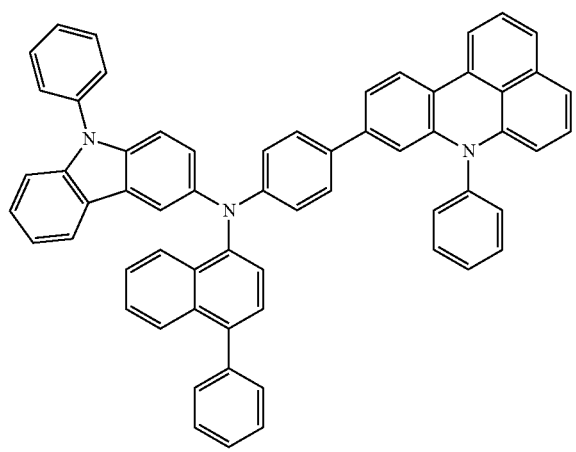
30
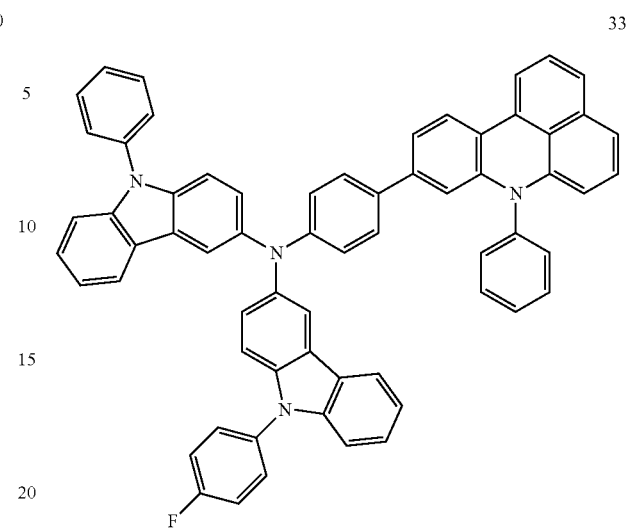
33
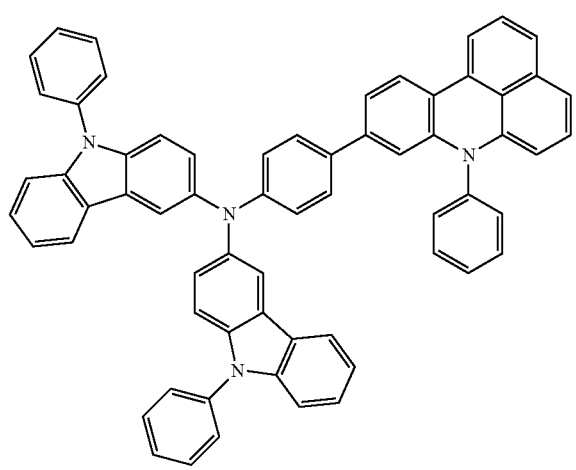
31
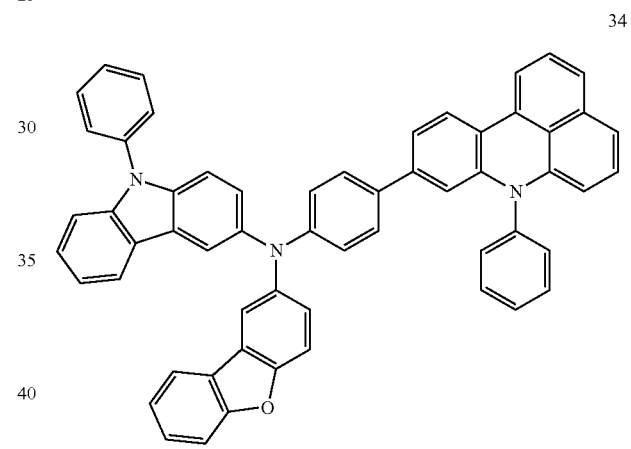
34
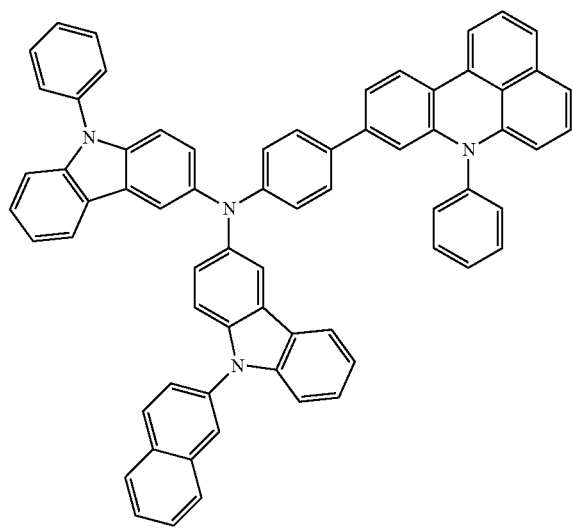
32
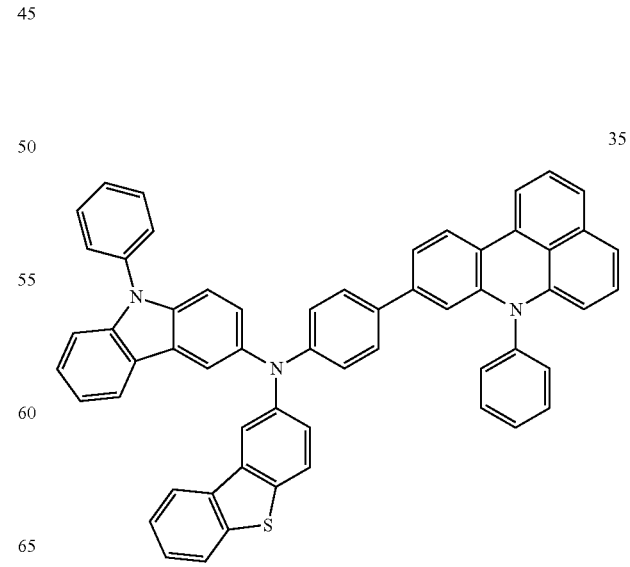
35

36
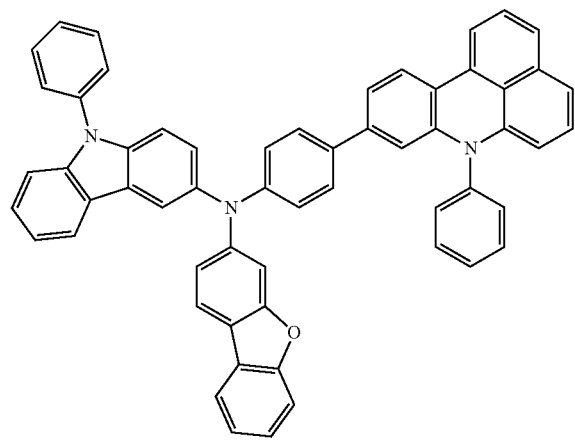
37
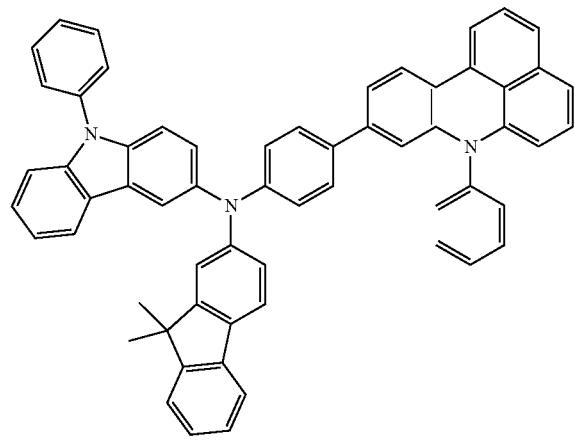
38
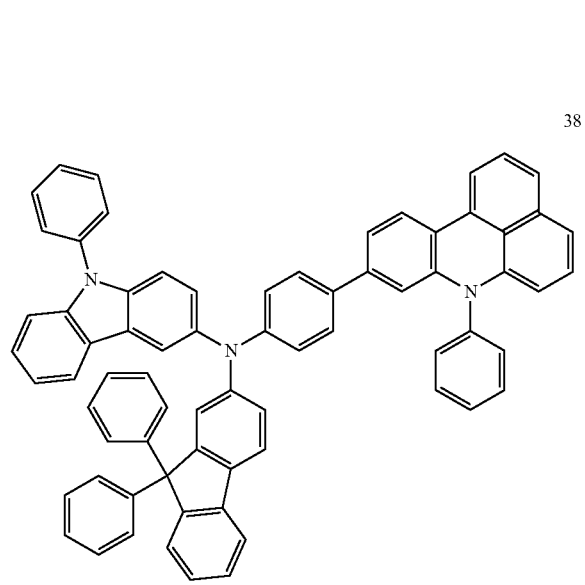
39
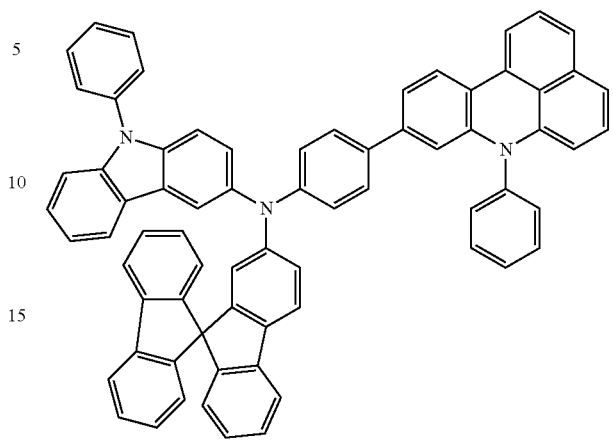
40
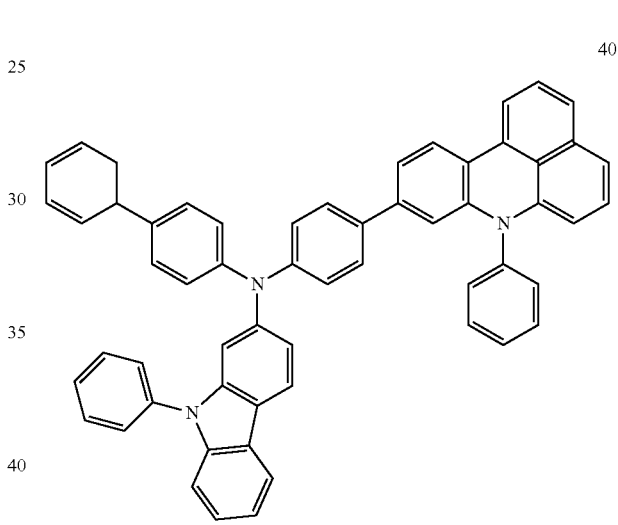
41
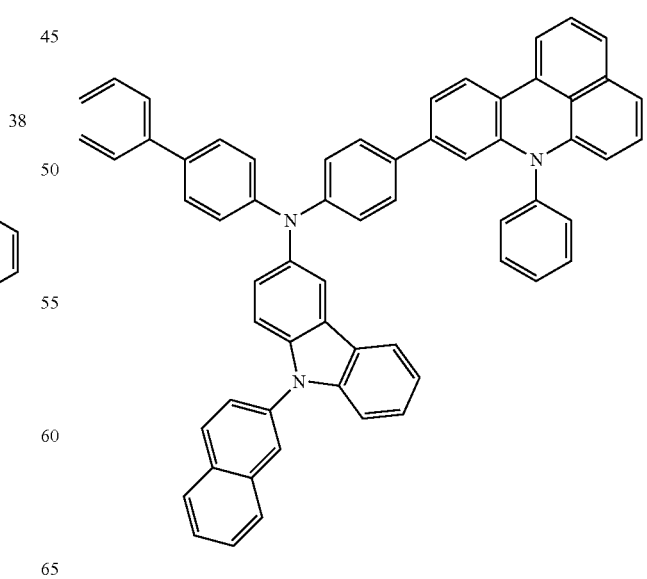

42
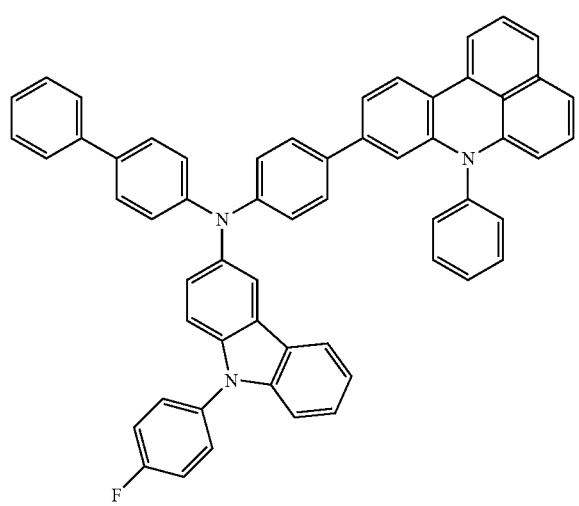
43
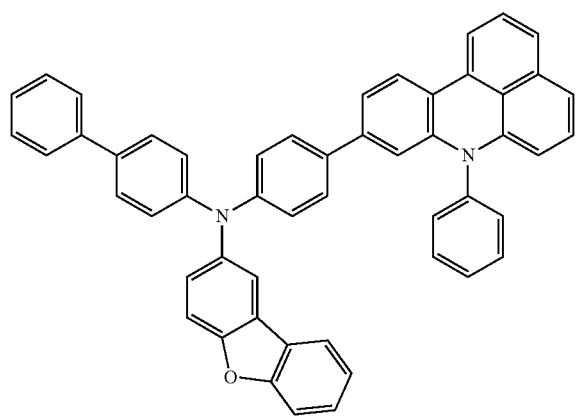
44
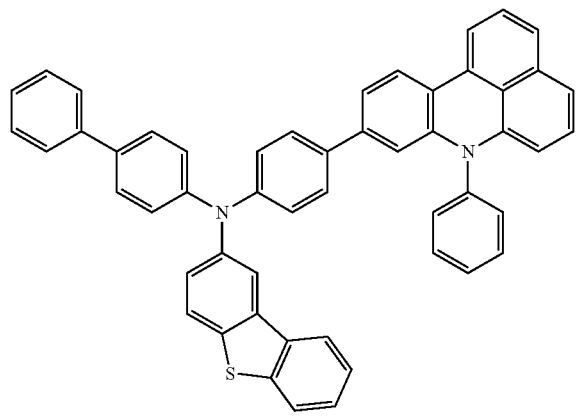
45
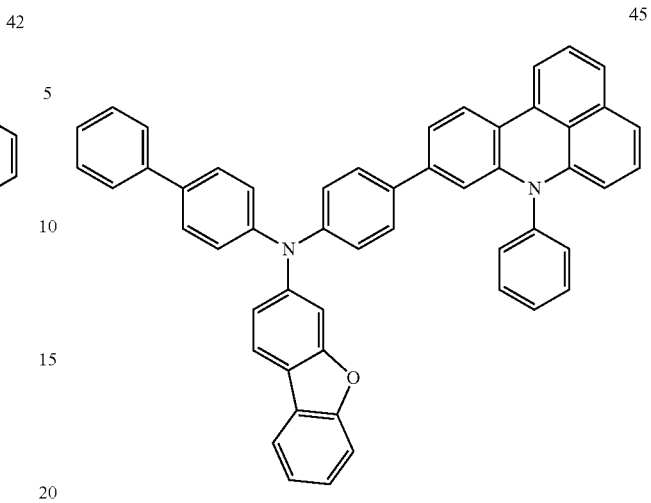
46
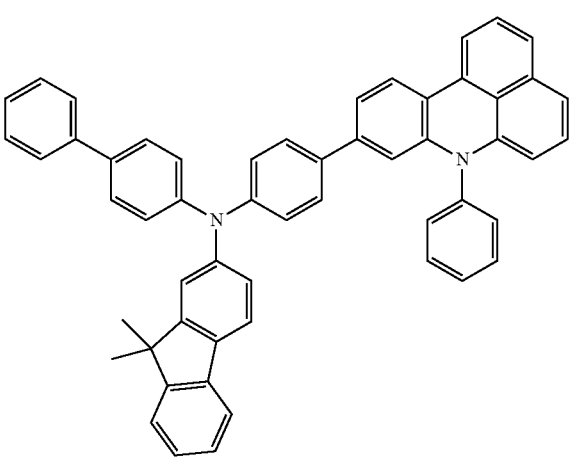
47
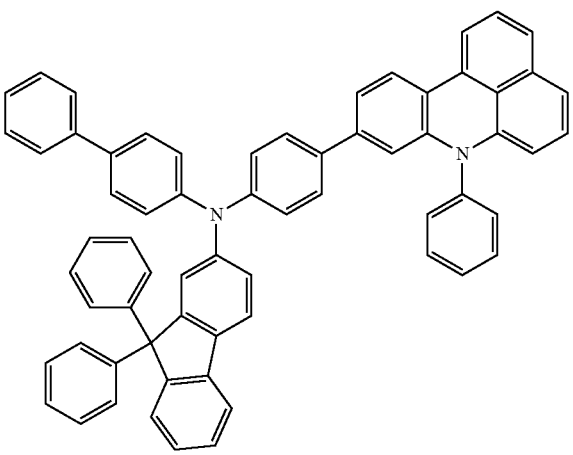

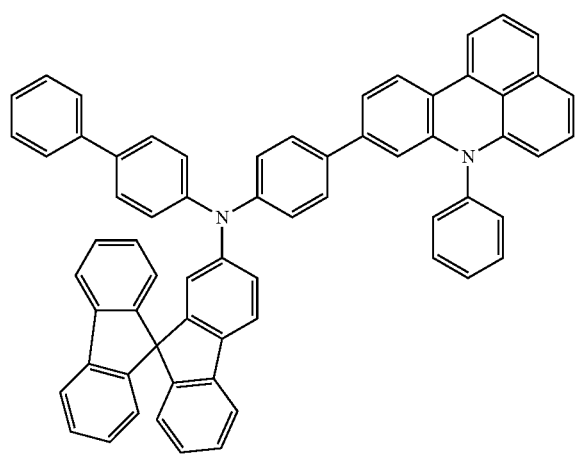
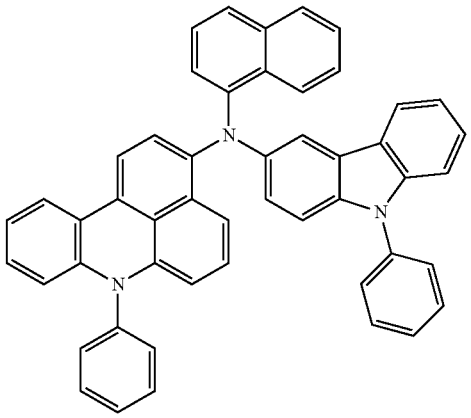
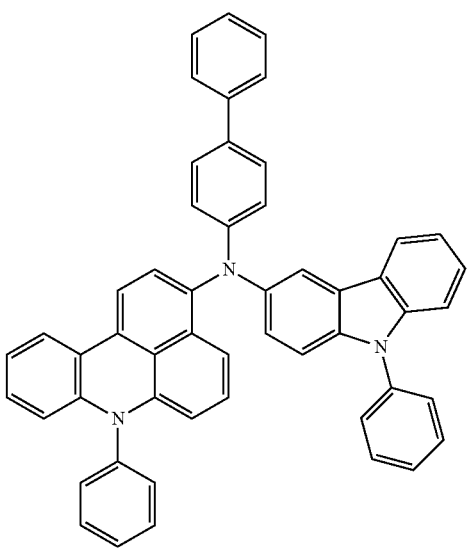
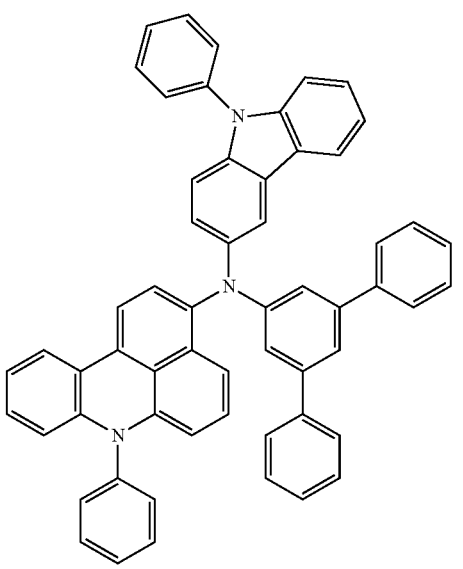

54
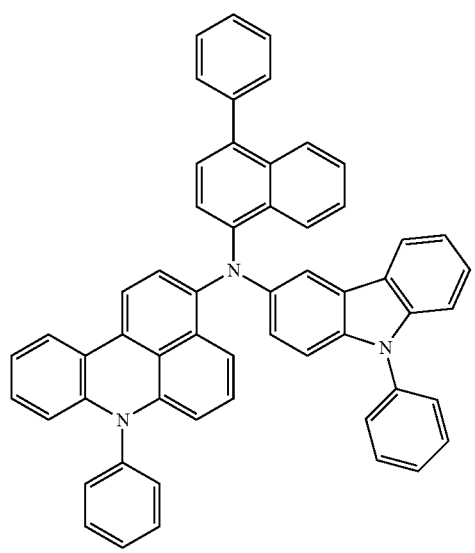
55
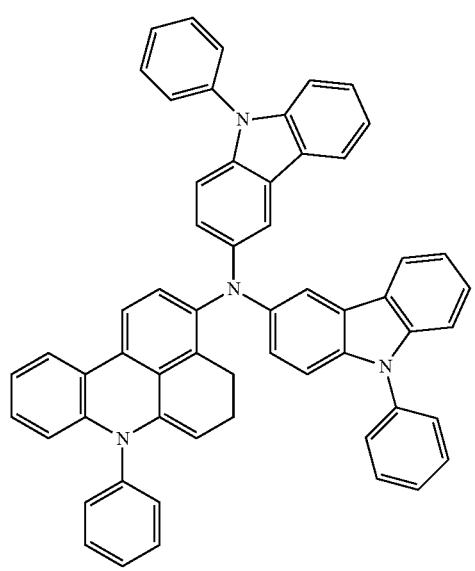
56
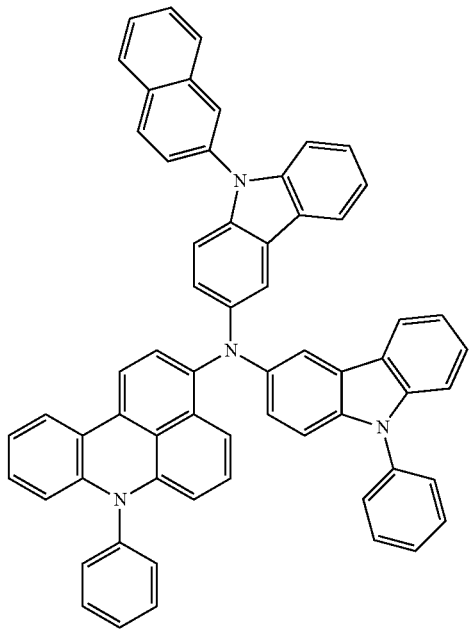
57
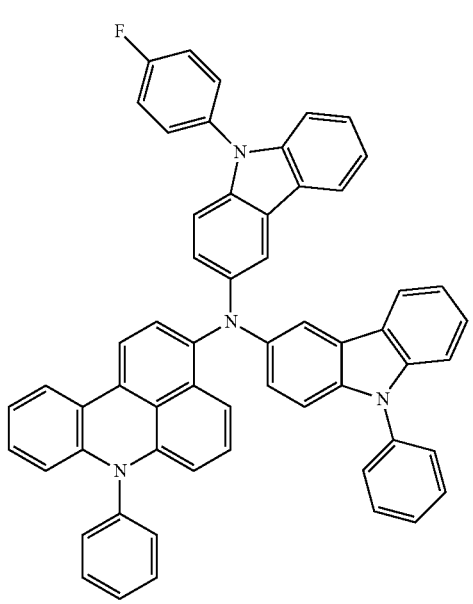

58
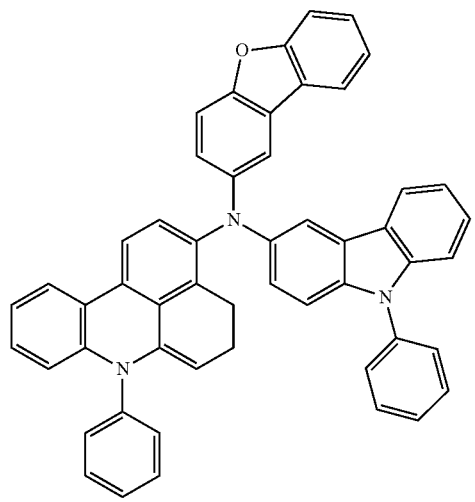
59
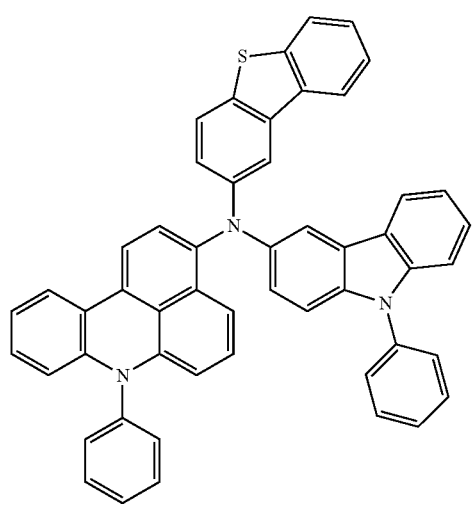
60
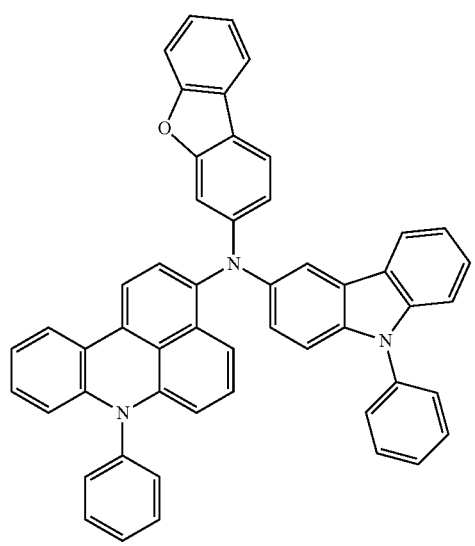
61
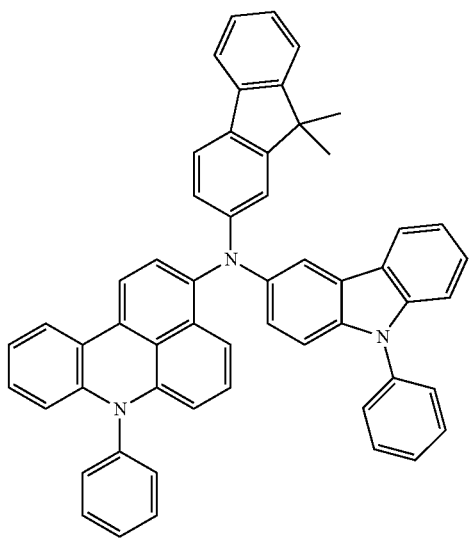
62
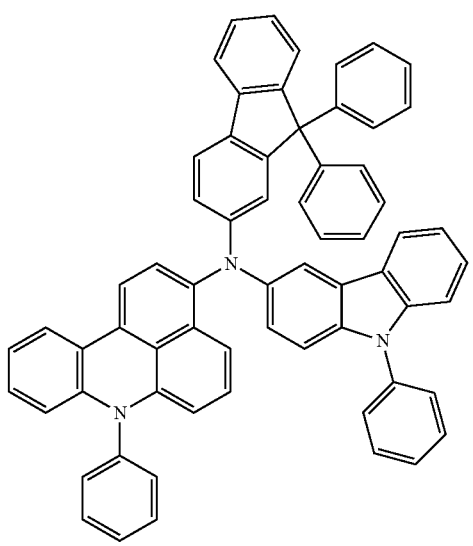
63

64
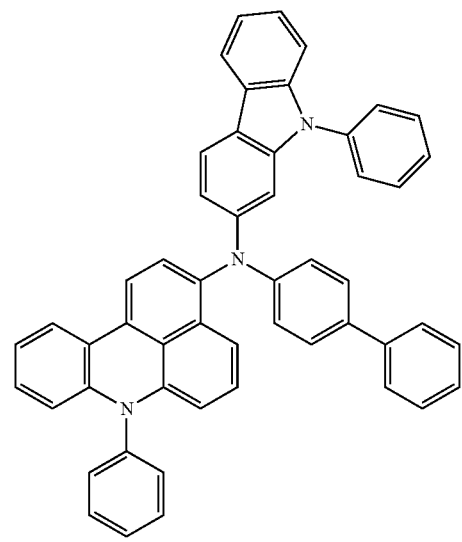
65
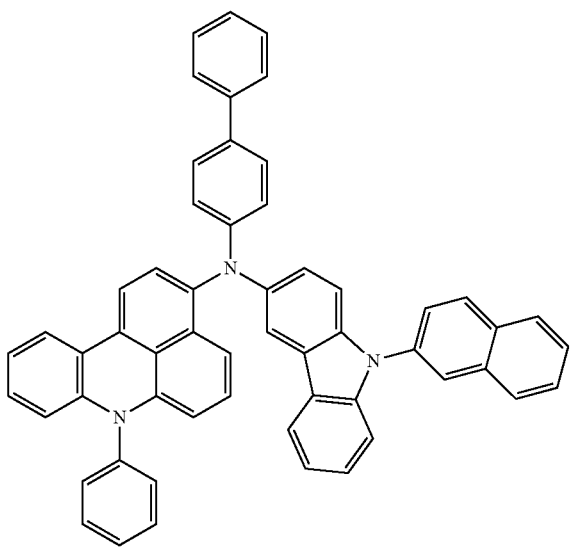
66
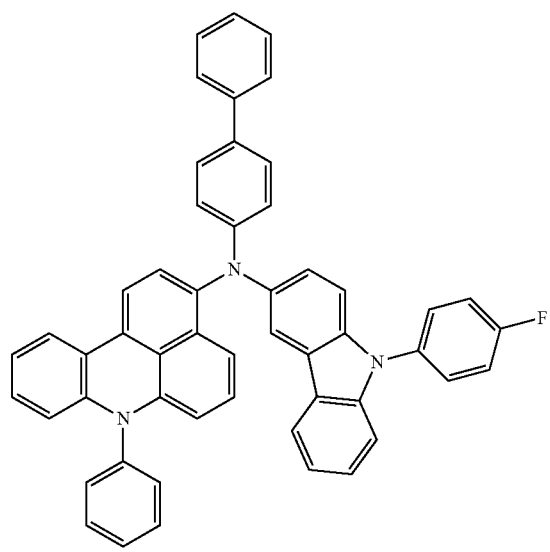
67
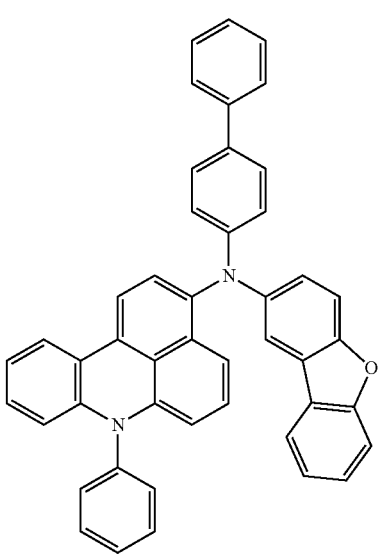
68
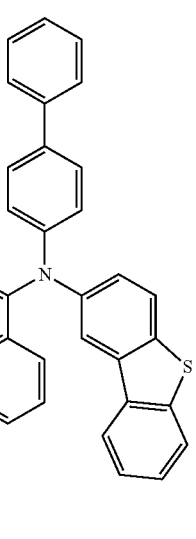
69
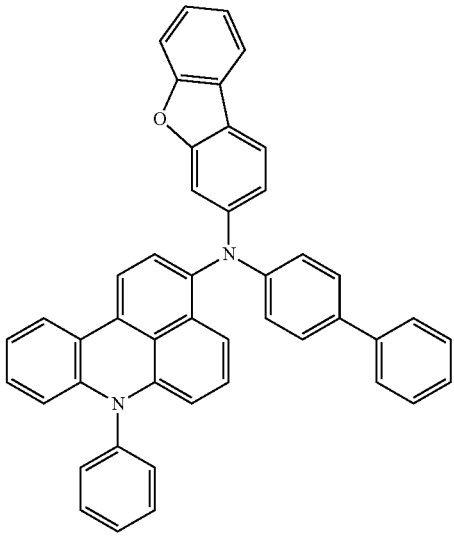

70 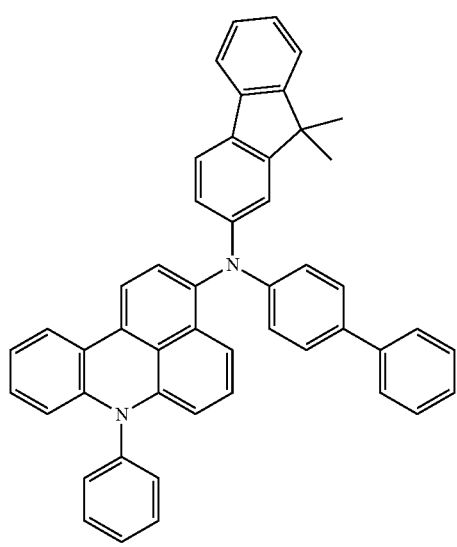
71 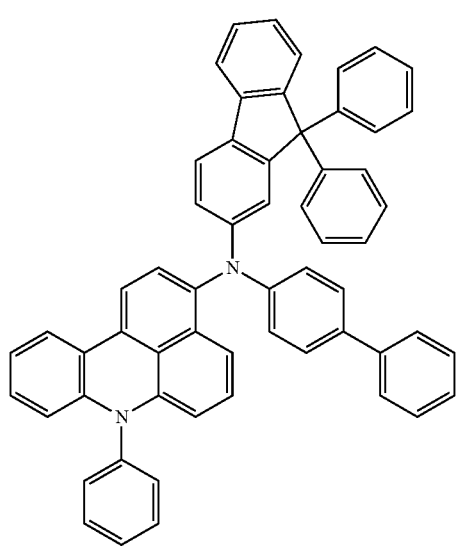
72 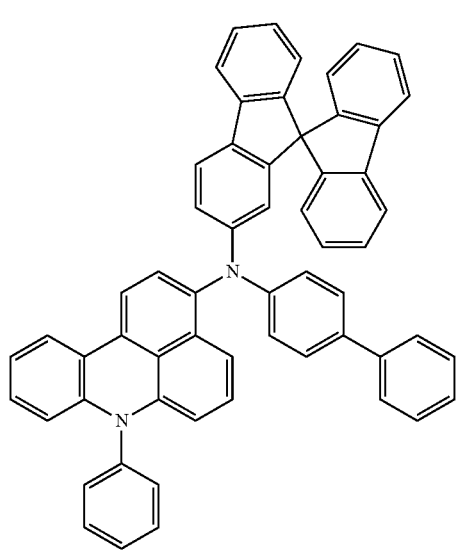
73 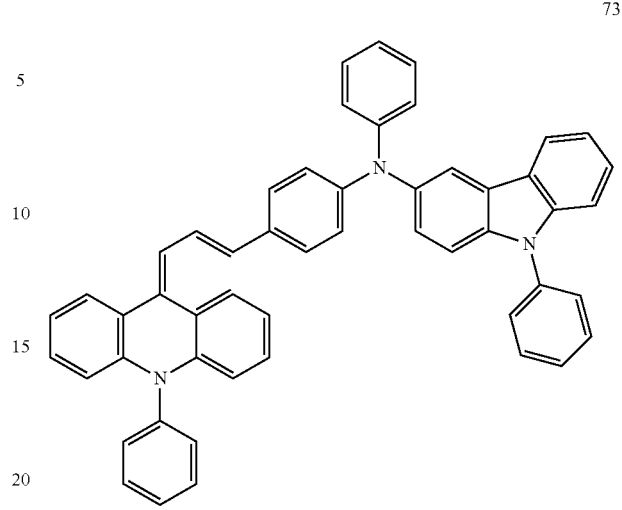
74 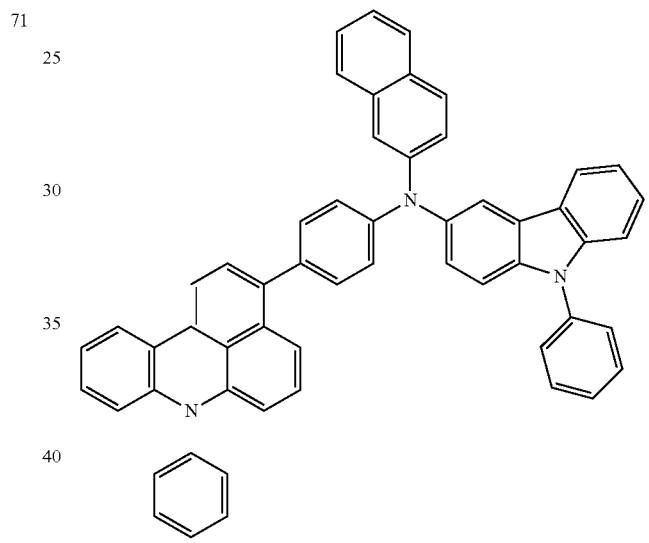
75 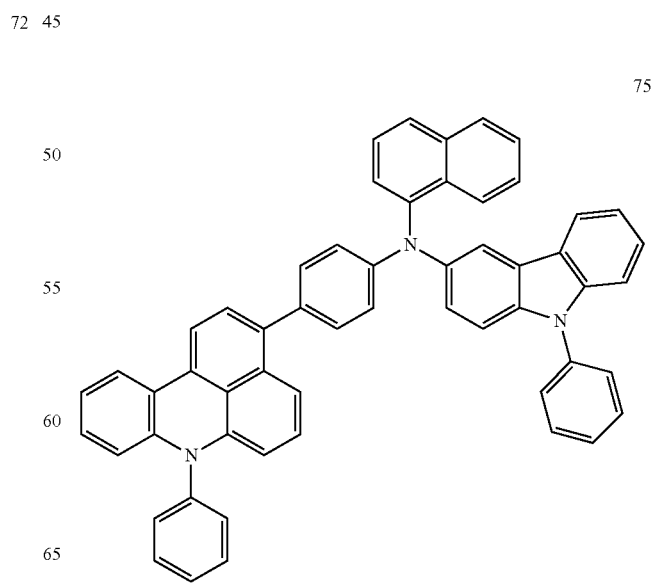

76
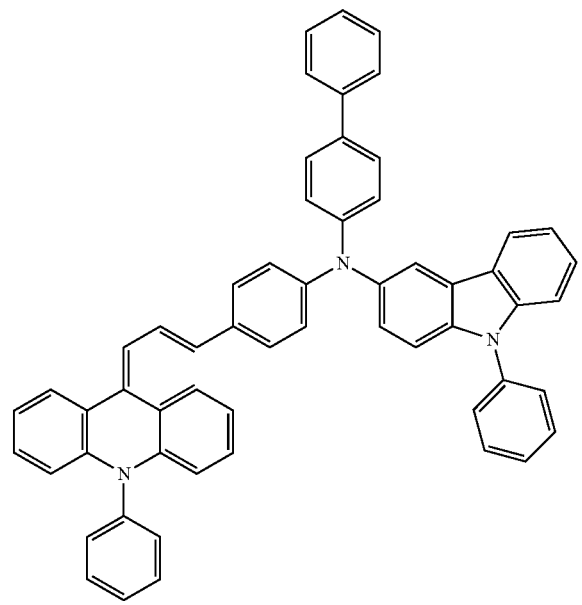
78
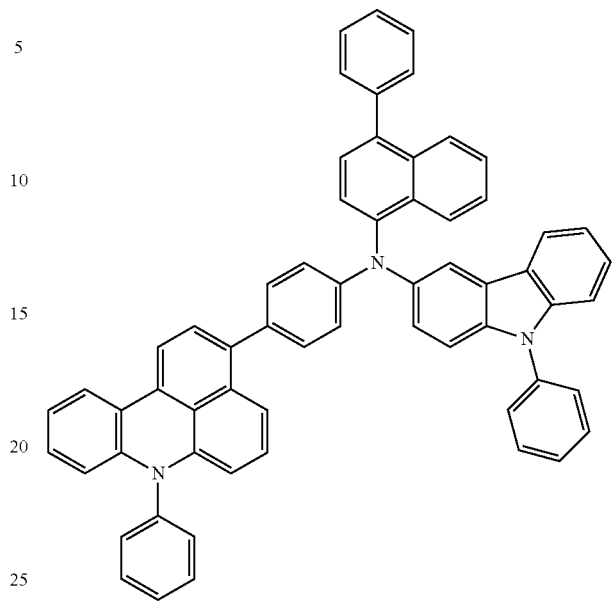
77
79
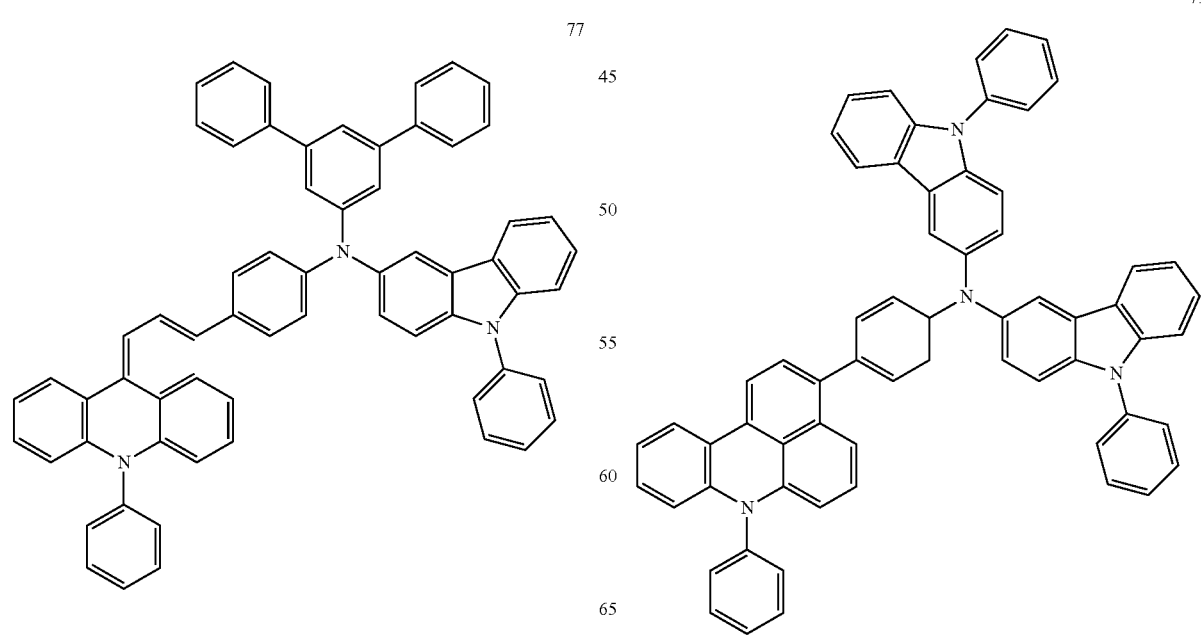

-continued
80
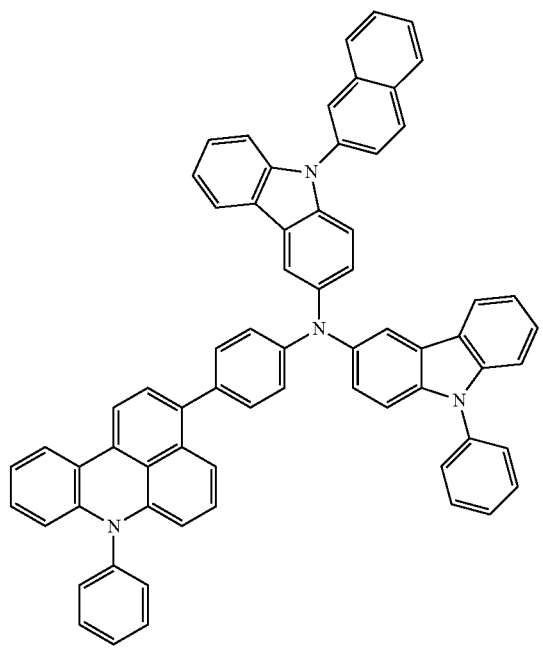
81
82
-continued
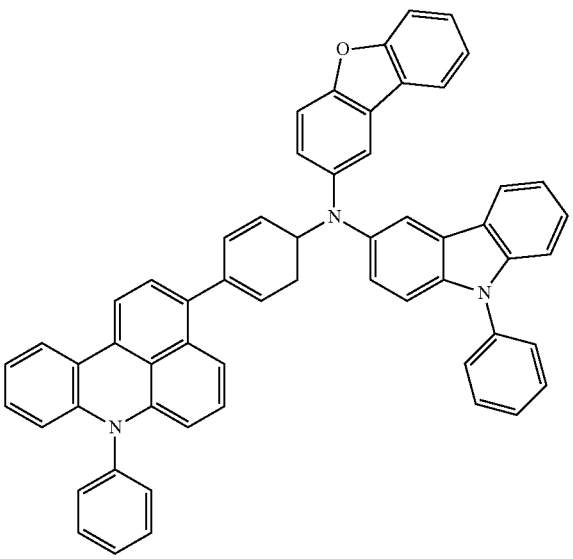
83
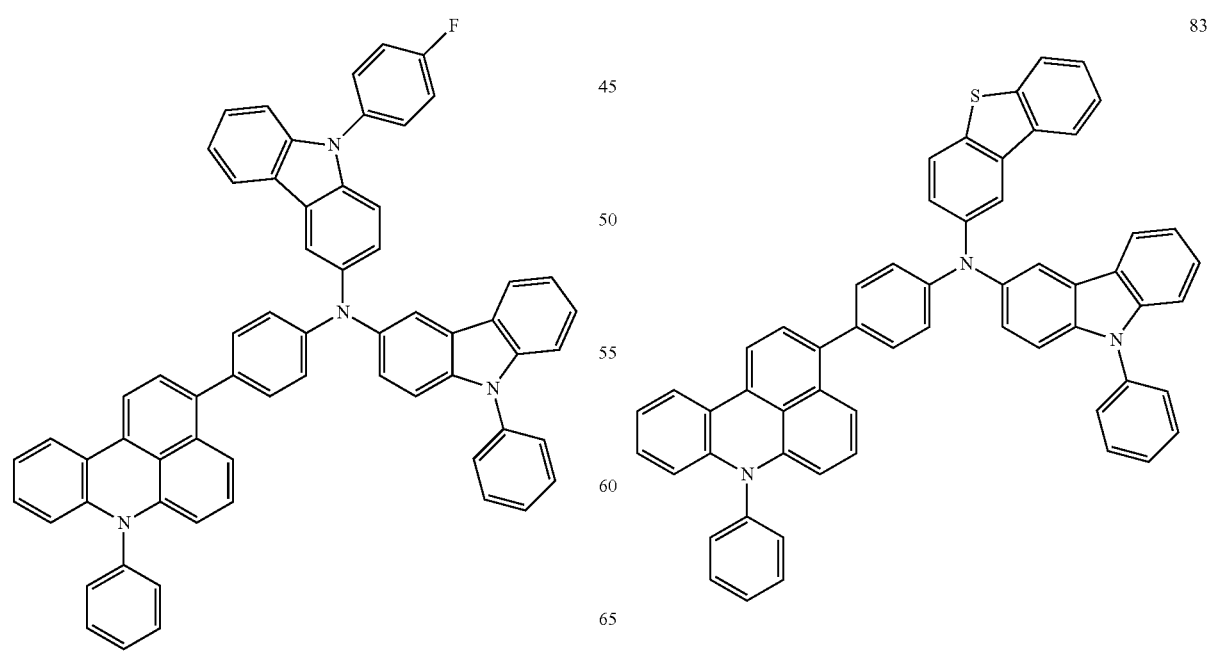

84
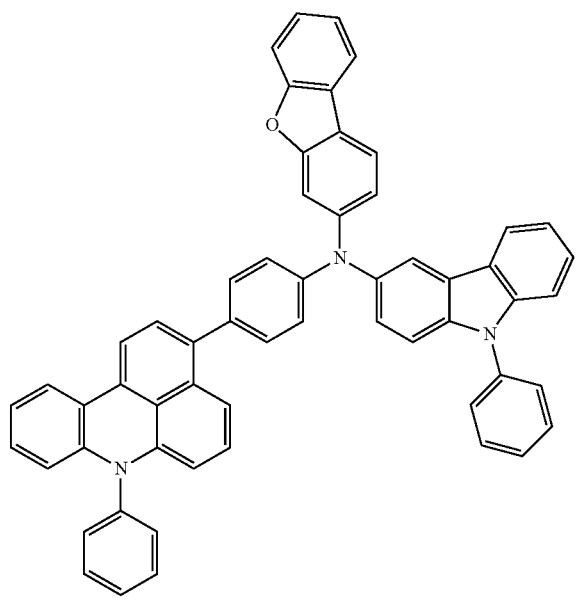
85
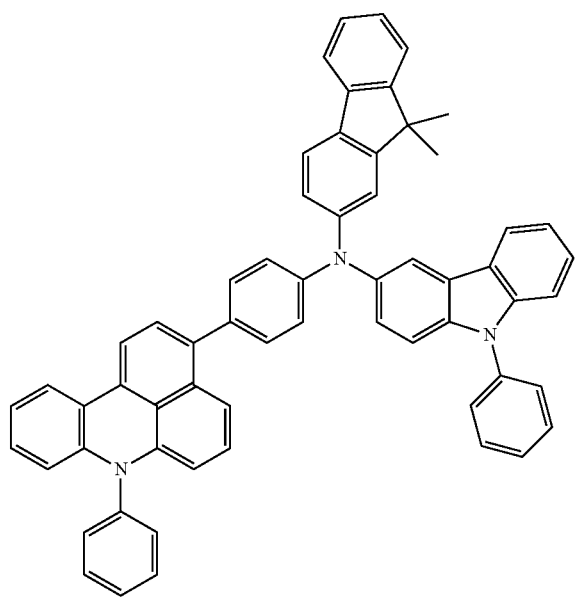
86
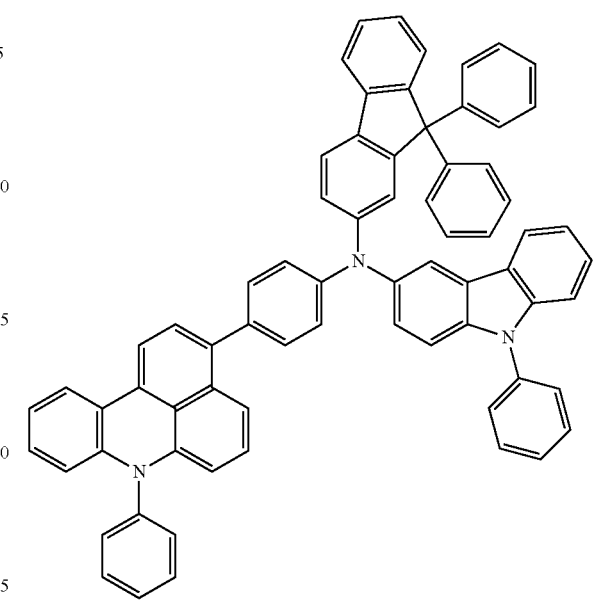
87
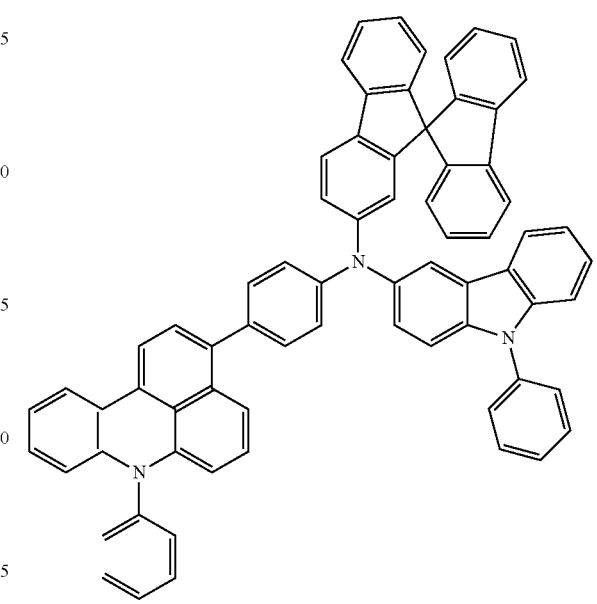

88
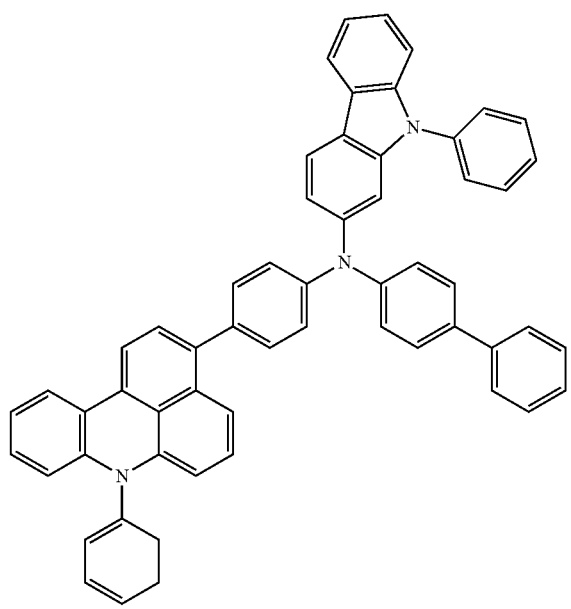
89
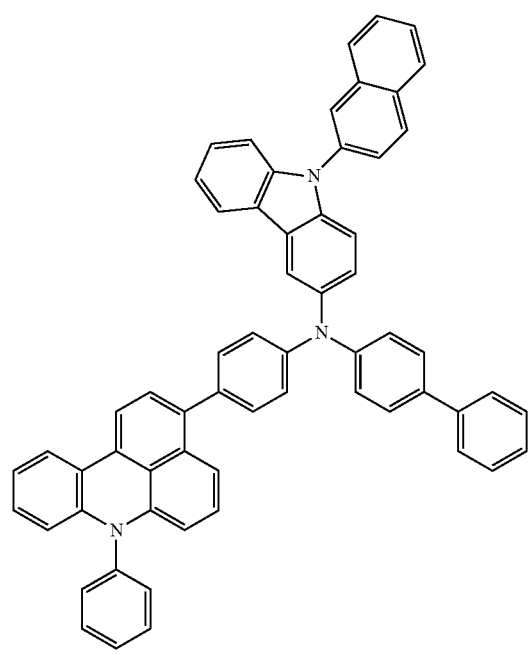
90
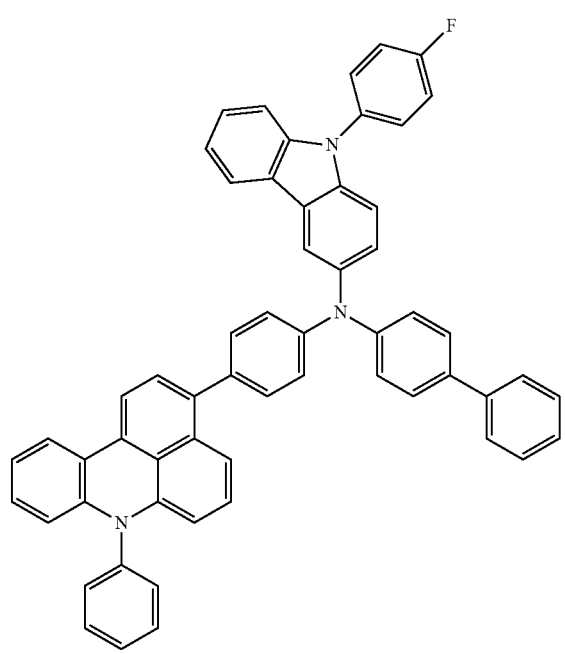
91
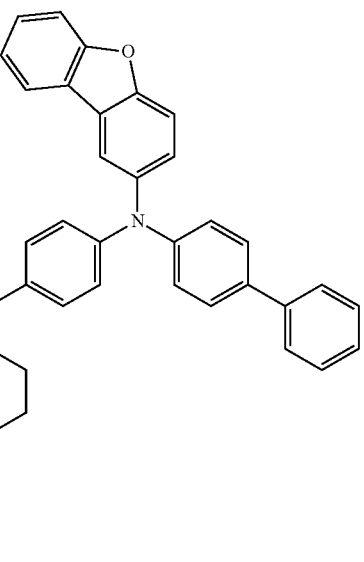

92
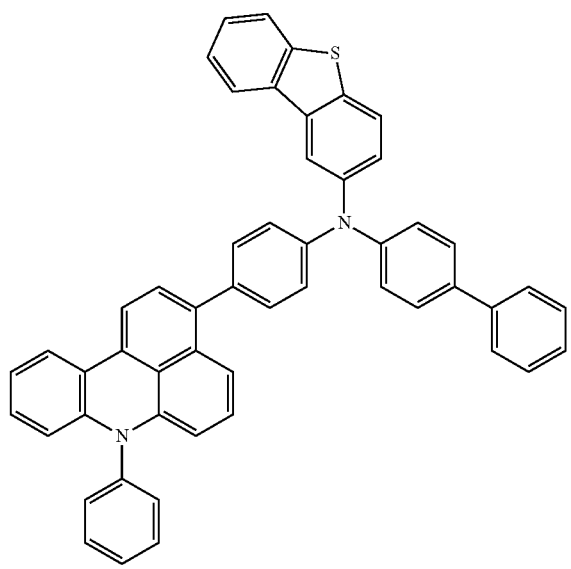
93
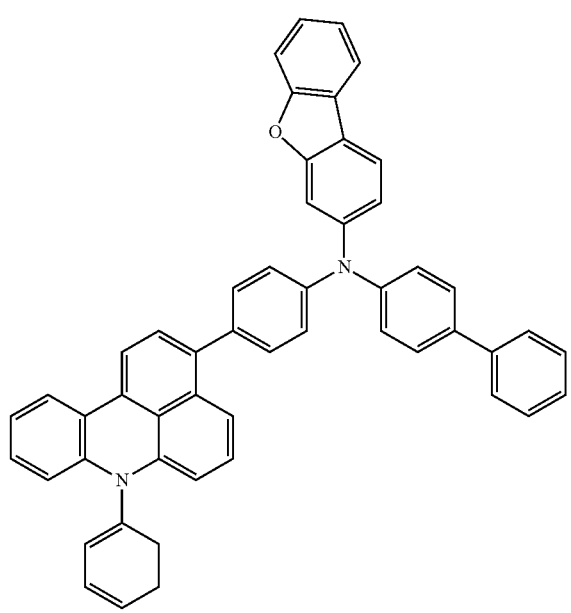
94
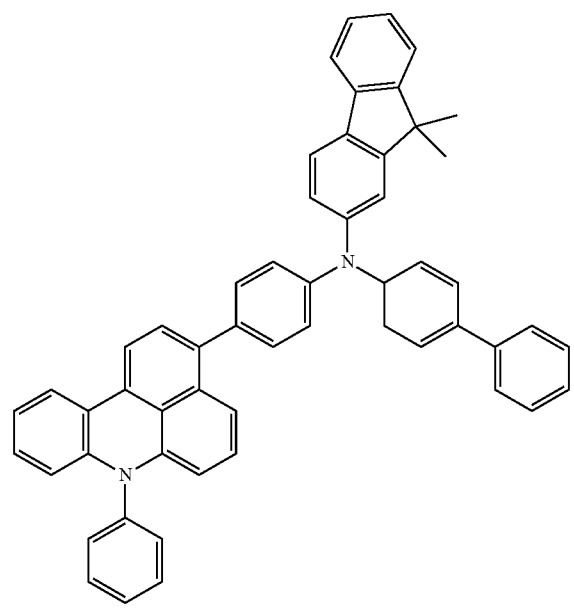
95
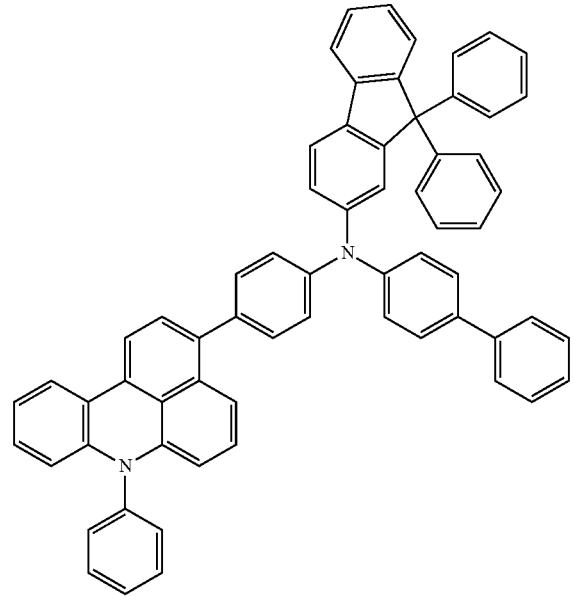

-continued

96

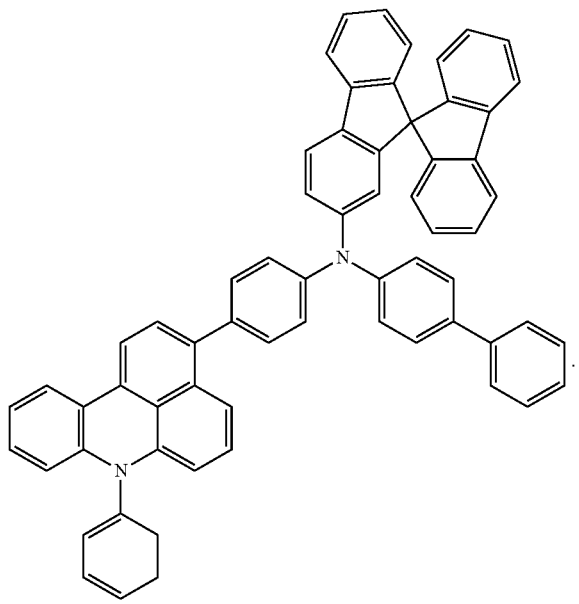

A substituent selected from $R_1$ to $R_{10}$ in Formula 1 may be the group represented by Formula 2. That is, the compound represented by Formula 1 may have at least one group represented by Formula 2.

At least one selected from $Ar_1$ and $Ar_2$ in Formula 2 may each independently be selected from a substituted or unsubstituted fluorenyl group, a substituted or unsubstituted spirobifluorenyl group, a substituted or unsubstituted carbazolyl group, a substituted or unsubstituted dibenzofuranyl group, a substituted or unsubstituted dibenzothiophenyl group, and a substituted or unsubstituted dibenzosilolyl group.

The condensed cyclic compound represented by Formula 1 may have a high glass transition temperature (Tg) or a high melting point. Accordingly, a heat resistance to Joule's heat, which may occur inside an organic layer and/or between the organic layer and an electrode, and durability under high-temperature conditions may increase. Accordingly, an organic light-emitting device including the condensed cyclic compound represented by Formula 1 may show excellent durability during storage and driving. According to embodiments of the present disclosure, the condensed cyclic compound represented by Formula 1 may have a higher melting point than that of a hole transport material of the related art. When deposited, the condensed cyclic compound represented by Formula 1 shows sublimating characteristics, and accordingly, compared to the hole transport material of the related art, may provide processability during a deposition process and an improvement in driving voltage of a device.

The condensed cyclic compound represented by Formula 1 may be synthesized by using one or more suitable organic synthesis methods. Such organic synthesis methods should become apparent to those of ordinary skill in the art by referring to the examples provided below.

At least one condensed cyclic compound represented by Formula 1 may be used between a pair of electrodes of an organic light-emitting device. For example, the condensed cyclic compound may be included in a hole transport region, for example, a hole transport layer. Accordingly, embodiments of the present disclosure provide an organic light-emitting device including: a first electrode; a second electrode facing the first electrode; and an organic layer between the first electrode and the second electrode, the organic layer including an emission layer, wherein the organic layer includes at least one condensed cyclic compound represented by Formula 1.

The expression "(an organic layer) includes at least one condensed cyclic compound" used herein may include a case in which (an organic layer) includes one or more identical compounds represented by Formula 1 and a case in which (an organic layer) includes two or more different condensed cyclic compounds represented by Formula 1.

For example, the organic layer may include, as the condensed cyclic compound, only Compound 1. In this regard, Compound 1 may be included in an emission layer of the organic light-emitting device. In some embodiments, the organic layer may include, as the condensed cyclic compound, Compound 1 and Compound 2. In this regard, Compound 1 and Compound 2 may both be included in the same layer (e.g., Compound 1 and Compound 2 may both be in an emission layer), or Compound 1 and Compound 2 may be in different layers (e.g., Compound 1 may be in a hole transport layer and Compound 2 may be in an emission layer).

The organic layer may include a hole transport region (between a first electrode (e.g., anode) and an emission layer) and an electron transport region (between the emission layer and a second electrode (e.g., cathode)). The hole transport region may include at least one layer selected from a hole injection layer, a hole transport layer, a buffer layer, and an electron blocking layer; and the electron transport region may include at least one layer selected from a hole blocking layer, an electron transport layer, and an electron injection layer. At least one selected from the hole transport region and the emission layer may include at least one condensed cyclic compound represented by Formula 1. For example, the hole transport region may include the hole transport layer, and the hole transport layer may include at least one condensed cyclic compound represented by Formula 1.

The term "organic layer" used herein may refer to a single layer and/or a plurality of layers disposed (e.g., positioned) between the first electrode and the second electrode of the organic light-emitting device. A material included in the "organic layer" is not limited to an organic material.

The drawing is a schematic view of an organic light-emitting device 10 according to an embodiment. The organic light-emitting device 10 includes a first electrode 110, an organic layer 150, and a second electrode 190.

Hereinafter, the structure of an organic light-emitting device according to an embodiment and a method of manufacturing an organic light-emitting device according to an embodiment will be described in connection with the drawing.

In the drawing, a substrate may be additionally disposed under the first electrode 110 or above the second electrode 190. The substrate may be a glass substrate and/or a transparent plastic substrate, each having excellent mechanical strength, thermal stability, transparency, surface smoothness, ease of handling, and/or water-resistance.

The first electrode 110 may be formed by depositing or sputtering a material for forming the first electrode 110 on the substrate. When the first electrode 110 is an anode, for example, the material for forming the first electrode 110 may be selected from materials with a high work function, so as to facilitate hole injection. The first electrode 110 may be a reflective electrode, a semi-transmissive electrode, or a transmissive electrode. The material for forming the first electrode 110 may be a transparent and highly conductive material, and non-limiting examples of such material include indium tin oxide (ITO), indium zinc oxide (IZO), tin oxide ($SnO_2$), and zinc oxide (ZnO). When the first electrode 110 is a semi-transmissive electrode or a reflective electrode, at least one selected from magnesium (Mg), aluminum (Al), aluminum-lithium (Al—Li), calcium (Ca), magnesium-indium (Mg—In), and magnesium-silver (Mg—Ag) may be used as a material for forming the first electrode 110.

The first electrode 110 may have a single-layer structure, or a multi-layer structure including two or more layers. For example, the first electrode 110 may have a three-layered structure of ITO/Ag/ITO, but the structure of the first electrode 110 is not limited thereto.

The organic layer 150 may be disposed on the first electrode 110. The organic layer 150 may include an emission layer.

The organic layer 150 may further include a hole transport region between the first electrode and the emission layer, and an electron transport region between the emission layer and the second electrode.

The hole transport region may include at least one selected from a hole injection layer (HIL), a hole transport layer (HTL), a buffer layer, and an electron blocking layer (EBL); and the electron transport region may include at least one selected from a hole blocking layer (HBL), an electron transport layer (ETL), and an electron injection layer (EIL), but they are not limited thereto.

The hole transport region may have a single-layered structure formed of a single material, a single-layered structure formed of a plurality of different materials, or a multi-layered structure having a plurality of layers formed of a plurality of different materials.

For example, the hole transport region may have a single-layered structure formed of a plurality of different materials, or a structure of hole injection layer/hole transport layer, a structure of hole injection layer/hole transport layer/buffer layer, a structure of hole injection layer/buffer layer, a structure of hole transport layer/buffer layer, or a structure of hole injection layer/hole transport layer/electron blocking layer, wherein the layers of each structure are sequentially stacked from the first electrode 110 in this stated order, but the structure of the hole transport region is not limited thereto.

When the hole transport region includes a hole injection layer, the hole injection layer may be formed on the first electrode 110 by using one or more suitable methods such as vacuum deposition, spin coating, casting, a Langmuir-Blodgett (LB) method, ink-jet printing, laser-printing, and/or laser-induced thermal imaging.

When a hole injection layer is formed by vacuum deposition, for example, the vacuum deposition may be performed at a deposition temperature of about 100 to about 500° C., at a vacuum degree of about $10^{-8}$ to about $10^{-3}$ torr, and at a deposition rate of about 0.01 to about 100 Å/sec, by taking into account a compound for forming the hole injection layer to be deposited, and the structure of the hole injection layer to be formed.

When a hole injection layer is formed by spin coating, for example, the spin coating may be performed at a coating rate of about 2000 rpm to about 5000 rpm, and at a temperature of about 80° C. to 200° C., by taking into account a compound for forming the hole injection layer to be deposited, and the structure of the hole injection layer to be formed.

When the hole transport region includes a hole transport layer, the hole transport layer may be formed on the first electrode 110 or the hole injection layer by using one or more suitable methods such as vacuum deposition, spin coating, casting, a LB method, ink-jet printing, laser-printing, and/or laser-induced thermal imaging. When the hole transport layer is formed by vacuum deposition and/or spin coating, deposition and coating conditions for the hole transport layer may be the same as (or similar to) the deposition and coating conditions for the hole injection layer.

The hole transport region may include the condensed cyclic compound represented by Formula 1. For example, the hole transport region may include the hole transport layer, and the hole transport layer may include the condensed cyclic compound represented by Formula 1.

In various embodiments, the hole transport region may include at least one selected from m-MTDATA, TDATA, 2-TNATA, NPB, β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), (polyaniline)/poly(4-styrenesulfonate) (PANI/PSS), a compound represented by Formula 201, and a compound represented by Formula 202:

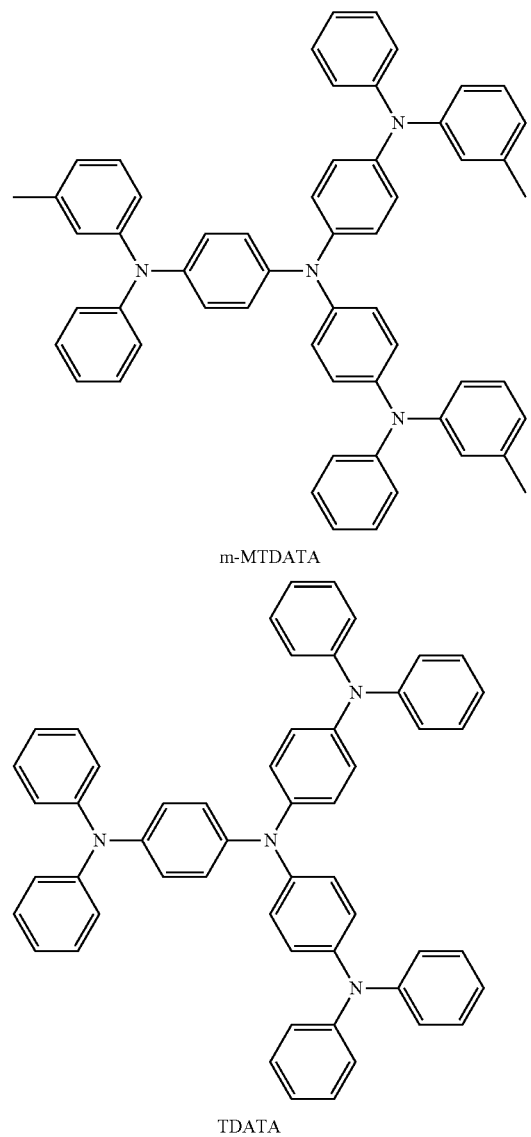

m-MTDATA

TDATA

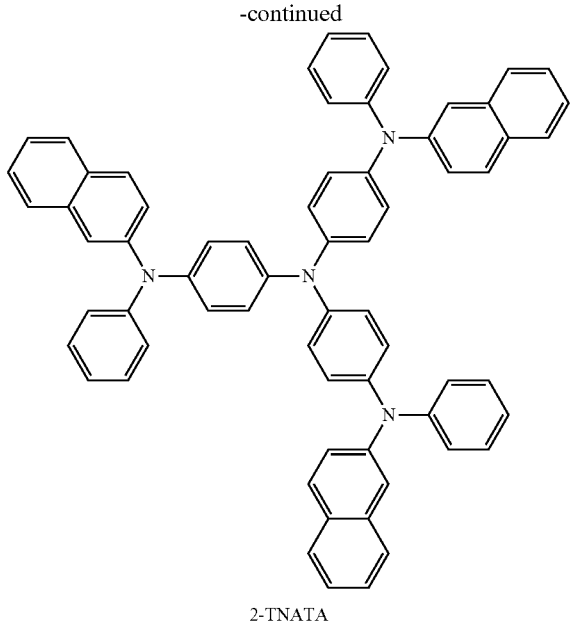
2-TNATA
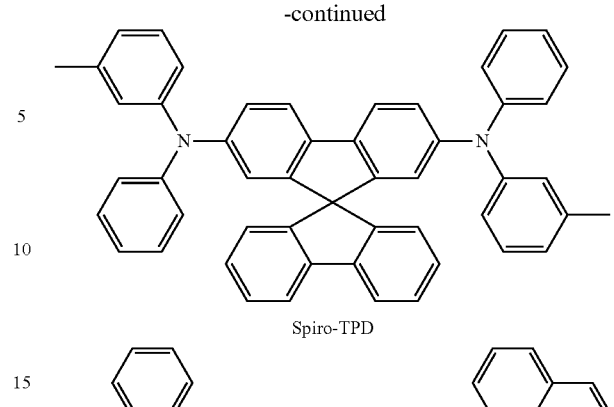
Spiro-TPD
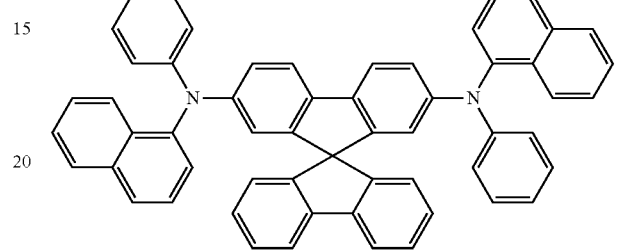
Spiro-NPB
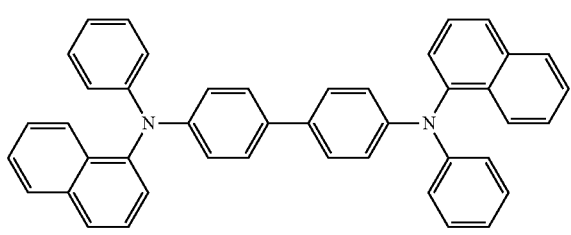
NPB
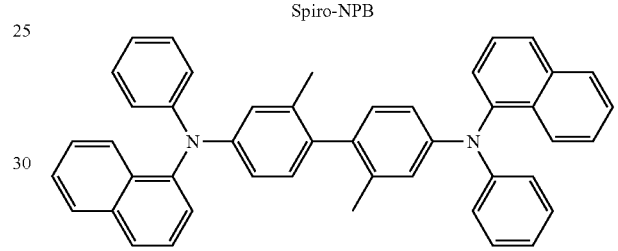
methylated NPB
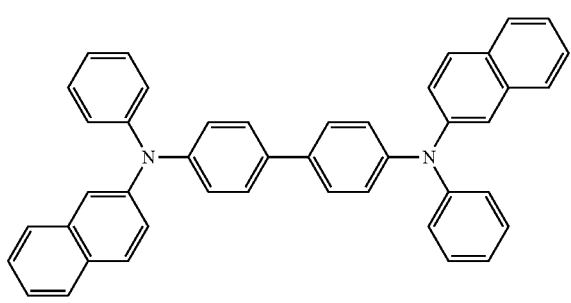
β-NPB
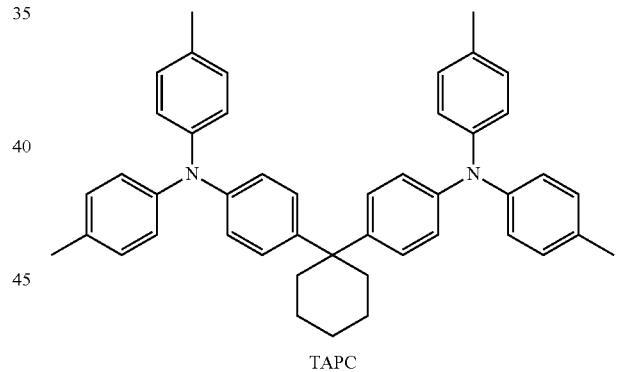
TAPC
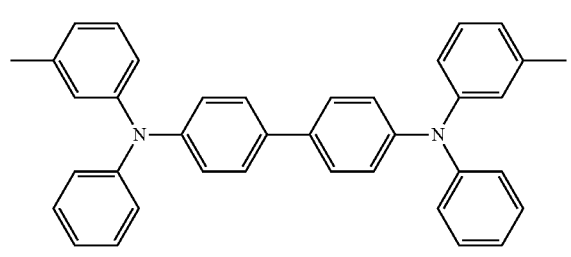
TPD
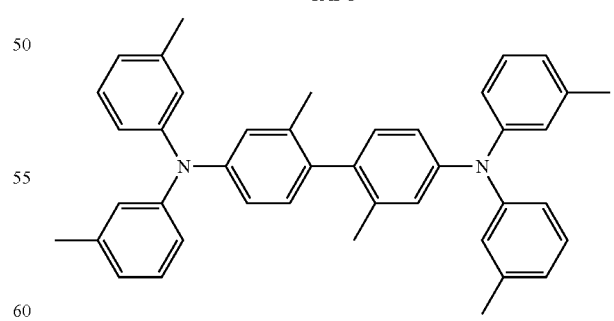
HMTPD
Formula 201
$$R_{201}\!-\!(L_{201})_{xa1}\!-\!N\!\begin{array}{l}(L_{202})_{xa2}\!-\!R_{202}\\ (L_{203})_{xa3}\!-\!R_{203}\end{array}$$

-continued

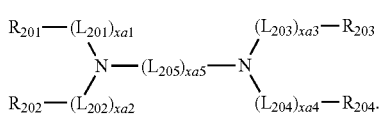

Formula 202

In Formulae 201 and 202,

Descriptions of $L_{201}$ to $L_{205}$ may each independently be the same as the description provided in connection with $L_1$;

xa1 to xa4 may each independently be selected from 0, 1, 2, and 3;

xa5 may be selected from 1, 2, 3, 4, and 5; and $R_{201}$ to $R_{204}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formulae 201 and 202, $L_{201}$ to $L_{205}$ may each independently be selected from the group consisting of:

a phenylene group, a naphthylene group, a fluorenylene group, spiro-bifluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, and a phenylene group, a naphthylene group, a fluorenylene group, spiro-bifluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may each independently be 0, 1, or 2;

xa5 may be 1, 2, or 3;

$R_{201}$ to $R_{204}$ may each independently be selected from the group consisting of:

a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, an azulenyl group, a fluorenyl group, spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

but embodiments of the present disclosure are not limited thereto.

The compound represented by Formula 201 may be represented by Formula 201A:

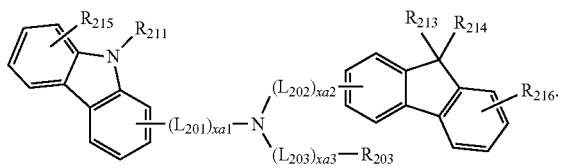

Formula 201A

For example, the compound represented by Formula 201 may be represented by Formula 201A-1 below, but is not limited thereto:

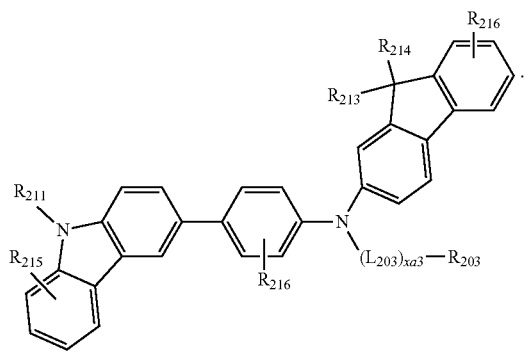

Formula 201A-1

For example, the compound represented by Formula 202 may be represented by Formula 202A below, but is not limited thereto:

Formula 202A

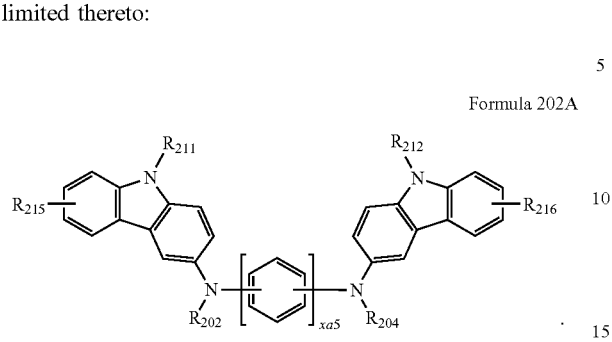

Regarding Formulae 201A, 201A-1, and 202A, $L_{201}$ to $L_{203}$, xa1 to xa3, xa5, and $R_{202}$ to $R_{204}$ are already described above; descriptions of $R_{211}$ and $R_{212}$ may each independently be understood by referring to the description of $R_{203}$; and $R_{213}$ to $R_{216}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

The compound represented by Formula 201, and the compound represented by Formula 202 may each independently include any of compounds HT1 to HT20 illustrated below, but are not limited thereto.

HT1

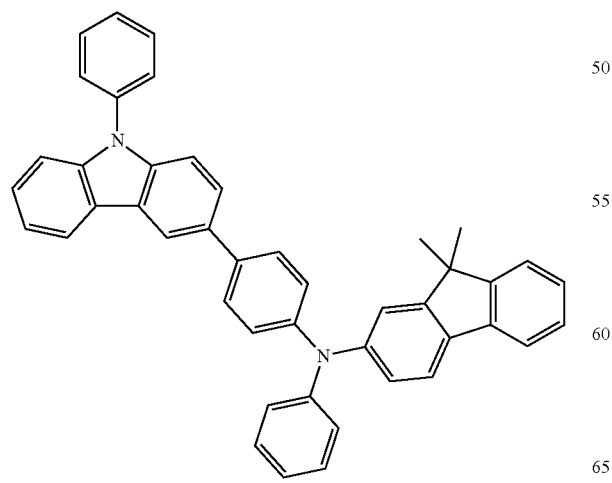

HT2

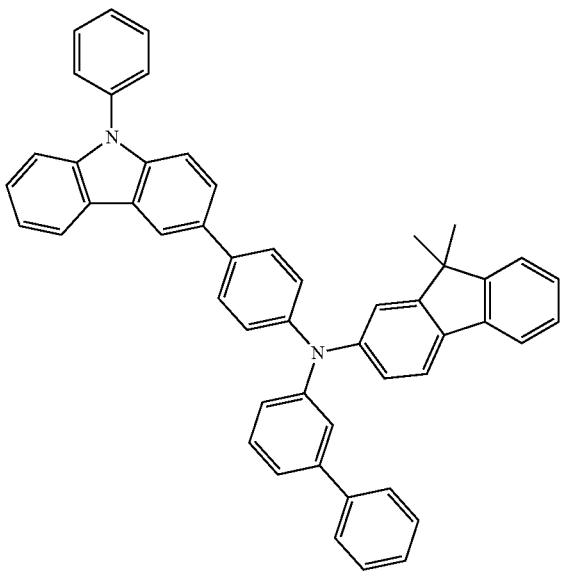

HT3

77
-continued
78
-continued
HT4
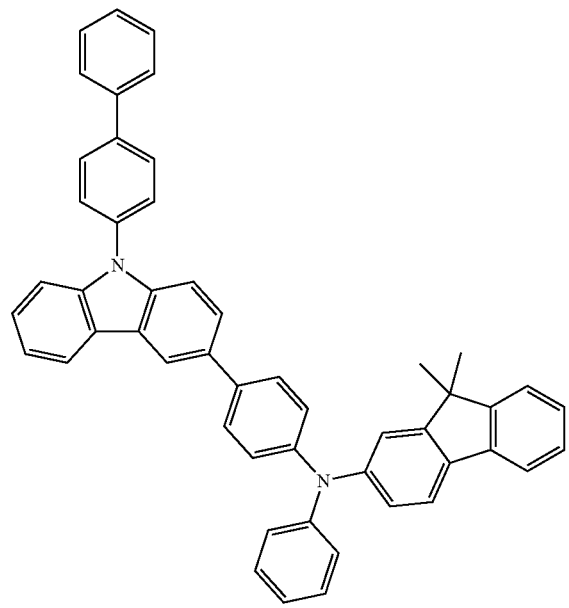
HT6
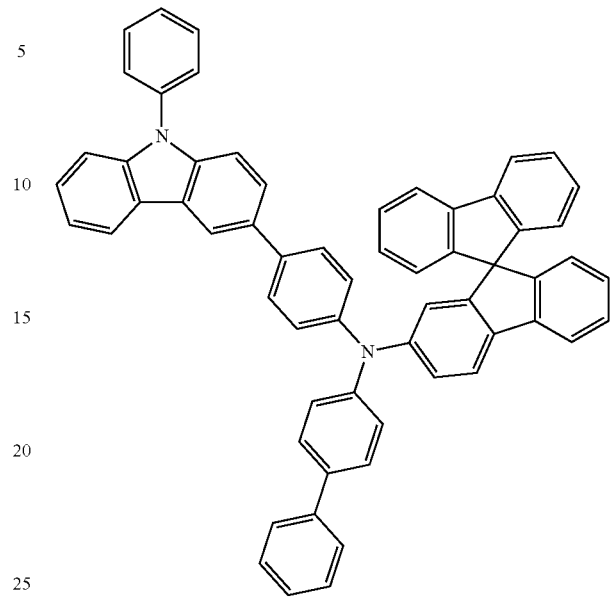
HT5
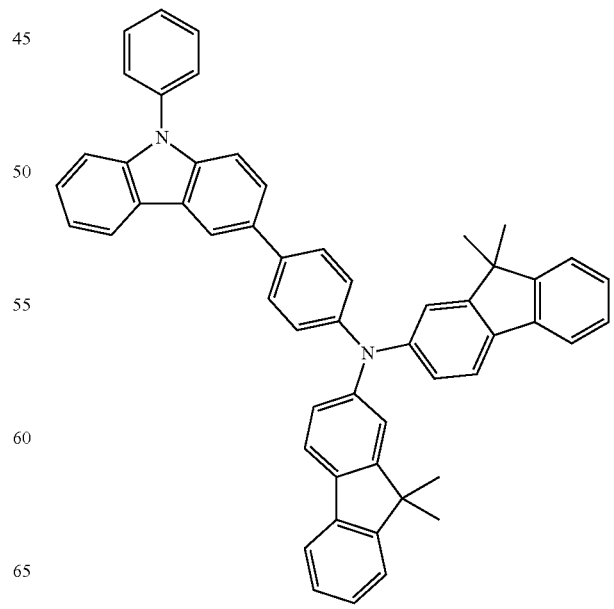
HT7

HT8
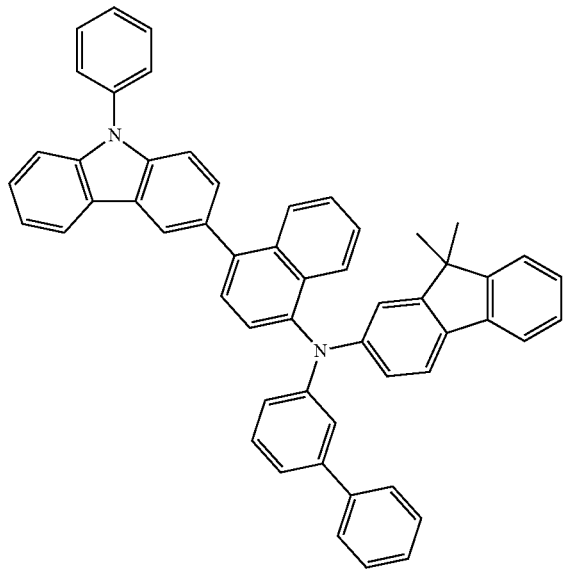
HT10
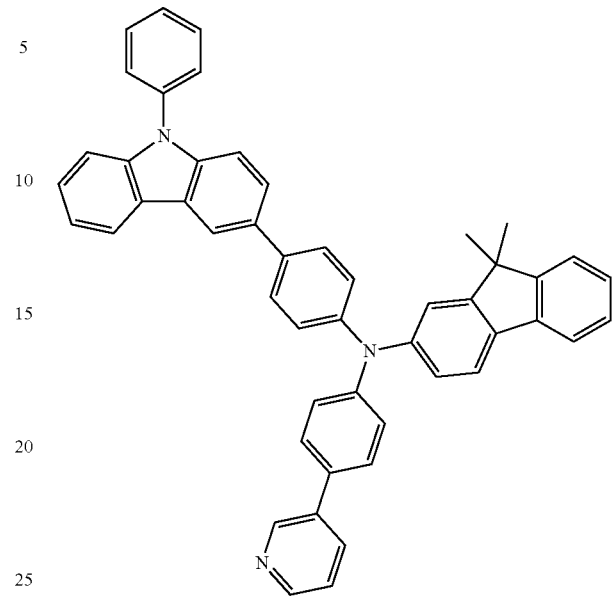
HT9
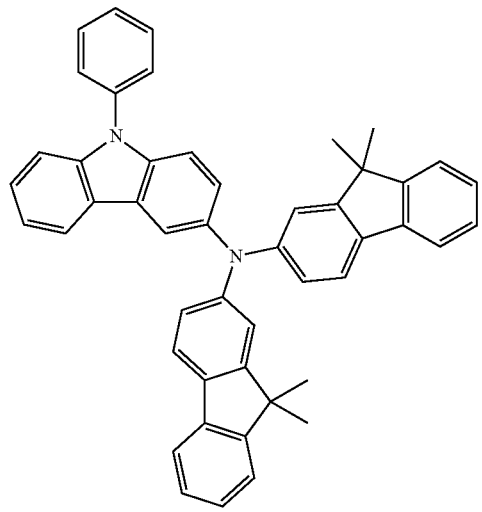
HT11

HT12
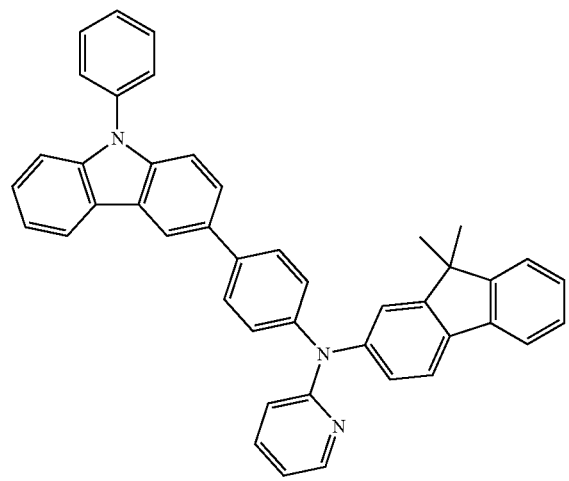
HT13
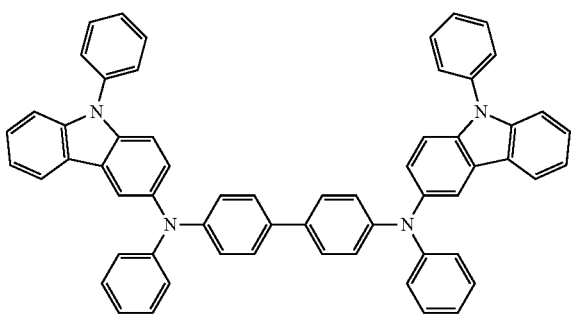
HT14
HT15
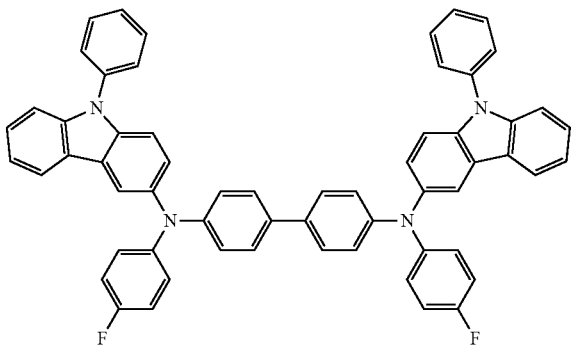
HT16
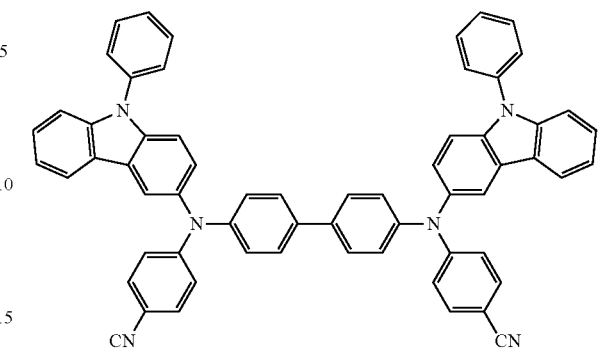
HT17
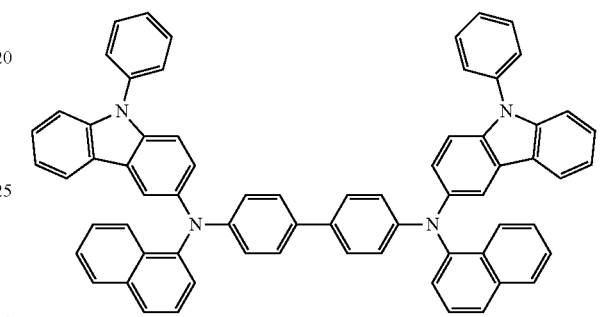
HT18
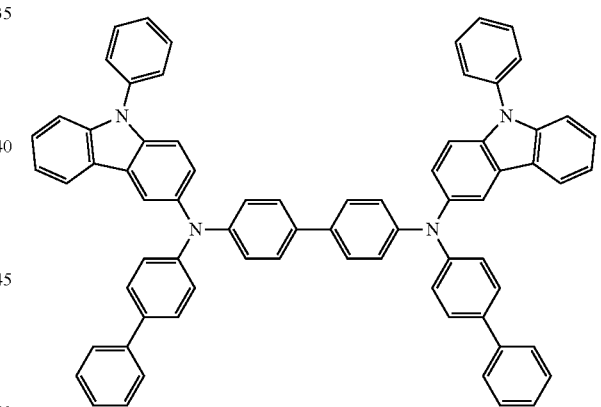
HT19
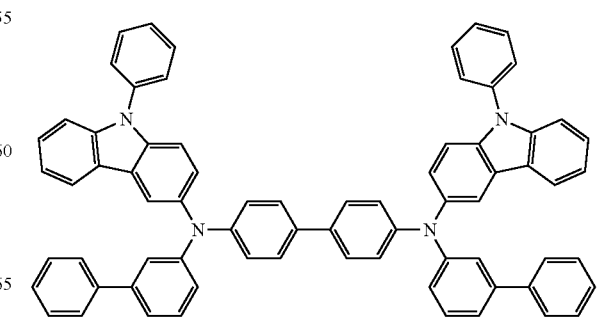

HT20

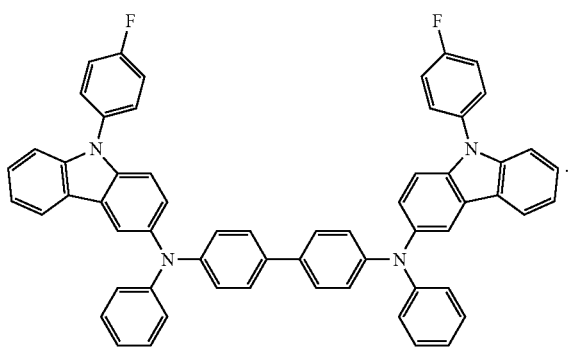

A thickness of the hole transport region may be in a range of about 100 Å to about 10,000 Å, for example, about 100 Å to about 1,000 Å. When the hole transport region includes at least one selected from a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example, about 100 Å to about 1,500 Å. When the thicknesses of the hole transport region, the hole injection layer, and the hole transport layer are within any of these ranges, satisfactory (or suitable) hole transporting characteristics may be obtained without a substantial increase in driving voltage.

The hole transport region may further include, in addition to the materials described above, a charge-generation material for the improvement of conductive properties. The charge-generation material may be homogeneously or unhomogeneously dispersed in the hole transport region.

The charge-generation material may be, for example, a p-dopant. The p-dopant may be one selected from a quinone derivative, a metal oxide, and a cyano group-containing compound, but embodiments are not limited thereto. Non-limiting examples of the p-dopant include quinone derivatives (such as tetracyanoquinonedimethane (TCNQ) and/or 2,3,5,6-tetrafluoro-tetracyano-1,4-benzoquinonedimethane (F4-TCNQ)), metal oxides (such as tungsten oxide and/or molybdenum oxide), and Compound HT-D1 illustrated below.

Compound HT-D1

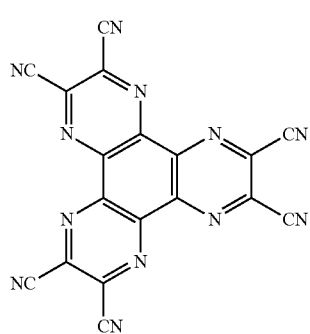

F4-TCNQ

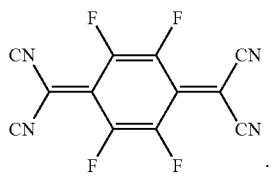

The hole transport region may further include, in addition to the hole injection layer and/or the hole transport layer, at least one selected from a buffer layer and an electron blocking layer. Since the buffer layer may compensate for an optical resonance distance according to a wavelength of light emitted from the emission layer, light-emission efficiency of the formed organic light-emitting device may be improved. For use as a material included in the buffer layer, any of materials that are to be included in the hole transport region may be used. The electron blocking layer may function to prevent or reduce the injection of electrons from the electron transport region.

An emission layer may be formed on the first electrode 110 or the hole transport region by using one or more suitable methods such as vacuum deposition, spin coating, casting, a LB method, ink-jet printing, laser-printing, and/or laser-induced thermal imaging. When an emission layer is formed by vacuum deposition and/or spin coating, deposition and coating conditions for the emission layer may be the same as (or similar to) those for the hole injection layer.

When the organic light-emitting device 10 is a full color organic light-emitting device, the emission layer may be patterned into a red emission layer, a green emission layer, and/or a blue emission layer, according to a sub pixel. In some embodiments, the emission layer may have a stacked structure including a red emission layer, a green emission layer, and a blue emission layer, or may include a red-light emission material, a green-light emission material, and a blue-light emission material, which are mixed with each other in a single layer, to emit white light.

The emission layer may include a host and a dopant.

The host may include at least one selected from TPBi, TBADN, ADN (herein also referred to as "DNA"), CBP, CDBP, and TCP:

TPBi

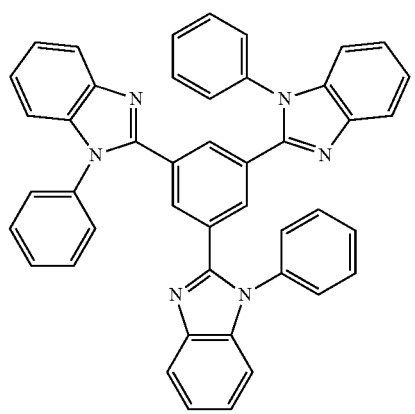

-continued

TBADN

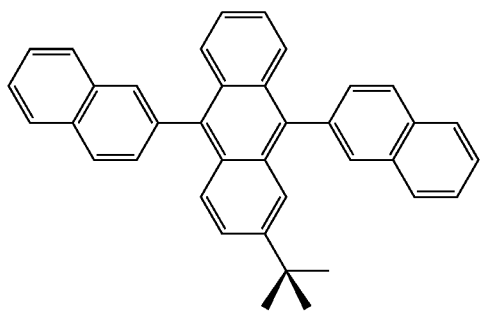

ADN

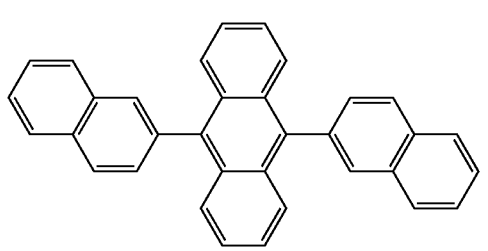

CBP

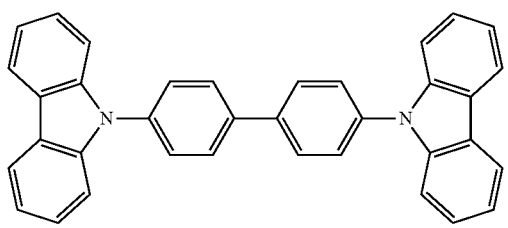

CDBP

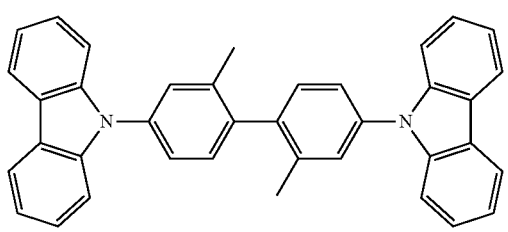

TCP

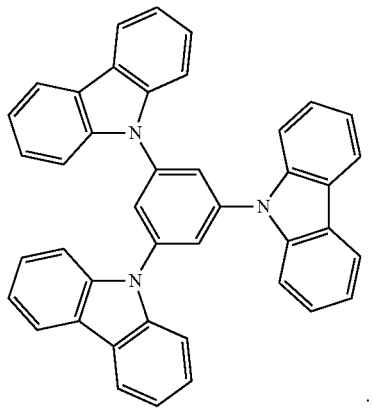

In some embodiments, the host may include a compound represented by Formula 301 below.

$$Ar_{301}\text{-}[(L_{301})_{xb1}\text{-}R_{301}]_{xb2}.$$  Formula 301

In Formula 301, $Ar_{301}$ may be selected from the group consisting of:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, and a naphthalene group, a heptalene group, a fluorene group, a spiro-fluorene group, a benzofluorene group, a dibenzofluorene group, a phenalene group, a phenanthrene group, a anthracene group, a fluoranthene group, a triphenylene group, a pyrene group, a chrysene group, a naphthacene group, a picene group, a perylene group, a pentaphene group, and an indenoanthracene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (wherein $Q_{301}$ to $Q_{303}$ may each independently be selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group);

description of $L_{301}$ may be the same as the description provided in connection with $L_1$;

$R_{301}$ may be selected from the group consisting of:

a $C_1$-$C_{20}$ alkyl group and a $C_1$-$C_{20}$ alkoxy group, a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 may be selected from 0, 1, 2, and 3; and xb2 may be selected from 1, 2, 3, and 4.

For example, in Formula 301, $L_{301}$ may be selected from the group consisting of:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

$R_{301}$ may be selected from the group consisting of:

a $C_1$-$C_{20}$ alkyl group and a $C_1$-$C_{20}$ alkoxy group, a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, but embodiments of the present disclosure are not limited thereto.

For example, the host may include a compound represented by Formula 301A below:

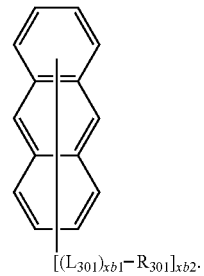

Formula 301A $[(L_{301})_{xb1}-R_{301}]_{xb2}$.

Descriptions of substituents of Formula 301A may be understood by referring to the descriptions thereof provided herein.

The compound represented by Formula 301 may include at least one of Compounds H1 to H42, but is not limited thereto:

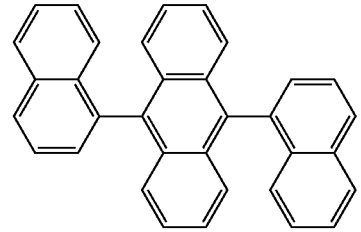

H1

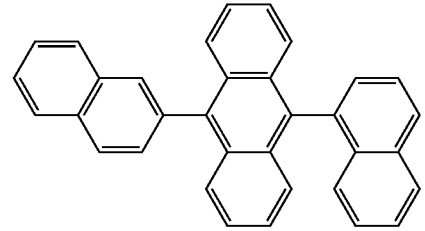

H2

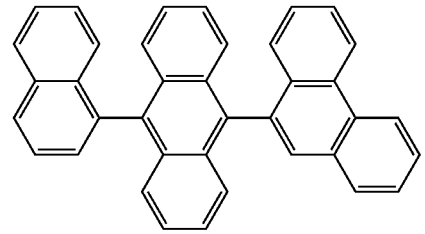

H3

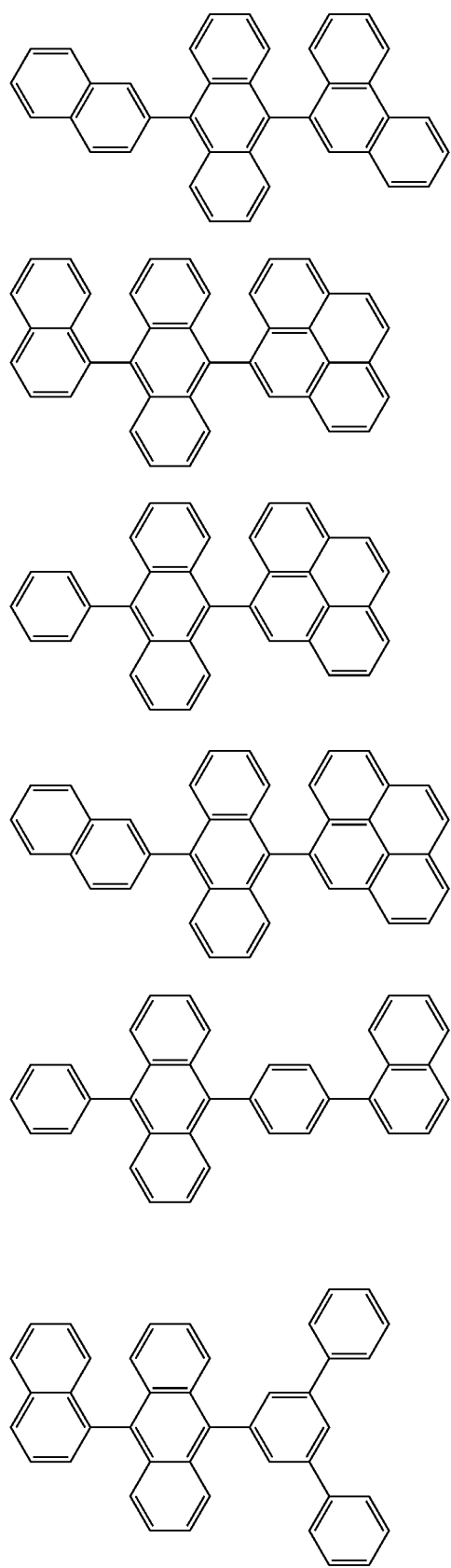

-continued
H16
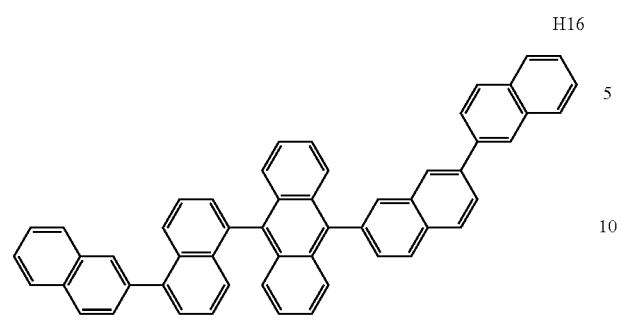
H17
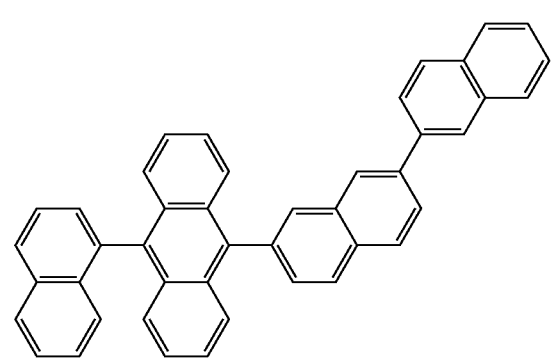
H18
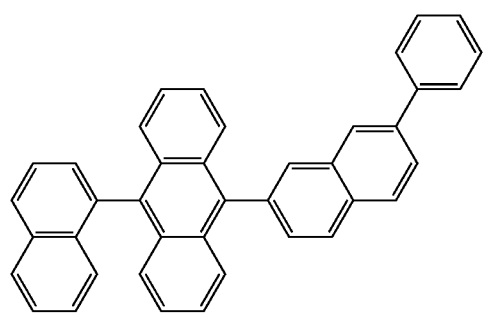
H19
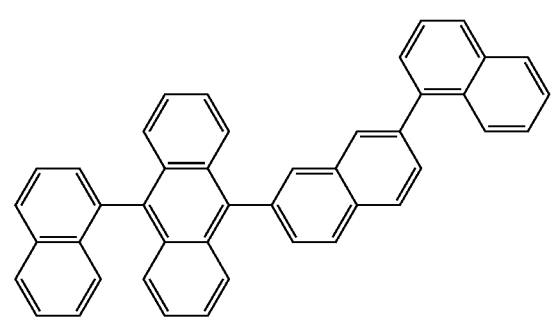
-continued
H20
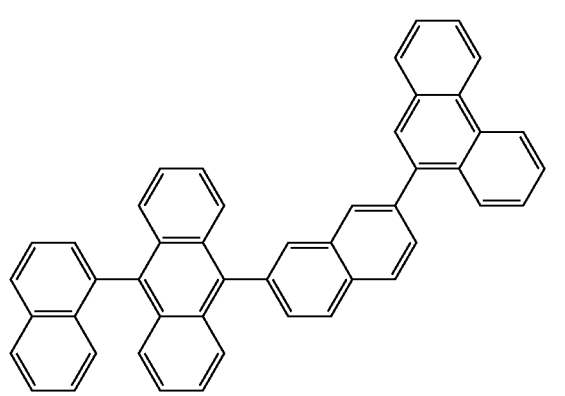
H21
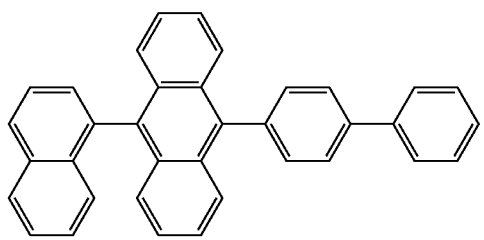
H22
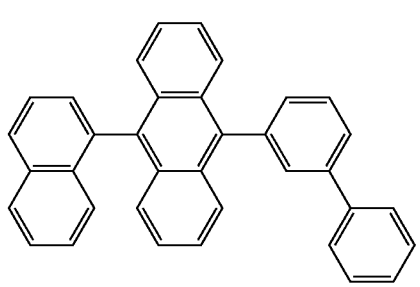
H23
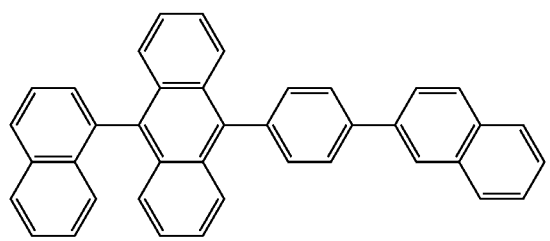
H24
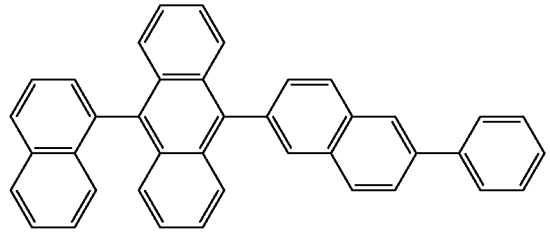

-continued
H25
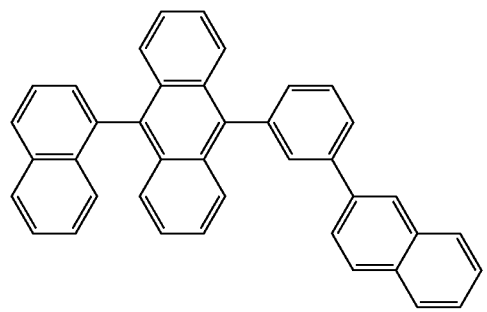
H26
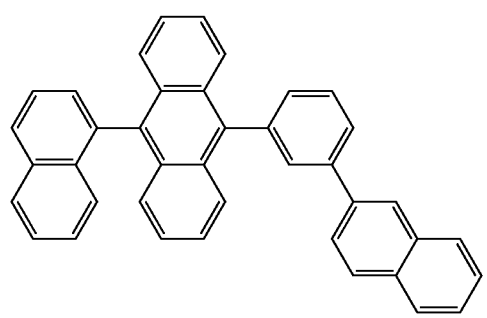
H27
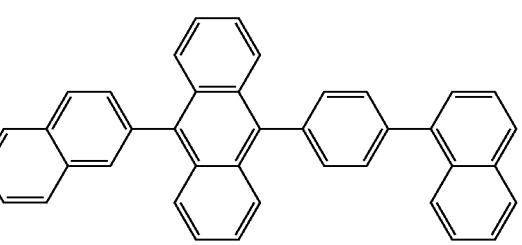
H28
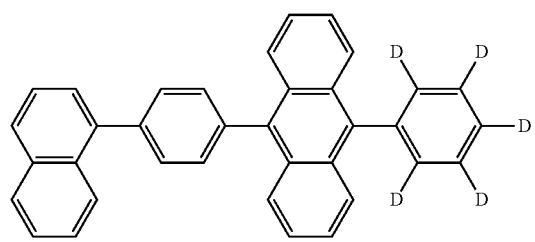
H29
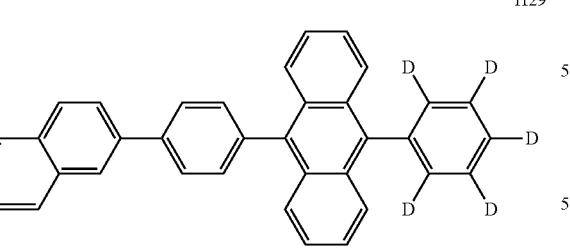
H30
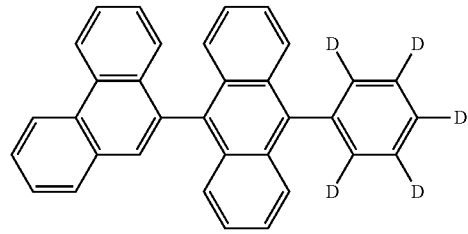
-continued
H31
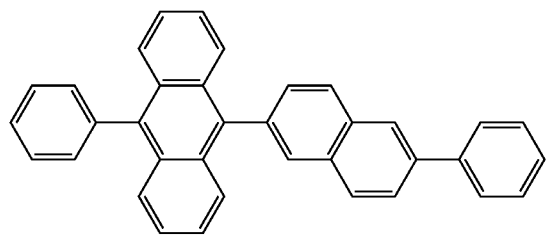
H32
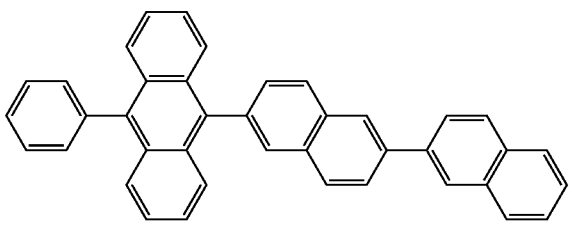
H33
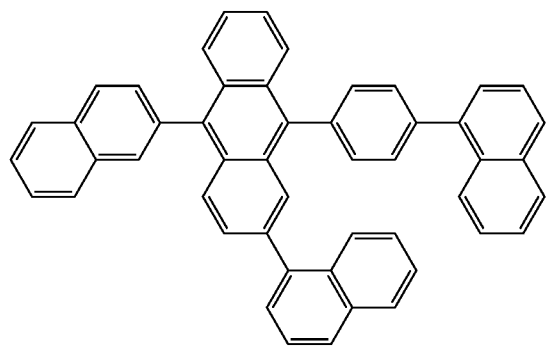
H34
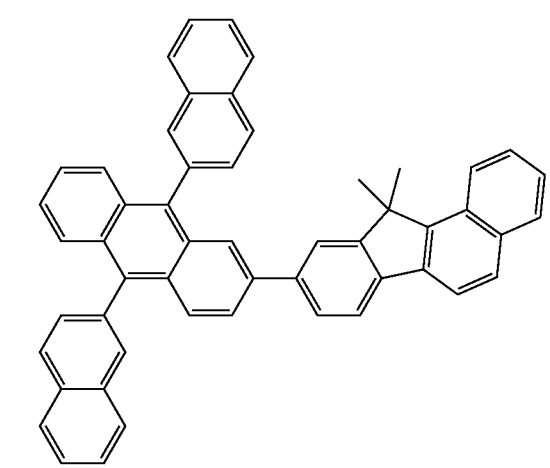

H35
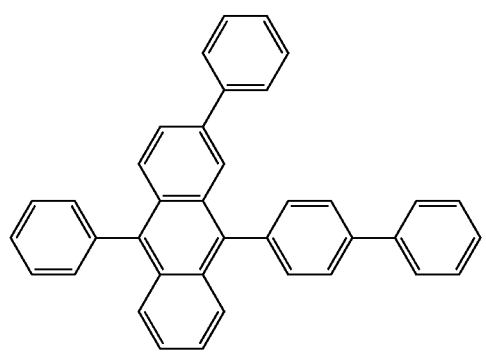
H36
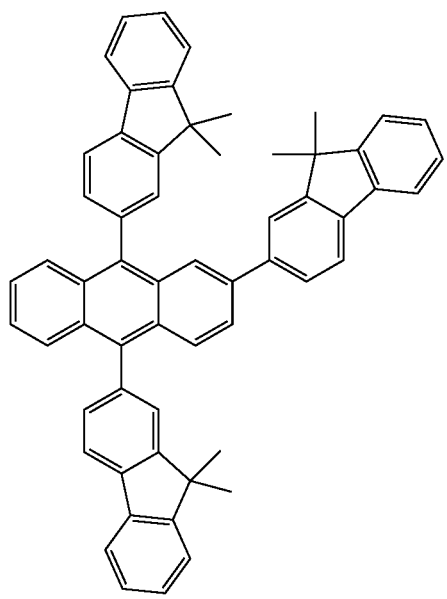
H37
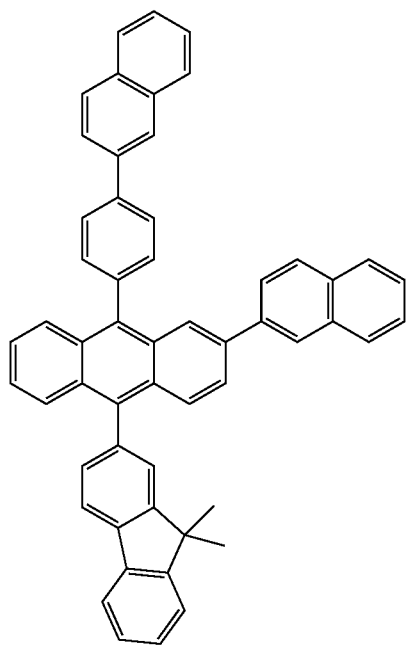
H38
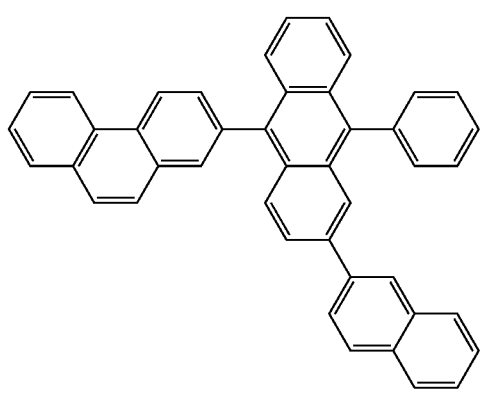
H39
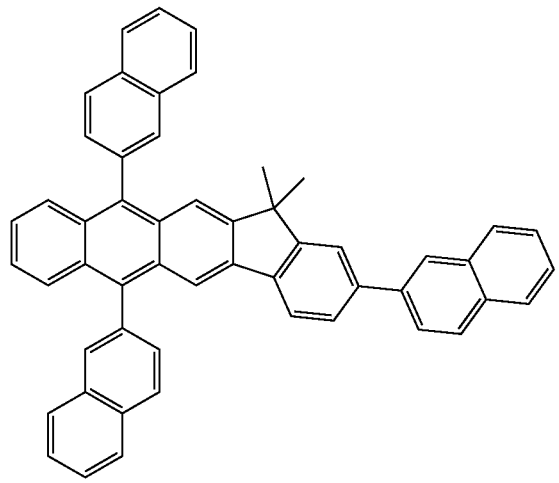
H40
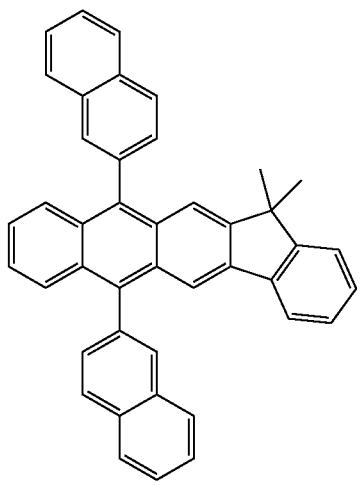

H41
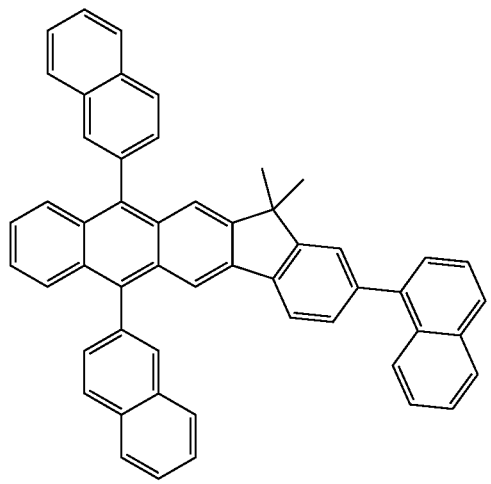
H42
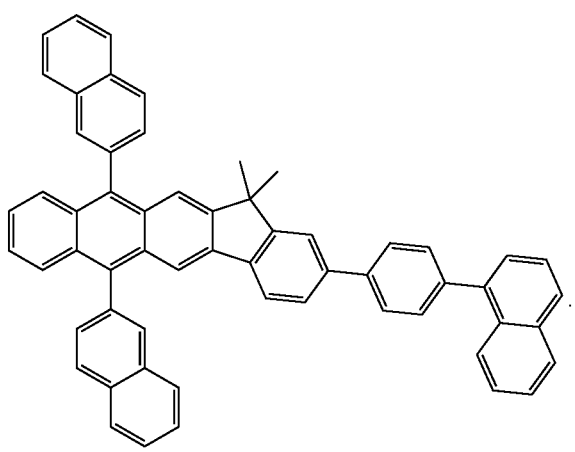
H44
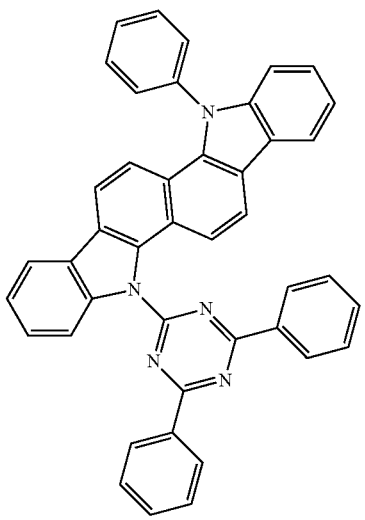
H45
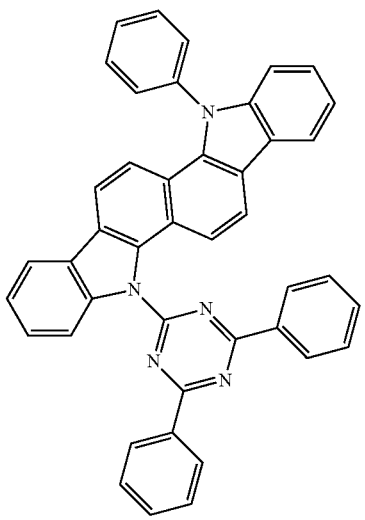
In some embodiments, the host may include at least one of Compounds H43 to H49 below, but is not limited thereto:
H43
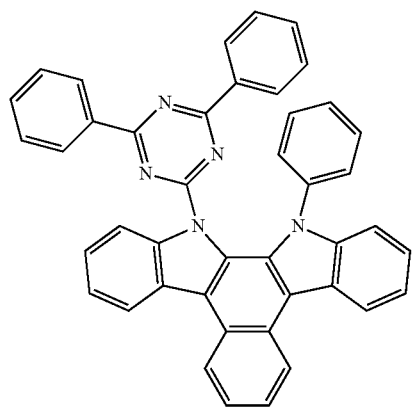
H46
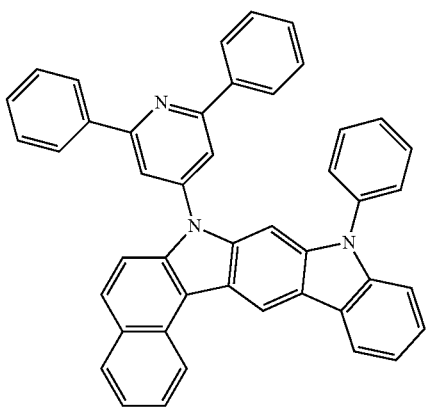

H47

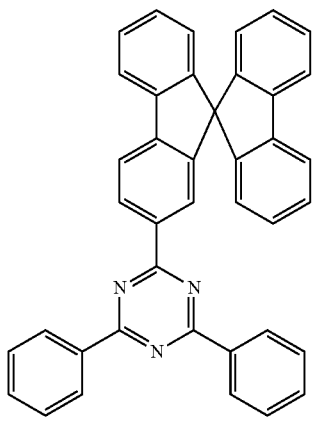

H48

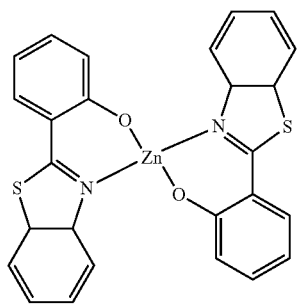

H49

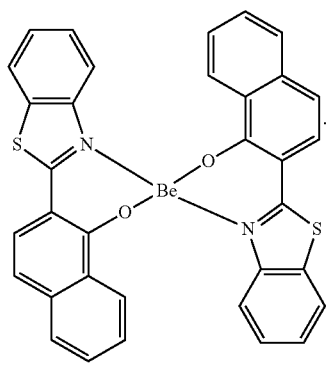

The dopant may include at least one selected from a fluorescent dopant and a phosphorescent dopant.

For example, the phosphorescent dopant may include an organometallic compound including one selected from iridium (Ir), platinum (Pt), osmium (Os), titanium (Ti), zirconium (Zr), hafnium (Hf), europium (Eu), terbium (Tb), thulium (Tm), rhodium (Rh), and copper (Cu).

In some embodiments, the phosphorescent dopant may include an organometallic complex represented by Formula 401 below:

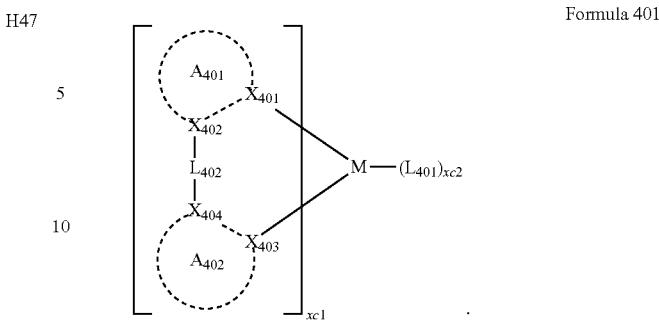

Formula 401

In Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may each independently be nitrogen or carbon;

$A_{401}$ and $A_{402}$ rings may each independently be selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene; and at least one substituent of the substituted benzene, substituted naphthalene, substituted fluorene, substituted spiro-fluorene, substituted indene, substituted pyrrole, substituted thiophene, substituted furan, substituted imidazole, substituted pyrazole, substituted thiazole, substituted isothiazole, substituted oxazole, substituted isoxazole, substituted pyridine, substituted pyrazine, substituted pyrimidine, substituted pyridazine, substituted quinoline, substituted isoquinoline, substituted benzoquinoline, substituted quinoxaline, substituted quinazoline, substituted carbazole, substituted benzoimidazole, substituted benzofuran, substituted benzothiophene, substituted isobenzothiophene, substituted benzoxazole, substituted isobenzoxazole, substituted triazole, substituted oxadiazole, substituted triazine, substituted dibenzofuran, and substituted dibenzothiophene may be selected from the group consisting of:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{401}$)($Q_{402}$), —Si($Q_{403}$)($Q_{404}$)($Q_{405}$), or —B($Q_{406}$)($Q_{407}$), a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkenyl group, a $C_1$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$), and —B($Q_{416}$)($Q_{417}$), and —N($Q_{421}$)($Q_{422}$), —Si($Q_{423}$)($Q_{424}$)($Q_{425}$), and —B($Q_{426}$)($Q_{427}$), where descriptions of $Q_{401}$ to $Q_{407}$, $Q_{411}$ to $Q_{417}$, and $Q_{421}$ to $Q_{427}$ may each independently be understood by referring to the description provided in connection with $Q_1$;

$L_{401}$ may be an organic ligand;

xc1 may be 1, 2, or 3; and xc2 may be 0, 1, 2, or 3.

$L_{401}$ may be a monovalent, divalent, or trivalent organic ligand. For example, $L_{401}$ may be selected from a halogen ligand (e.g., Cl and/or F), a diketone ligand (e.g., acetylacetonate, 1,3-diphenyl-1,3-propanedionate, 2,2,6,6-tetramethyl-3,5-heptanedionate, and/or hexafluoroacetonate), a carboxylic acid ligand (e.g., picolinate, dimethyl-3-pyrazolecarboxylate, and/or benzoate), a carbon monooxide ligand, an isonitrile ligand, a cyano ligand, and a phosphorous ligand (e.g., phosphine and/or phosphite), but is not limited thereto.

When $A_{401}$ in Formula 401 has two or more substituents, the substituents of $A_{401}$ may be linked to form a saturated or unsaturated ring.

When $A_{402}$ in Formula 401 has two or more substituents, the substituents of $A_{402}$ may be linked to form a saturated or unsaturated ring.

When xc1 in Formula 401 is two or more, a plurality of ligands

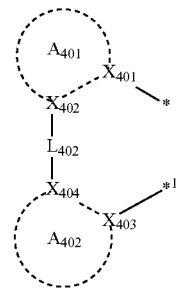

in Formula 401 may be identical to or different from each other. When xc1 in Formula 401 is two or more, $A_{401}$ and $A_{402}$ of one ligand may each independently be connected to respective $A_{401}$ and $A_{402}$ of other neighboring ligands, either directly (e.g., via a bond such as a single bond) or with a linker (e.g., a $C_1$-$C_5$ alkylene group, —N(R')— (wherein R' may be a $C_1$-$C_{10}$ alkyl group or a $C_6$-$C_{20}$ aryl group) and/or —C(=O)— therebetween.

The phosphorescent dopant may include at least one selected from Compounds PD1 to PD74 below, but is not limited thereto:

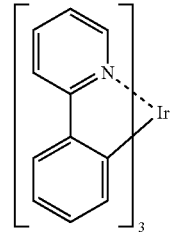

PD1

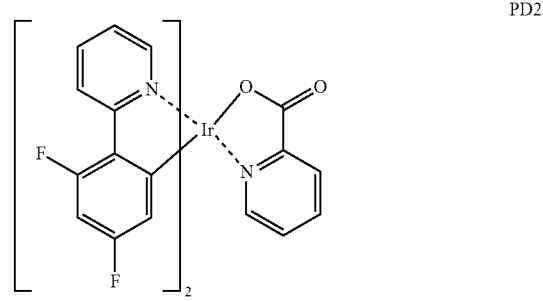

PD2

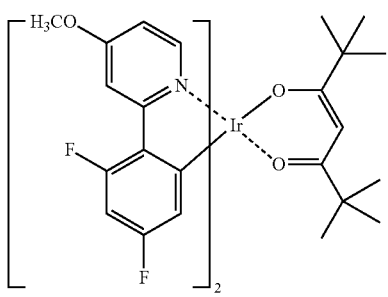PD3
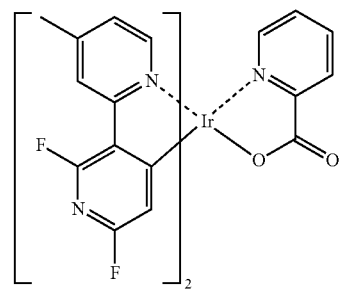PD8
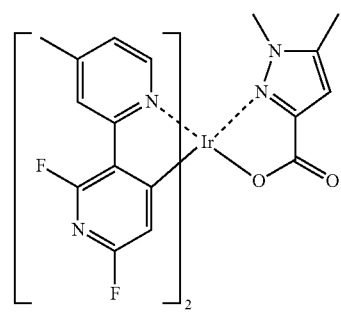PD9
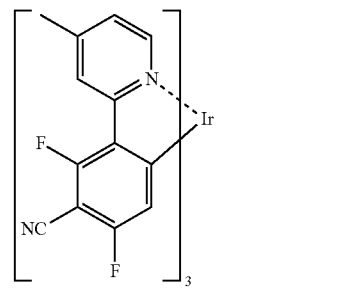PD10
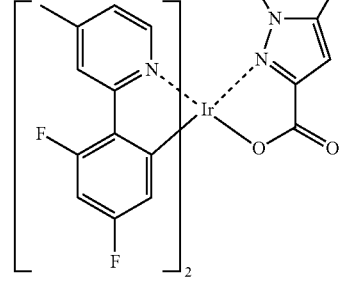PD11
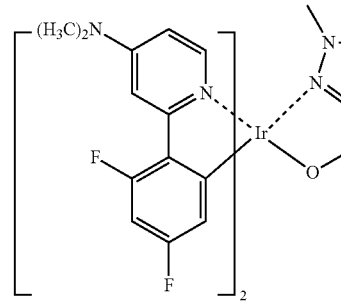PD12
PD4
PD5
PD6
PD7

PD13 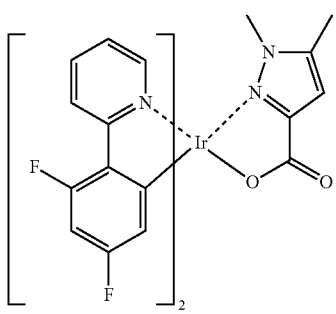
PD14 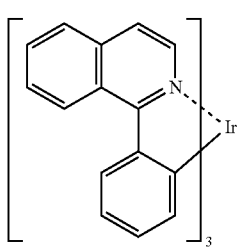
PD15 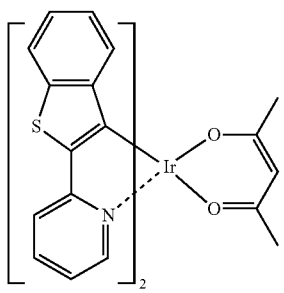
PD16 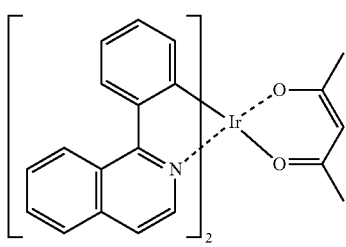
PD17 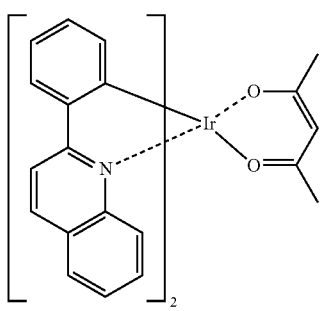
PD18 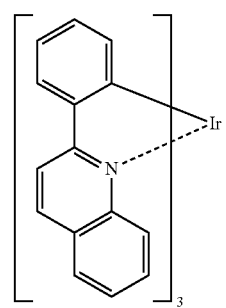
PD19 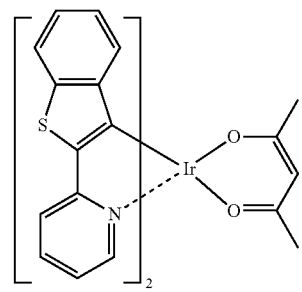
PD20 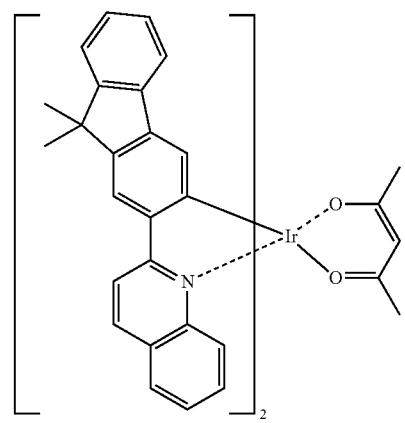
PD21 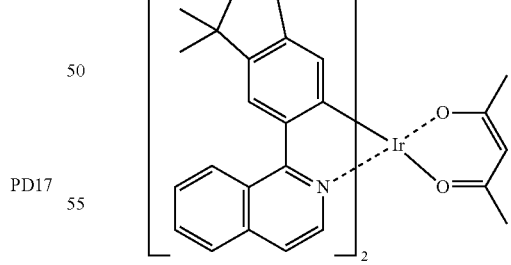
PD22 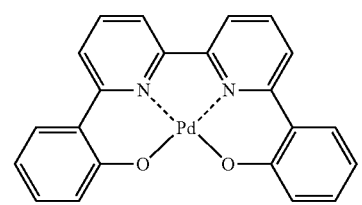

PD23
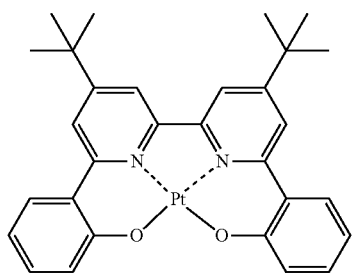
PD24
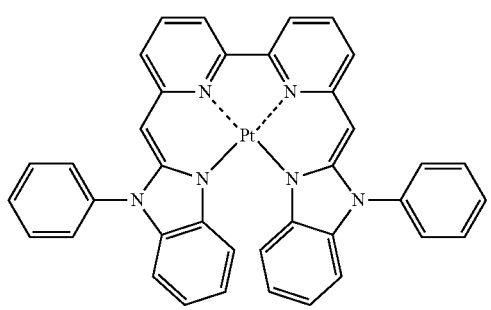
PD25
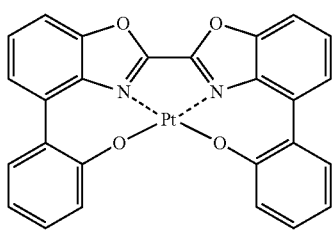
PD26
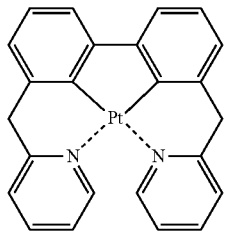
PD27
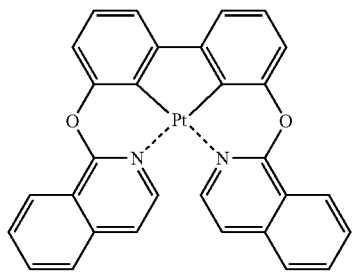
PD28
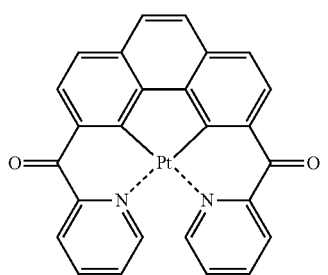
PD29
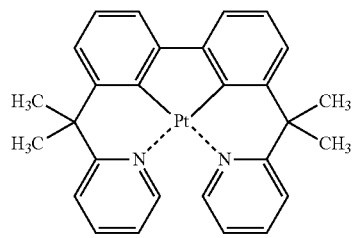
PD30
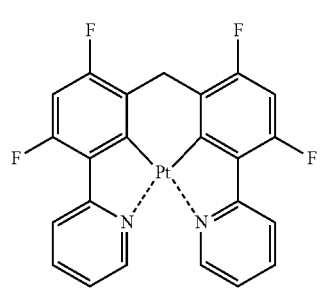
PD31
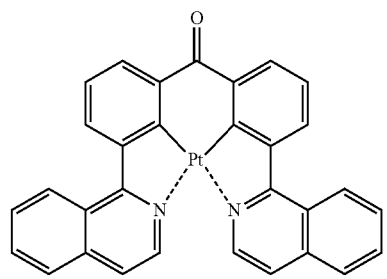
PD32
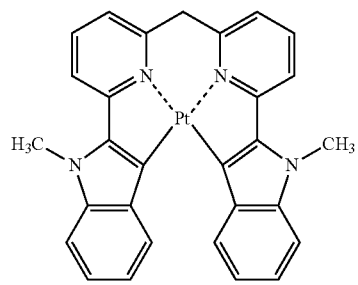
PD33
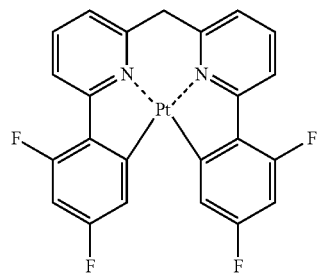
PD34
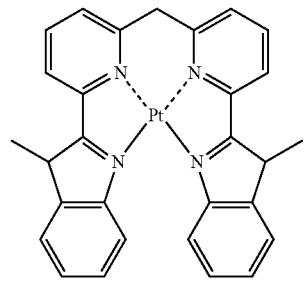

-continued
PD35 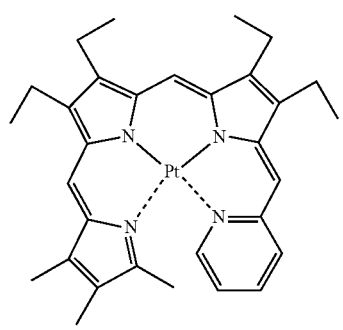
PD36 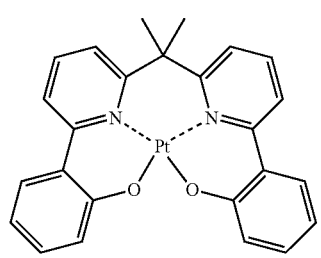
PD37 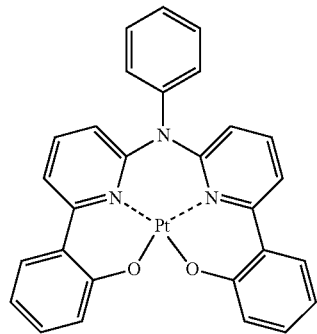
PD38 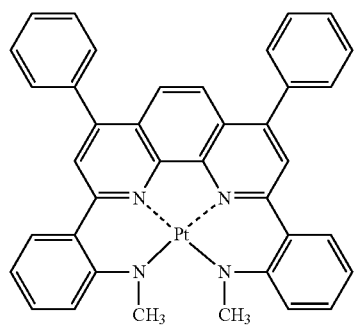
PD39 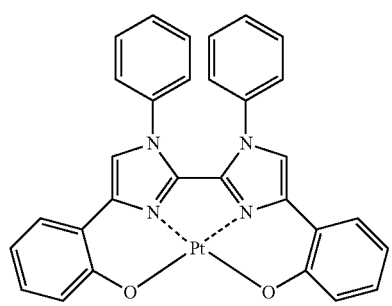
-continued
PD40 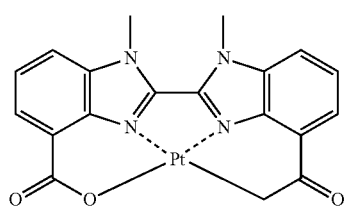
PD41 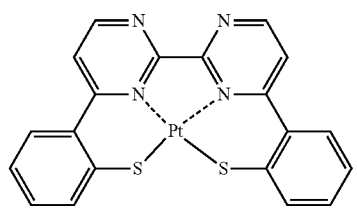
PD42 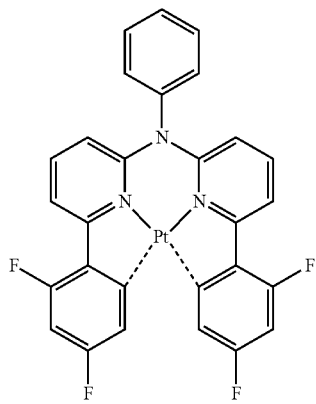
PD43 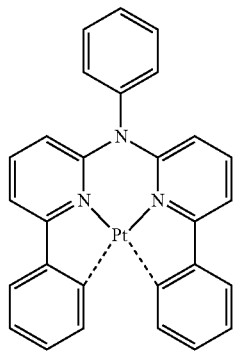
PD44 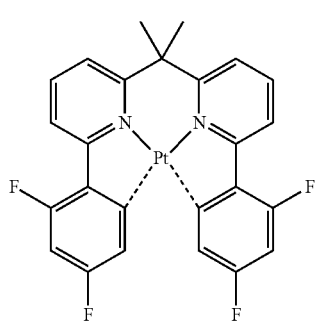

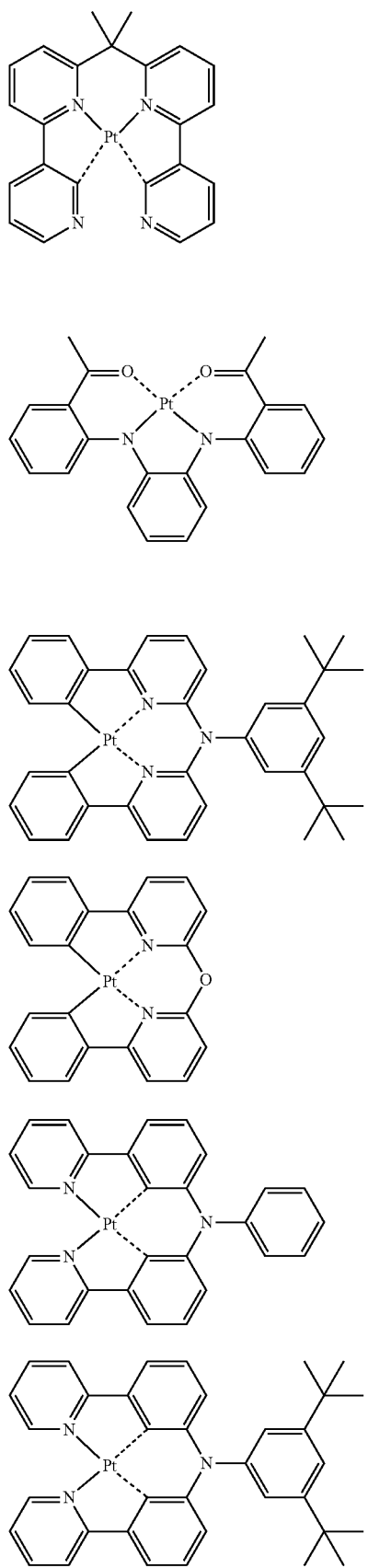
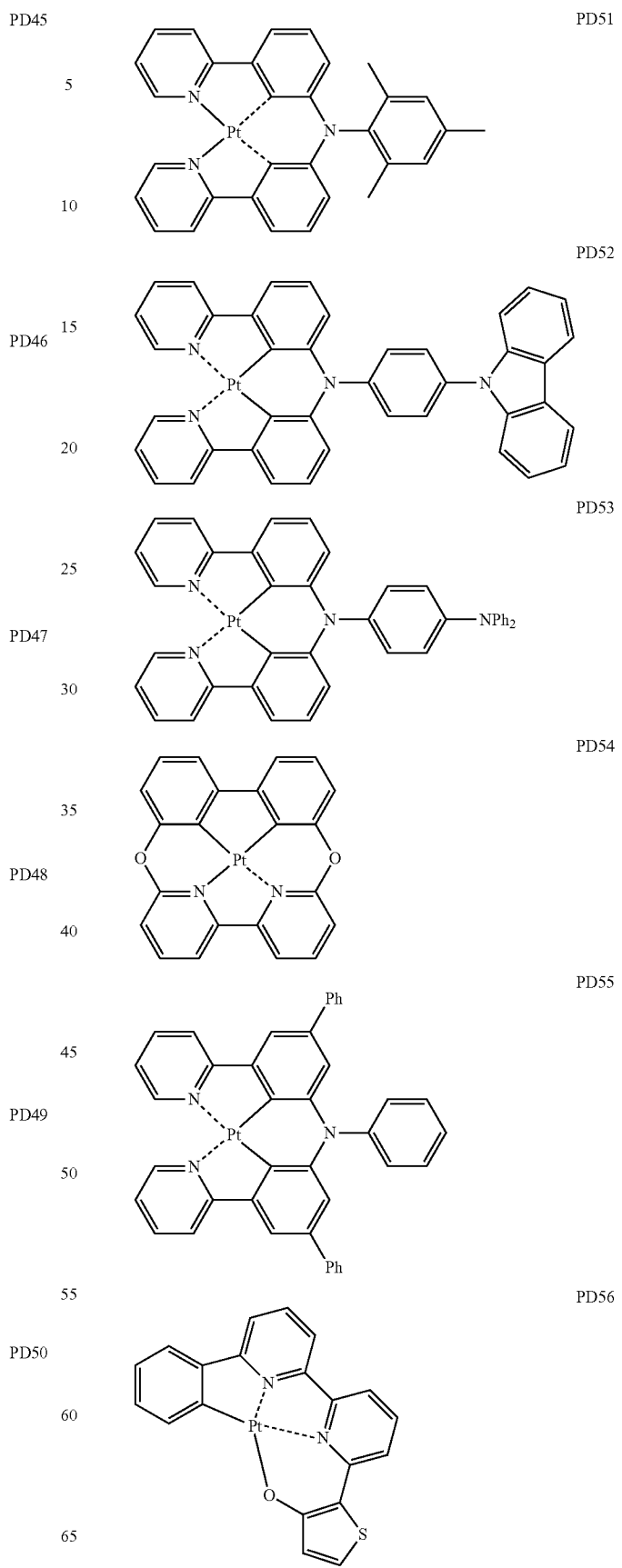

PD57
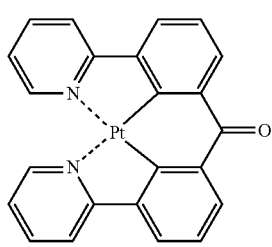
PD58
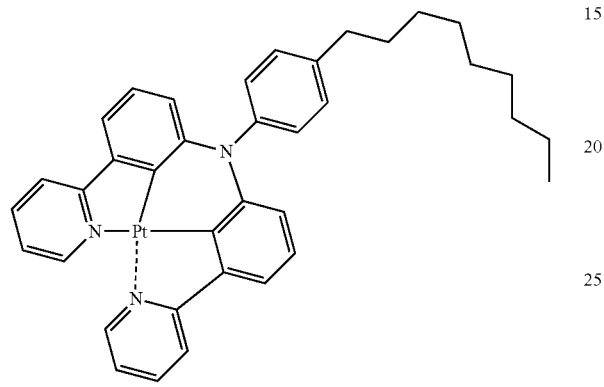
PD59
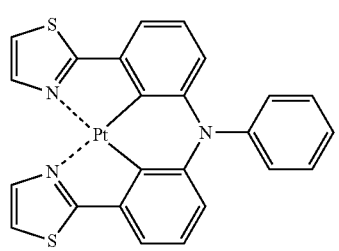
PD60
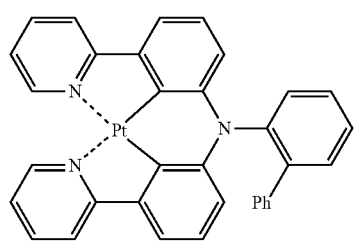
PD61
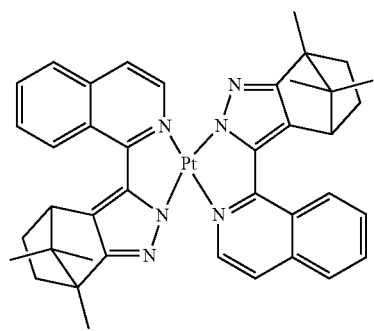
PD62
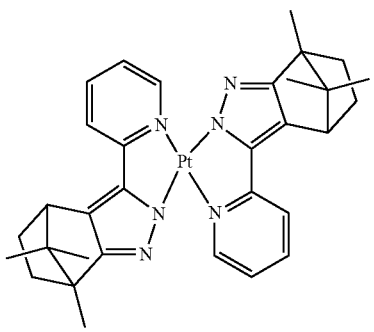
PD63
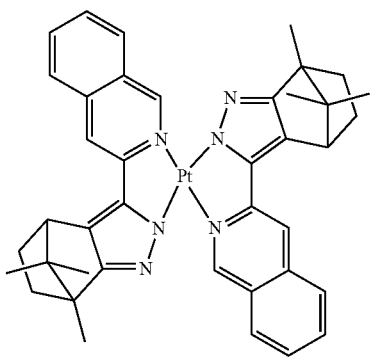
PD64
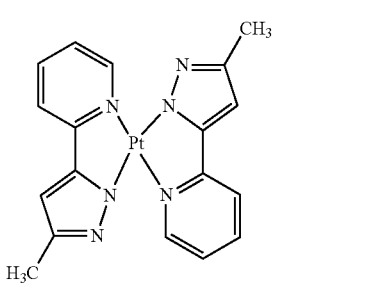
PD65
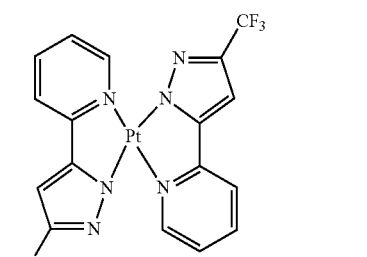
PD66
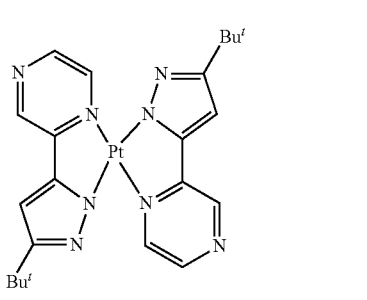

-continued
PD67
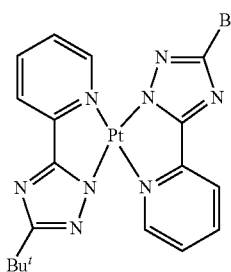
PD68
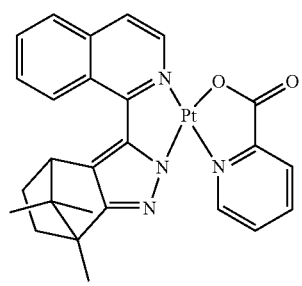
PD69
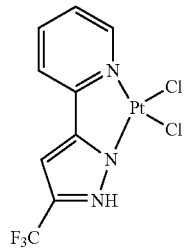
PD70
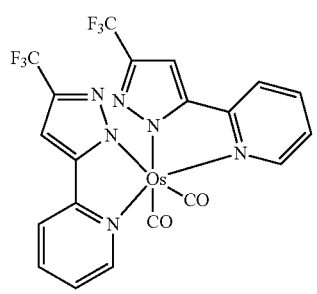
PD71
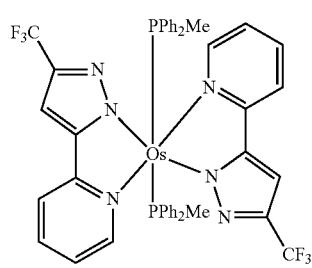
PD72
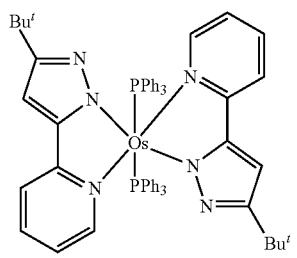
PD73
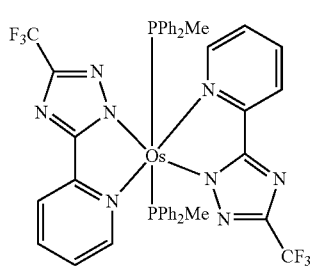
PD74
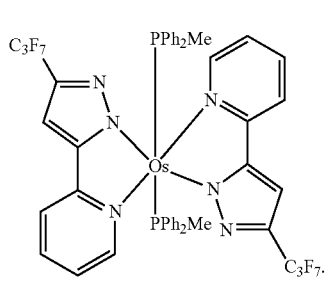
In some embodiments, the phosphorescent dopant may include PtOEP:
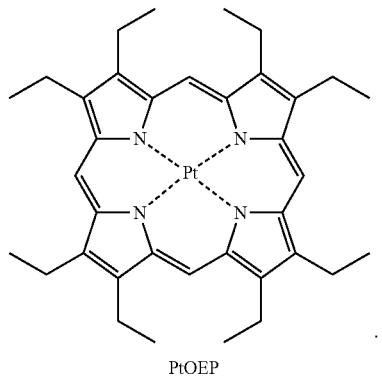
PtOEP
The fluorescent dopant may include at least one selected from DPVBi, DPAVBi TBPe, DCM, DCJTB, Coumarin 6, and C545T.

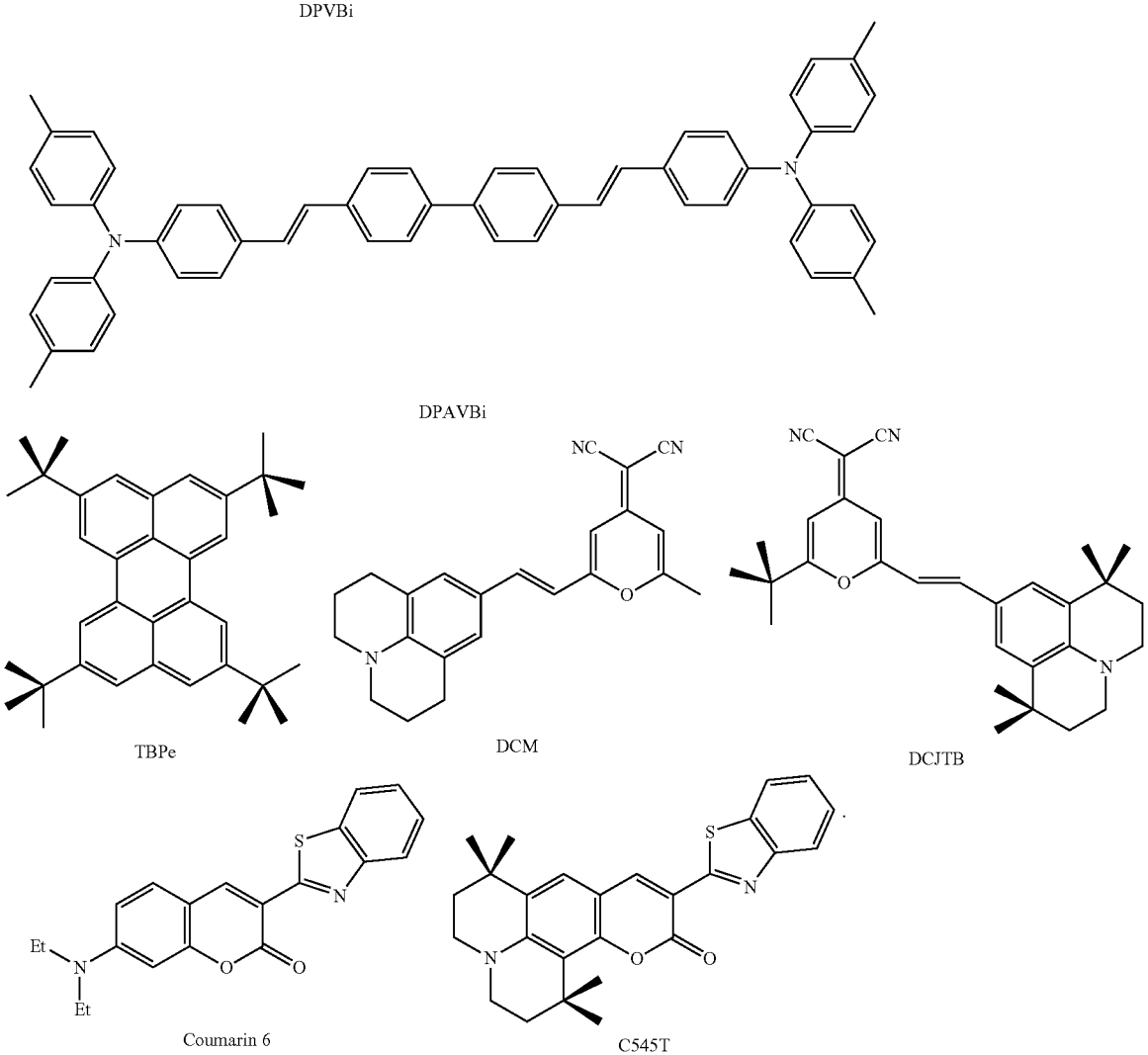

In some embodiments, the fluorescent dopant may include a compound represented by Formula 501 below.

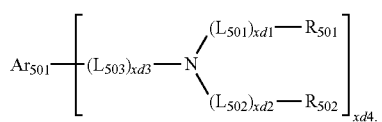

Formula 501

In Formula 501, $Ar_{501}$ may be selected from the group consisting of:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, and a naphthalene group, a heptalene group, a fluorene group, a spiro-fluorene group, a benzofluorene group, a dibenzofluorene group, a phenalene group, a phenanthrene group, a anthracene group, a fluoranthene group, a triphenylene group, a pyrene group, a chrysene group, a naphthacene group, a picene group, a perylene group, a pentaphene group, and an indenoanthracene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$) (wherein $Q_{501}$ to $Q_{503}$ may each independently be selected from hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group);

descriptions of $L_{501}$ to $L_{503}$ may each independently be understood by referring to the description of $L_{201}$;

$R_{501}$ and $R_{502}$ may each independently be selected from the group consisting of:

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group and a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group;

xd1 to xd3 may each independently be selected from 0, 1, 2, and 3; and xd4 may be selected from 1, 2, 3, and 4.

The fluorescent dopant may include at least one of Compounds FD1 to FD9:

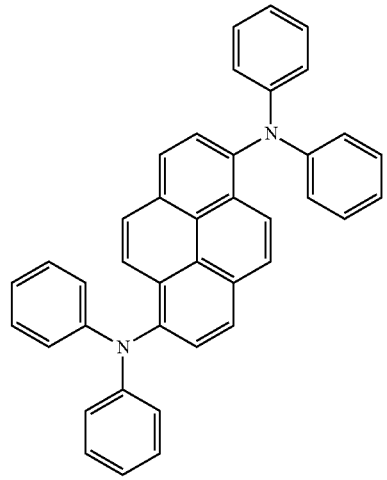

FD1

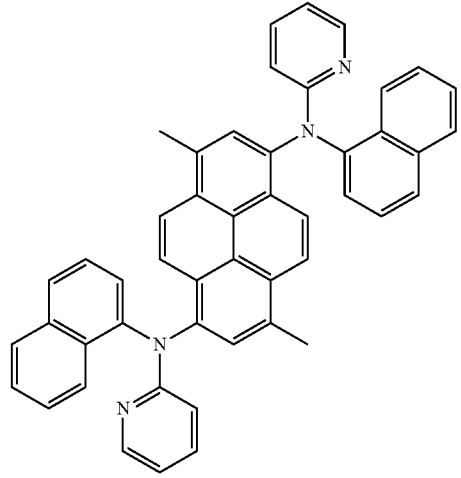

FD2

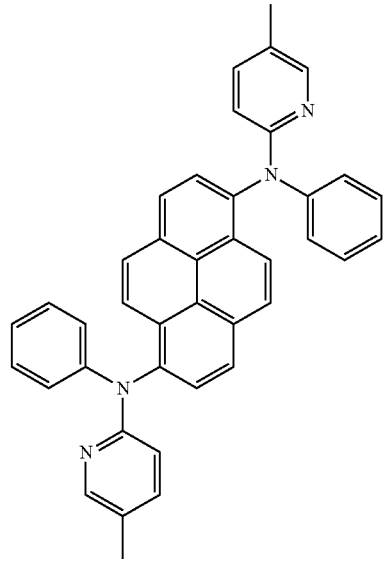

FD3

-continued

FD4

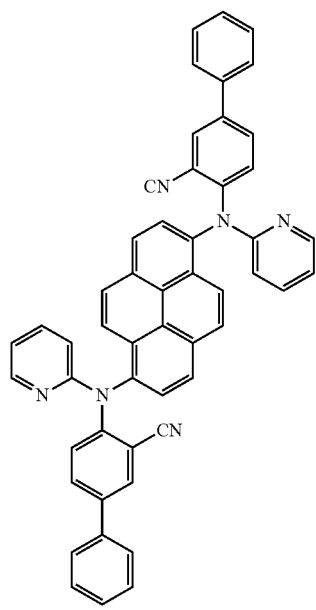

FD5

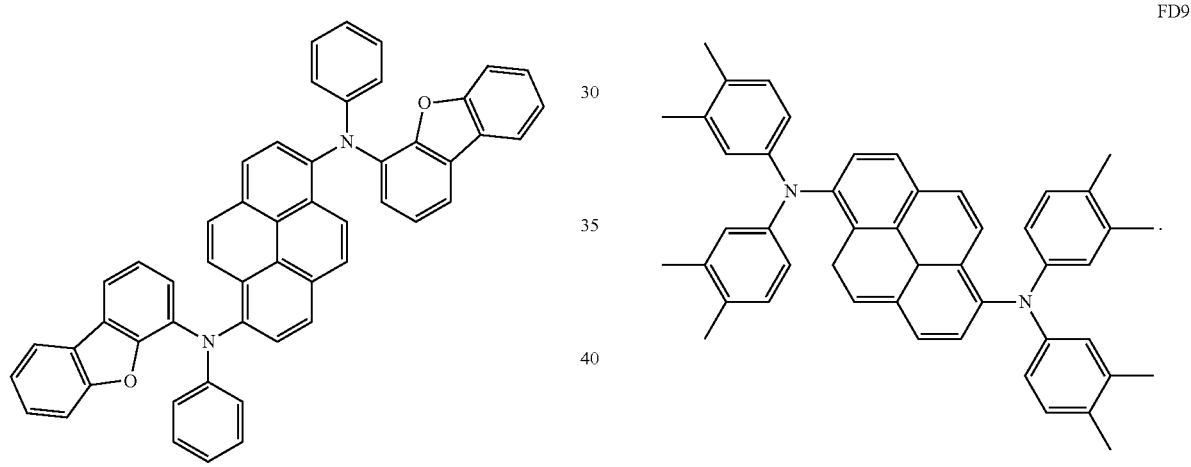

FD7

FD8

FD9

FD6

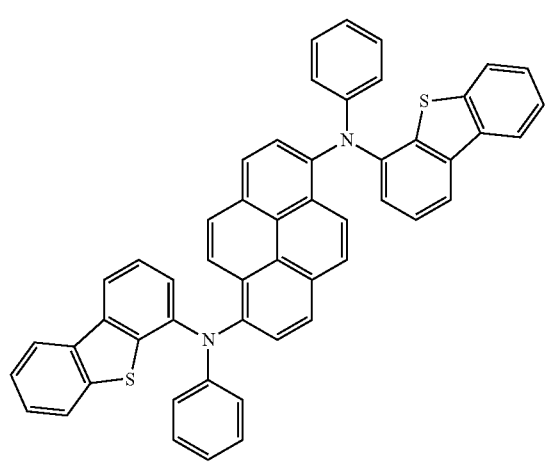

An amount of the dopant in the emission layer may be, for example, in a range of about 0.01 to about 15 parts by weight based on 100 parts by weight of the host, but is not limited thereto.

A thickness of the emission layer may be in a range of about 100 Å to about 1,000 Å, for example, about 200 Å to about 600 Å. When the thickness of the emission layer is within any of these ranges, excellent (or suitable) light-emission characteristics may be obtained without a substantial increase in driving voltage.

An electron transport region may be disposed on the emission layer.

The electron transport region may include at least one selected from a hole blocking layer, an electron transport layer (ETL), and an electron injection layer, but is not limited thereto.

For example, the electron transport region may have a structure of electron transport layer/electron injection layer or a structure of hole blocking layer/electron transport layer/electron injection layer, wherein the layers of each structure are sequentially stacked in a direction from the emission layer in the stated order, but the structure of the electron transport region is not limited thereto.

According to an embodiment, the organic layer 150 of the organic light-emitting device may include an electron transport region between the emission layer and the second electrode 190.

When the electron transport region includes a hole blocking layer, the hole blocking layer may be formed on the emission layer by using one or more suitable methods such as vacuum deposition, spin coating, casting, a Langmuir-Blodgett (LB) method, ink-jet printing, laser-printing, and/or laser-induced thermal imaging. When the hole blocking layer is formed by vacuum deposition and/or spin coating, deposition and coating conditions for the hole blocking layer may be determined by referring to the deposition and coating conditions for the hole injection layer.

The hole blocking layer may include, for example, at least one selected from BCP and Bphen, but is not limited thereto.

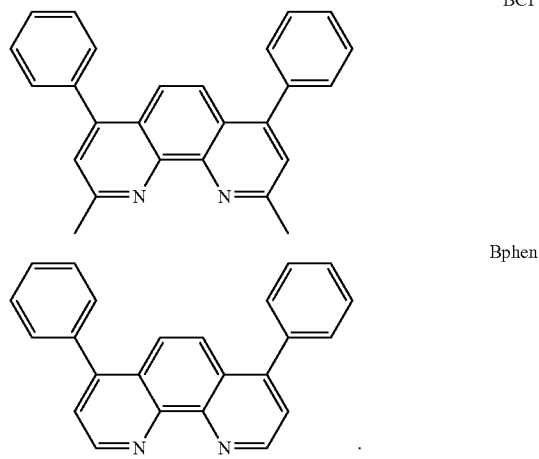

BCP

Bphen

A thickness of the hole blocking layer may be in a range of about 20 Å to about 1,000 Å, for example, about 30 Å to about 300 Å. When the thickness of the hole blocking layer is within any of these ranges, the hole blocking layer may have excellent (or suitable) hole blocking characteristics without a substantial increase in driving voltage.

The electron transport region may include an electron transport layer. The electron transport layer may be formed on the emission layer or the hole blocking layer by using one or more suitable methods such as vacuum deposition, spin coating, casting, a LB method, ink-jet printing, laser-printing, and/or laser-induced thermal imaging. When an electron transport layer is formed by vacuum deposition and/or spin coating, deposition and coating conditions for the electron transport layer may be the same as (or similar to) the deposition and coating conditions for the hole injection layer.

In some embodiments, the electron transport layer may include at least one compound selected from a compound represented by Formula 601 and a compound represented by Formula 602 illustrated below:

$$Ar_{601}-[(L_{601})_{xe1}-E_{601}]_{xe2}.$$  Formula 601

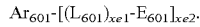

In Formula 601, $Ar_{601}$ may be selected from the group consisting of:
a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, and a naphthalene group, a heptalene group, a fluorene group, a spiro-fluorene group, a benzofluorene group, a dibenzofluorene group, a phenalene group, a phenanthrene group, a anthracene group, a fluoranthene group, a triphenylene group, a pyrene group, a chrysene group, a naphthacene group, a picene group, a perylene group, a pentaphene group, and an indenoanthracene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (wherein $Q_{301}$ to $Q_{303}$ may each independently be selected from hydrogen, a $C_1$-$C_{60}$ alkyl group, a $C_2$-$C_{60}$ alkenyl group, a $C_2$-$C_{60}$ aryl group, and a $C_1$-$C_{60}$ heteroaryl group);

description of $L_{601}$ may be the same as the description provided in connection with $L_{201}$;

$E_{601}$ may be selected from the group consisting of:
a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, carbazolyl, a phenanthridinyl group, an acridinyl group, a phenanthrolinyl group, a phenazinyl group, benzoimidazolyl, a benzofuranyl group, a benzothiophenyl group, isobenzothiazolyl, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

xe1 may be selected from 0, 1, 2, and 3; and
xe2 may be selected from 1, 2, 3, and 4.

Formula 602

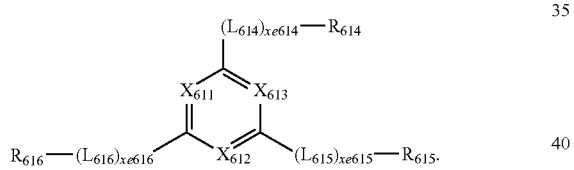

In Formula 602,
X$_{611}$ may be N or C-(L$_{611}$)$_{xe611}$-R$_{611}$, X$_{612}$ may be N or C-(L$_{612}$)$_{xe612}$-R$_{612}$, X$_{613}$ may be N or C-(L$_{613}$)$_{xe613}$-R$_{613}$, and at least one selected from X$_{611}$ to X$_{613}$ may be N;

descriptions of L$_{611}$ to L$_{616}$ may each independently be the same as the description provided in connection with L$_1$;

R$_{611}$ to R$_{616}$ may each independently be selected from the group consisting of:

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a biphenyl group, a terphenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xe611 to xe616 may each independently be selected from 0, 1, 2, and 3.

The compound represented by Formula 601 and the compound represented by Formula 602 may each independently be selected from Compounds ET1 to ET15 illustrated below:

ET1

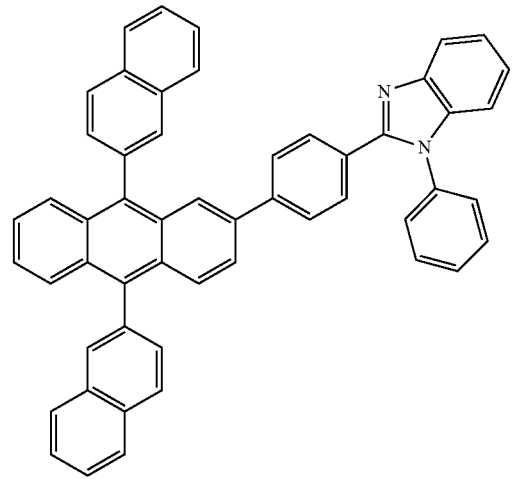

ET2

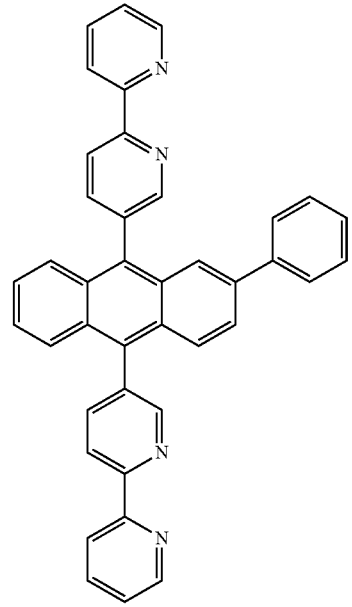

ET3
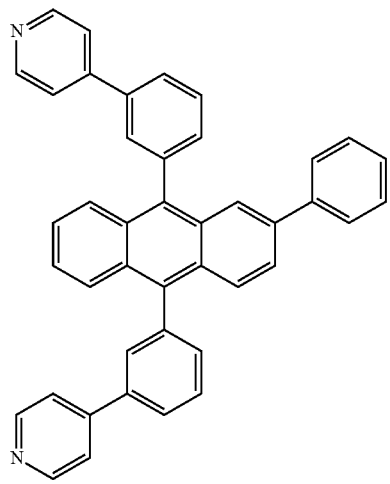
ET4
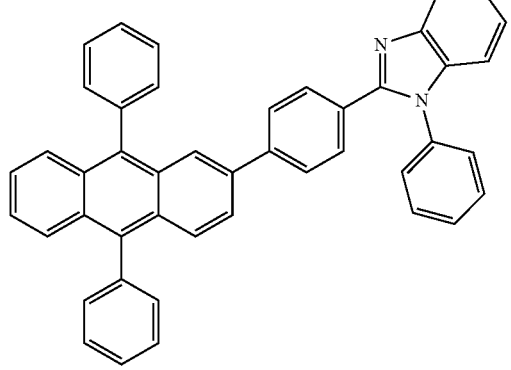
ET5
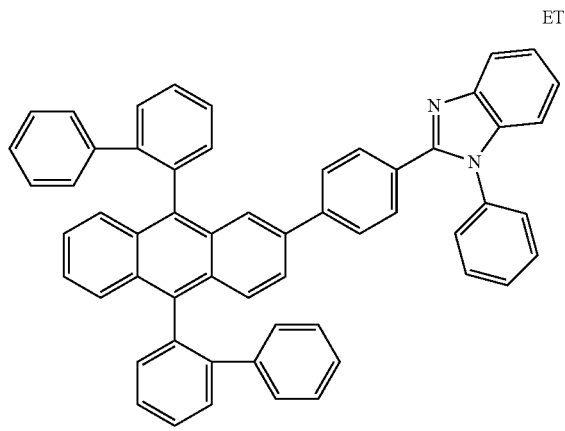
ET6
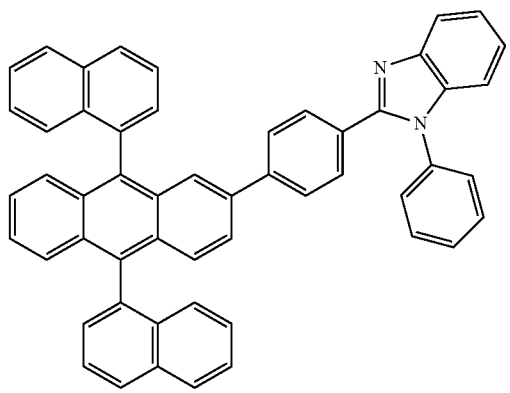
ET7
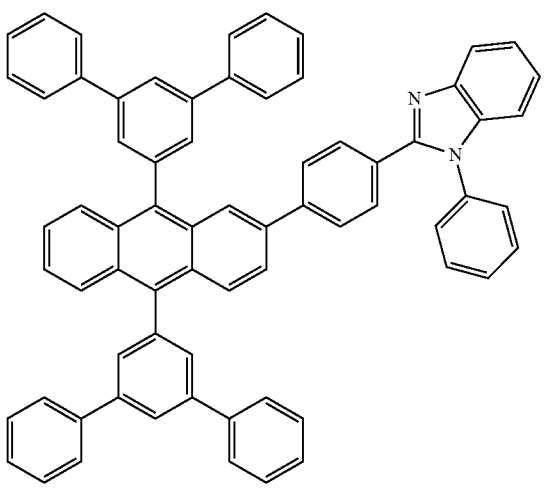
ET8
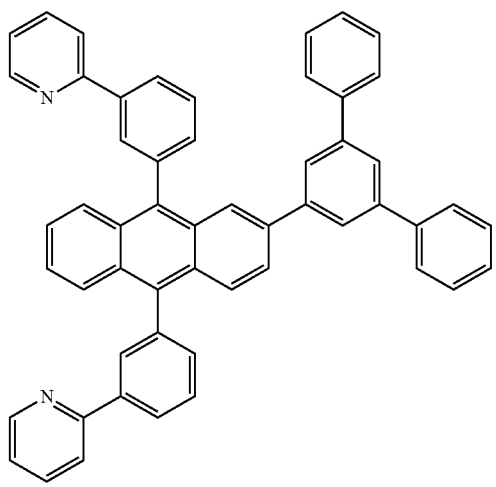

ET9
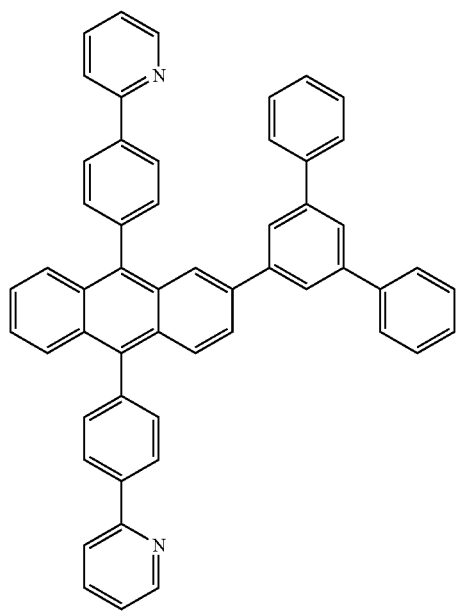
ET10
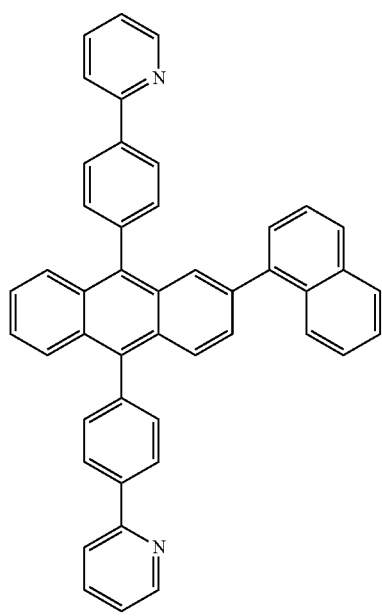
ET11
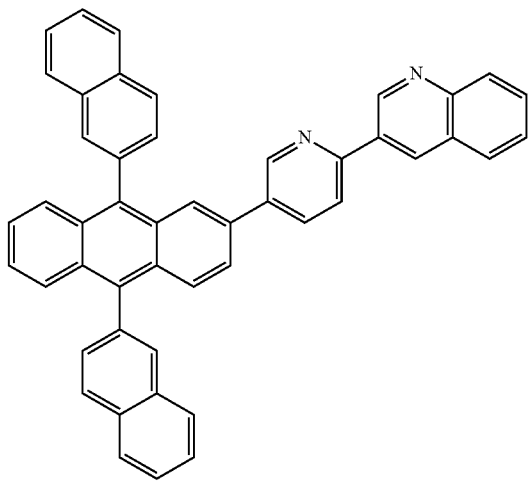
ET12
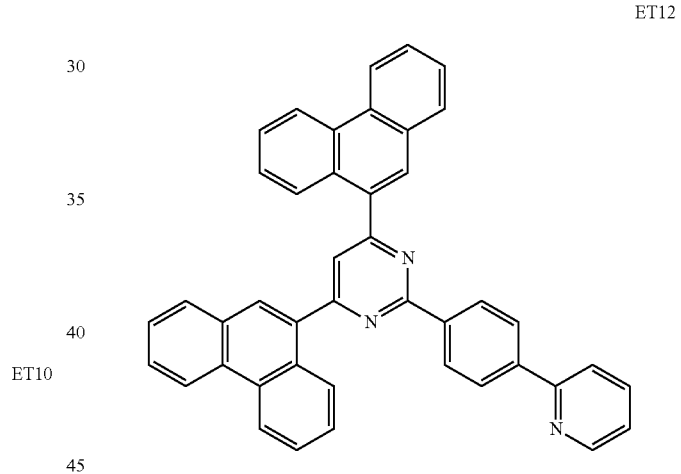
ET13
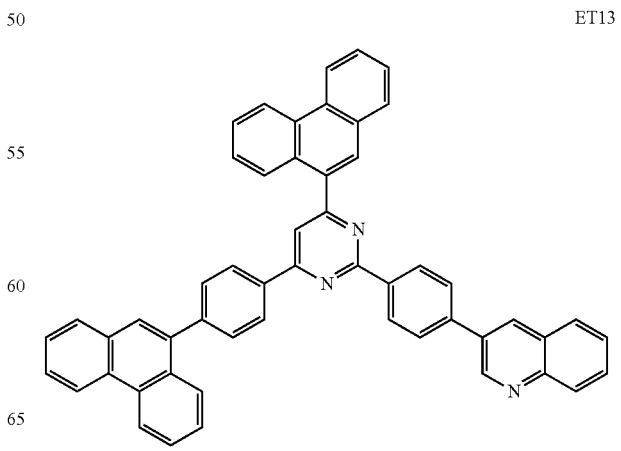

ET14

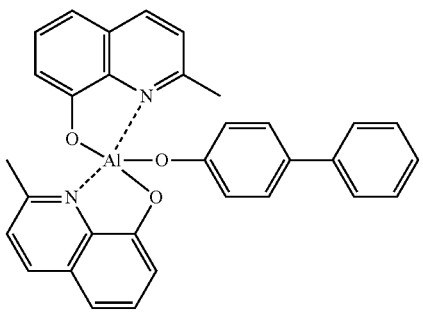

BAlq

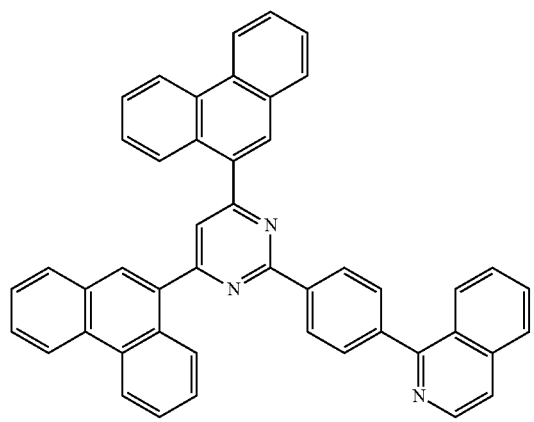

TAZ

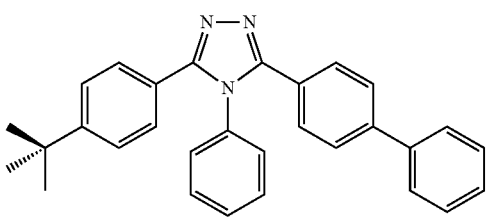

ET15

NTAZ

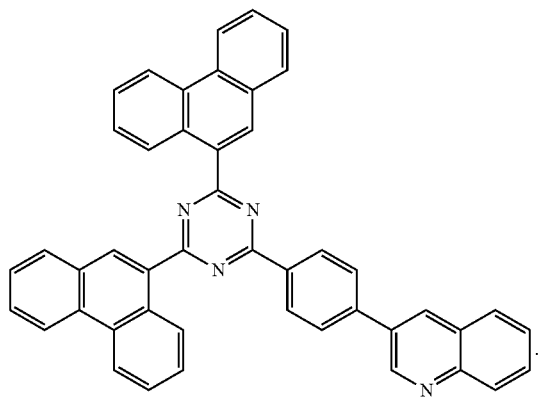

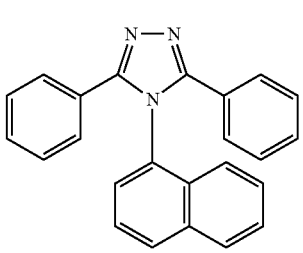

In some embodiments, the electron transport layer may further include at least one selected from BCP, Bphen, Alq$_3$, Balq, TAZ, and NTAZ.

A thickness of the electron transport layer may be in a range of about 100 Å to about 1,000 Å, for example, about 150 Å to about 500 Å. When the thickness of the electron transport layer is within any of the ranges described above, the electron transport layer may have satisfactory (or suitable) electron transport characteristics without a substantial increase in driving voltage.

The electron transport layer may further include, in addition to the materials described above, a metal-containing material.

The metal-containing material may include a Li complex. The Li complex may include, for example, Compound ET-D1 (lithium quinolate, LiQ) and/or Compound ET-D2.

Alq$_3$

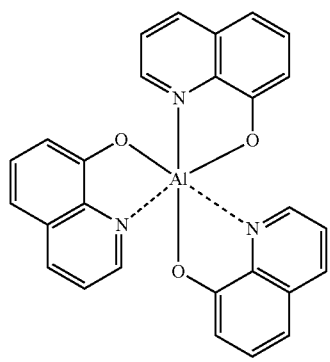

ET-D1

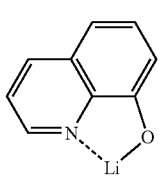

ET-D2

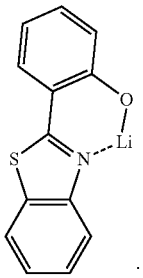

The electron transport region may include an electron injection layer that may function to facilitate injection of electrons from the second electrode 190.

The electron injection layer may be formed on the electron transport layer by using one or more suitable methods such as vacuum deposition, spin coating, casting, a LB method, ink-jet printing, laser-printing, and/or laser-induced thermal imaging. When an electron injection layer is formed by vacuum deposition and/or spin coating, deposition and coating conditions for the electron injection layer may be the same as (or similar to) those for the hole injection layer.

The electron injection layer may include at least one selected from LiF, NaCl, CsF, $Li_2O$, BaO, and LiQ.

A thickness of the electron injection layer may be in a range of about 1 Å to about 100 Å, for example, about 3 Å to about 90 Å. When the thickness of the electron injection layer is within any of the ranges described above, the electron injection layer may have satisfactory (or suitable) electron injection characteristics without a substantial increase in driving voltage.

The second electrode 190 may be disposed (e.g., positioned) on the organic layer 150 having the structure according to embodiments of the present disclosure. The second electrode 190 may be a cathode, which is an electron injection electrode, and in this regard, a material for forming the second electrode 190 may be selected from a metal, an alloy, an electrically conductive compound, and a mixture thereof, which have a relatively low work function. Non-limiting examples of the material for forming the second electrode 190 include lithium (Li), magnesium (Mg), aluminum (Al), aluminum-lithium (Al—Li), calcium (Ca), magnesium-indium (Mg—In), and magnesium-silver (Mg—Ag). In some embodiments, the material for forming the second electrode 190 may be ITO and/or IZO. The second electrode 190 may be a semi-transmissive electrode or a transmissive electrode.

Hereinbefore, the organic light-emitting device has been described with reference to the drawing, but embodiments of the present disclosure are not limited thereto.

The term "$C_1$-$C_{60}$ alkyl group," as used herein, may refer to a linear or branched aliphatic hydrocarbon monovalent group having 1 to 60 carbon atoms, and non-limiting examples thereof include a methyl group, an ethyl group, a propyl group, an isobutyl group, a sec-butyl group, a tert-butyl group, a pentyl group, an iso-amyl group, and a hexyl group. The term "$C_1$-$C_{60}$ alkylene group," as used herein, may refer to a divalent group having the same structure as the $C_1$-$C_{60}$ alkyl group.

The term "$C_1$-$C_{60}$ alkoxy group," as used herein, may refer to a monovalent group represented by —$OA_{101}$ (wherein $A_{101}$ is the $C_1$-$C_{60}$ alkyl group), and non-limiting examples thereof include a methoxy group, an ethoxy group, and an isopropoxy group.

The term "$C_2$-$C_{60}$ alkenyl group," as used herein, may refer to a hydrocarbon group having at least one carbon double bond at one or more positions along the hydrocarbon chain of the $C_2$-$C_{60}$ alkyl group (e.g., in the middle or at either terminal end of the $C_2$-$C_{60}$ alkyl group), and non-limiting examples thereof include an ethenyl group, a propenyl group, and a butenyl group. The term "$C_2$-$C_{60}$ alkenylene group," as used herein, may refer to a divalent group having the same structure as the $C_2$-$C_{60}$ alkenyl group.

The term "$C_2$-$C_{60}$ alkynyl group," as used herein, may refer to a hydrocarbon group having at least one carbon triple bond at one or more positions along the hydrocarbon chain of the $C_2$-$C_{60}$ alkyl group (e.g., in the middle or at either terminal end of the $C_2$-$C_{60}$ alkyl group), and non-limiting examples thereof include an ethynyl group and a propynyl group. The term "$C_2$-$C_{60}$ alkynylene group," as used herein, may refer to a divalent group having the same structure as the $C_2$-$C_{60}$ alkynyl group.

The term "$C_3$-$C_{10}$ cycloalkyl group," as used herein, may refer to a monovalent hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group," as used herein, may refer to a divalent group having the same structure as the $C_3$-$C_{10}$ cycloalkyl group.

The term "$C_1$-$C_{10}$ heterocycloalkyl group," as used herein, may refer to a monovalent monocyclic group having at least one heteroatom selected from N, O, Si, P, and S as a ring-forming atom, and 1 to 10 carbon atoms, and non-limiting examples thereof include a tetrahydrofuranyl group and a tetrahydrothiophenyl group. The term "$C_1$-$C_{10}$ heterocycloalkylene group," as used herein, may refer to a divalent group having the same structure as the $C_1$-$C_{10}$ heterocycloalkyl group.

The term "$C_3$-$C_{10}$ cycloalkenyl group," as used herein, may refer to a monovalent monocyclic group that has 3 to 10 carbon atoms and at least one double bond in the ring thereof and does not have aromaticity, and non-limiting examples thereof include a cyclopentenyl group, a cyclohexenyl group, and a cycloheptenyl group. The term "$C_3$-$C_{10}$ cycloalkenylene group," as used herein, may refer to a divalent group having the same structure as the $C_3$-$C_{10}$ cycloalkenyl group.

The term "$C_1$-$C_{10}$ heterocycloalkenyl group," as used herein, may refer to a monovalent monocyclic group that has at least one heteroatom selected from N, O, Si, P, and S as a ring-forming atom, 1 to 10 carbon atoms, and at least one double bond in its ring. Non-limiting examples of the $C_1$-$C_{10}$ heterocycloalkenyl group include a 2,3-hydrofuranyl group and a 2,3-hydrothiophenyl group. The term "$C_1$-$C_{10}$ heterocycloalkenylene group," as used herein, may refer to a divalent group having the same structure as the $C_1$-$C_{10}$ heterocycloalkenyl group.

The term "$C_6$-$C_{60}$ aryl group," as used herein, may refer to a monovalent group having a carbocyclic aromatic system having 6 to 60 carbon atoms, and the term "$C_6$-$C_{60}$ arylene group," as used herein, may refer to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each independently include two or more rings, the respective rings may be fused to each other.

The term "$C_1$-$C_{60}$ heteroaryl group," as used herein, may refer to a monovalent group having a carbocyclic aromatic system that has at least one heteroatom selected from N, O, Si, P, and S as a ring-forming atom, and 1 to 60 carbon atoms. The term "$C_1$-$C_{60}$ heteroarylene group," as used herein, may refer to a divalent group having a carbocyclic aromatic system that has at least one heteroatom selected from N, O, P, and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each independently include two or more rings, the respective rings may be fused to each other.

The term "$C_6$-$C_{60}$ aryloxy group," as used herein, may refer to a monovalent group represented by —$OA_{102}$ (wherein $A_{102}$ is the $C_6$-$C_{60}$ aryl group), and the term "$C_6$-$C_{60}$ arylthio group," as used herein, may refer to a monovalent group represented by —$SA_{103}$ (wherein $A_{103}$ is the $C_6$-$C_{60}$ aryl group).

The term "monovalent non-aromatic condensed polycyclic group," as used herein, may refer to a monovalent group that has two or more rings condensed (e.g., fused) to each other, only carbon atoms as ring forming atoms (e.g., 8 to 60 carbon atoms), and non-aromaticity in the entire molecular structure (e.g., not having overall aromaticity). A non-limiting example of the monovalent non-aromatic condensed polycyclic group is a fluorenyl group. The term "divalent non-aromatic condensed polycyclic group," as used herein, may refer to a divalent group having the same structure as the monovalent non-aromatic condensed polycyclic group.

The term "monovalent non-aromatic condensed heteropolycyclic group," as used herein, may refer to a monovalent group that has two or more rings condensed (e.g., fused) to each other, has at least one heteroatom selected from N, O, Si, P, and S, other than carbon atoms (e.g., 2 to 60 carbon atoms), as ring forming atoms, and has non-aromaticity in the entire molecular structure (e.g., does not have overall aromaticity). Non-limiting example of the monovalent non-aromatic condensed heteropolycyclic group is a carbazolyl group. The term "divalent non-aromatic condensed heteropolycyclic group," as used herein, may refer to a divalent group having the same structure as the monovalent non-aromatic condensed heteropolycyclic group.

At least one substituent of the substituted fluorenyl group, substituted spiro-bifluorenyl group, substituted carbazolyl group, substituted dibenzofuranyl group, substituted dibenzothiophenyl group, substituted dibenzosilolyl group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from the group consisting of:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group (e.g., aryloxy), $C_6$-$C_{60}$ arylthio group (e.g., arylthio), $C_1$-$C_{60}$ heteroaryl group, a monovalent non-aromatic condensed polycyclic group, a monovalent non-aromatic condensed heteropolycyclic group, and —$Si(Q_{11})(Q_{12})(Q_{13})$, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, and —$Si(Q_{21})(Q_{22})(Q_{23})$, and —$Si(Q_{31})(Q_{32})(Q_{33})$, wherein $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph," used herein, may refer to a phenyl group, the term "Me," used herein, may refer to a methyl group, the term "Et," used herein, may refer to an ethyl group, the term "ter-Bu," or "But" used herein, may refer to a tert-butyl group, and "D" may refer to deuterium.

Hereinafter, an organic light-emitting device according to one or more embodiments of the present disclosure will be described in further detail with reference to Synthesis Examples and Examples. The expression "B was used instead of A" used in describing Synthesis Examples may refer to a molar equivalent of A being identical to a molar equivalent of B.

EXAMPLES

Synthesis Example 1: Synthesis of Compound 10

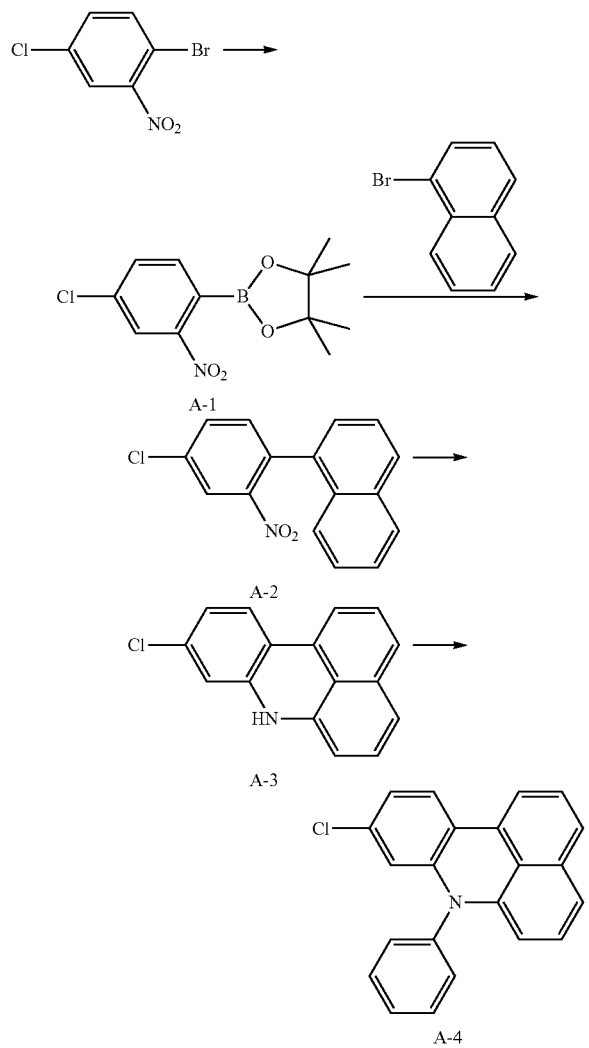

Synthesis of Intermediate A-1

5.96 g (23.6 millimoles (mmol)) of 1-bromo-4-chloro-2-nitrobenzene was dissolved in 200 milliliters (mL) of THF, and 10 mL (25.0 mmol, 2.5M in Hexane) of n-BuLi was slowly added dropwise thereto at a temperature of −78° C. After 1 hour of stirring the resulting solution at the same temperature, 9.3 mL (50 mmol) of 2-isopropoxy-4,4,5,5-tetramethyl-1,3,2-dioxaborolane was slowly added dropwise thereto, and then, the obtained reaction solution was stirred at a temperature of −78° C. for 1 hour. The resulting solution was additionally stirred for 24 hours at room temperature, and once the reaction was completed, 50 mL of a 10% HCl aqueous solution and 50 mL of $H_2O$ were added thereto, followed by three times of extraction using 80 mL of diethylether. An organic layer collected from the resulting solution was dried using magnesium sulfate, and a solvent was removed therefrom by evaporation. The residue obtained therefrom was separation-purified by silica gel column chromatography, thereby completing the preparation of 6.36 grams (g) (yield: 90%) of Intermediate A-1. The prepared compound was identified by liquid chromatography-mass spectroscopy (LC-MS).

($C_{12}H_{15}BClNO_4$: M+ 283.08)

Synthesis of Intermediate A-2

6.23 g (22.0 mmol) of Intermediate A-1, 4.56 g (22.0 mmol) of 1-bromonaphthalene, 1.27 g (1.1 mmol) of tetrakis (triphenylphosphine)palladium ($Pd(PPh_3)_4$), and 4.5 g (33 mmol) of $K_2CO_3$ were dissolved in 200 mL of a $THF/H_2O$ (2/1 volume ratio) mixed solution, and then, the resulting solution was stirred at a temperature of 70° C. for 5 hours. After the obtained reaction solution was cooled to room temperature, 60 mL of water was added thereto, followed by three times of extraction using 60 mL of ethylether. An organic layer obtained from the resulting solution was dried using magnesium sulfate, and then, a solvent was removed therefrom by evaporation. The residue obtained therefrom was separation-purified by silica gel column chromatography, thereby completing the preparation of 4.68 g (yield: 75%) of Intermediate A-2. The prepared compound was identified by LC-MS.

($C_{16}H_{10}ClNO_2$: M+ 283.04)

Synthesis of Intermediate A-3

2.83 g (10.00 mmol) of Intermediate A-2 and 8.3 g (50 mmol) of triethylphosphite were dissolved in 250 mL of cumene, and then, the resulting mixed solution was stirred under reflux in a nitrogen atmosphere for 24 hours. After the reaction was completed, an organic layer obtained by concentration under reduced pressure in high vacuum was separation-purified by silica gel column chromatography, thereby completing the preparation of 1.76 g (yield: 70%) of Intermediate A-3. The prepared compound was identified by LC-MS.

($C_{16}H_{10}ClN$: M+ 251.71)

Synthesis of Intermediate A-4

1.26 g (5.00 mmol) of Intermediate A-3, 0.95 g (6 mmol) of bromobenzene, 0.003 g (0.1 mmol) of $Pd(OAc)_2$, 0.1 g (0.5 mmol) of $P(tBu)_3$, and 0.84 g (7.5 mmol) of KOtBu were dissolved in 100 mL of toluene, and then, the resulting mixed solution was stirred under reflux in a nitrogen atmosphere for about 24 hours. After the obtained reaction solution was cooled to room temperature, an extraction process was performed thereon three times using 50 mL of water and 50 mL of diethylether. An organic layer obtained from the resulting solution was dried using magnesium sulfate, and a solvent was removed therefrom by evaporation. The residue obtained therefrom was separation-purified by silica gel column chromatography, thereby completing the preparation of 1.31 g (yield: 80%) of Intermediate A-4. The prepared compound was identified by LC-MS.

($C_{22}H_{14}ClN$: M+ 327.81)

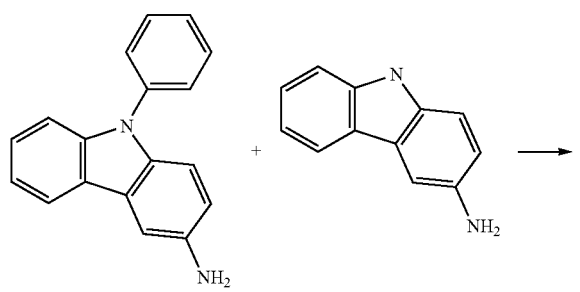

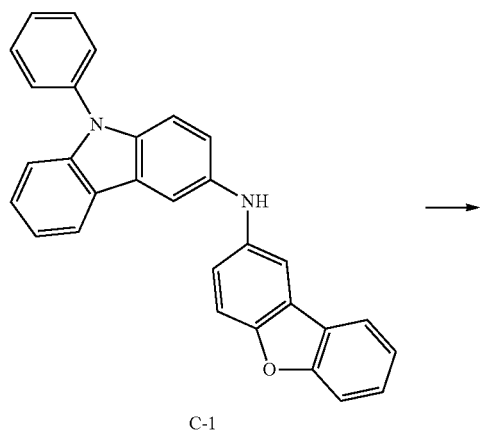

C-1

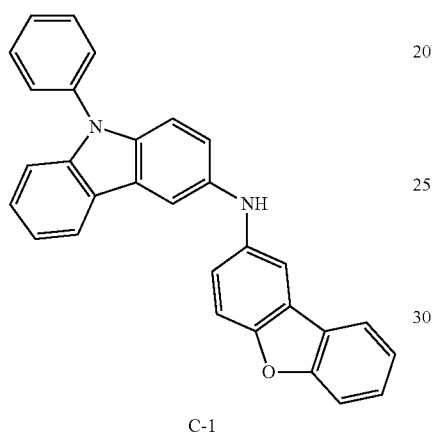

C-1

Synthesis of Intermediate C-1

7.75 g (30 mmol) of 9-phenyl-9H-carbazol-3-amine, 4.94 g (20.0 mmol) of 2-bromodibenzo[b,d]furan, 0.37 g (0.4 mmol) of Pd$_2$(dba)$_3$, 0.08 g (0.4 mmol) of P(tBu)$_3$, and 5.76 g (60 mmol) of KOtBu were dissolved in 200 mL of toluene, and then, the resulting mixed solution was stirred at a temperature of 85° C. for 4 hours. After the obtained reaction solution was cooled to room temperature, an extraction process was performed thereon using 50 mL of water and 50 mL of diethylether. An organic layer obtained from the resulting solution was dried using magnesium sulfate, and a solvent was removed therefrom by evaporation. The residue obtained therefrom was separation-purified by silica gel column chromatography, thereby completing the preparation of 6.79 g (yield: 80%) of Intermediate C-1. The prepared compound was identified by LC-MS.

(C$_{30}$H$_{20}$N$_2$O: M+ 424.50)

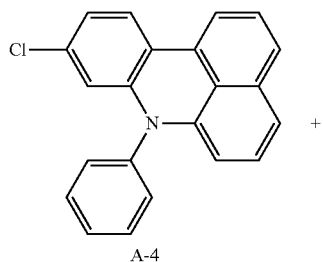

A-4

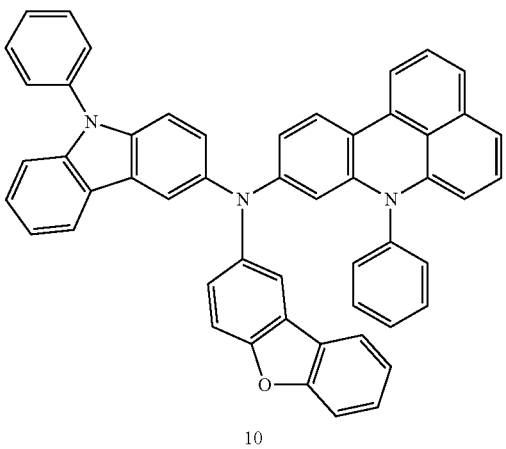

10

Synthesis of Compound 10

1.64 g (5.00 mmol) of Intermediate A-4, 2.12 g (5 mmol) of Intermediate C-1, 0.093 g (0.1 mmol) of Pd$_2$(dba)$_3$, 0.1 g (0.5 mmol) of P(tBu)$_3$, and 0.84 g (7.5 mmol) of KOtBu were dissolved in 100 mL of toluene, and then, the resulting mixed solution was stirred under reflux in a nitrogen atmosphere for 24 hours. After the obtained reaction solution was cooled to room temperature, an extraction process was performed thereon three times using 50 mL of water and 50 mL of diethylether. An organic layer obtained from the resulting solution was dried using magnesium sulfate, and a solvent was removed therefrom by evaporation. The residue obtained therefrom was separation-purified by silica gel column chromatography, thereby completing the preparation of 2.97 g (yield: 83%) of Compound 10. The prepared compound was identified by LC-MS and nuclear magnetic resonance (NMR).

(C$_{52}$H$_{33}$N$_3$O: M+ 715.86)

Synthesis Example 2: Synthesis of Compound 14

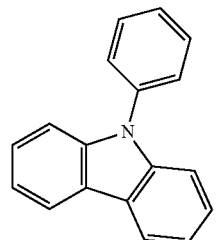

+

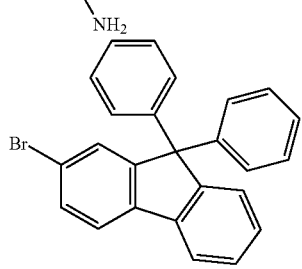

→

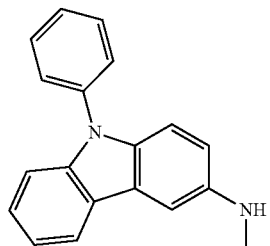

C-2

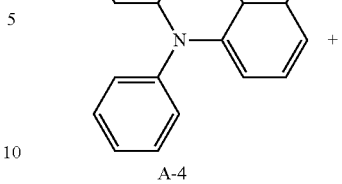

A-4

+

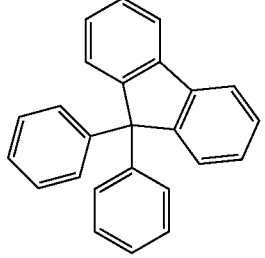

C-2

→

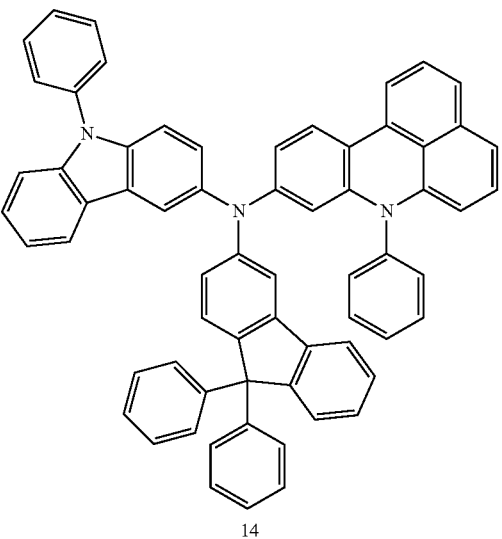

14

Synthesis of Intermediate C-2

7.75 g (30 mmol) of 9-phenyl-9H-carbazol-3-amine, 7.95 g (20.0 mmol) of 2-bromo-9,9-diphenyl-9H-fluorene, 0.37 g (0.4 mmol) of $Pd_2(dba)_3$, 0.08 g (0.4 mmol) of $P(tBu)_3$, and 5.76 g (60 mmol) of KOtBu were dissolved in 200 mL of toluene, and then, the resulting mixed solution was stirred at a temperature of 85° C. for 4 hours. After the obtained reaction solution was cooled to room temperature, an extraction process was performed thereon using 50 mL of water and 50 mL of diethylether. An organic layer obtained from the resulting solution was dried using magnesium sulfate, and a solvent was removed therefrom by evaporation. The residue obtained therefrom was separation-purified by silica gel column chromatography, thereby completing the preparation of 9.31 g (yield: 81%) of Intermediate C-2. The prepared compound was identified by LC-MS.

($C_{43}H_{30}N_2$: M+ 574.73)

Synthesis of Compound 14

3.55 g (yield: 82%) of Compound 14 was obtained in the same (or substantially the same) manner as in Synthesis of Compound 10, except that 2.87 g (5 mmol) of Intermediate C-2 was used instead of Intermediate C-1. The prepared compound was identified by LC-MS and NMR.

($C_{65}H_{43}N_3$: M+ 866.08)

143

Synthesis Example 3: Synthesis of Compound 18

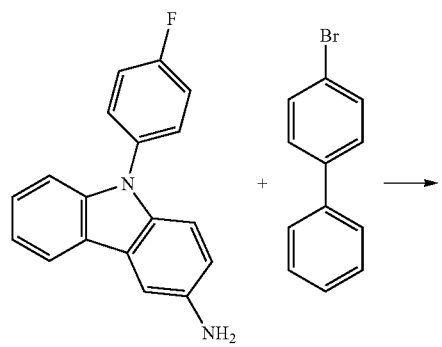

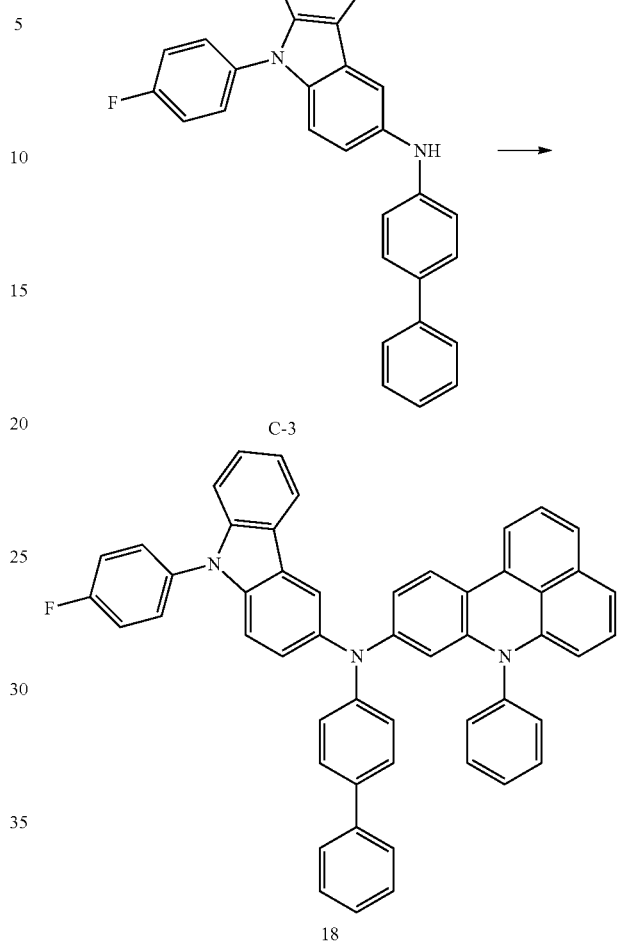

Synthesis of Intermediate C-3

8.29 g (30 mmol) of 9-(4-fluorophenyl)-9H-carbazol-3-amine, 4.66 g (20.0 mmol) of 4-bromo-1,1'-biphenyl, 0.37 g (0.4 mmol) of $Pd_2(dba)_3$, 0.08 g (0.4 mmol) of $P(tBu)_3$, and 5.76 g (60 mmol) of KOtBu were dissolved in 200 mL of toluene, and then, the resulting mixed solution was stirred at a temperature of 85° C. for 4 hours. After the obtained reaction solution was cooled to room temperature, an extraction process was performed thereon using 50 mL of water and 50 mL of diethylether. An organic layer obtained from the resulting solution was dried using magnesium sulfate, and a solvent was removed therefrom by evaporation. The residue obtained therefrom was separation-purified by silica gel column chromatography, thereby completing the preparation of 6.86 g (yield: 80%) of Intermediate C-3. The prepared compound was identified by LC-MS.

($C_{30}H_{21}FN_2$: M+ 428.51)

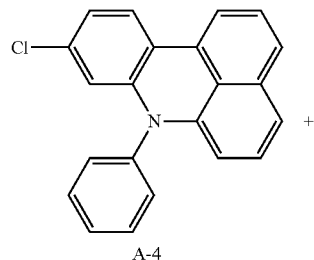

144

-continued

Synthesis of Compound 18

2.92 g (yield: 81%) of Compound 18 was obtained in the same (or substantially the same) manner as in Synthesis of Compound 10, except that 2.14 g (5 mmol) of Intermediate C-3 was used instead of Intermediate C-1. The prepared compound was identified by LC-MS and NMR.

($C_{52}H_{34}FN_3$: M+ 719.86)

Synthesis Example 4: Synthesis of Compound 22

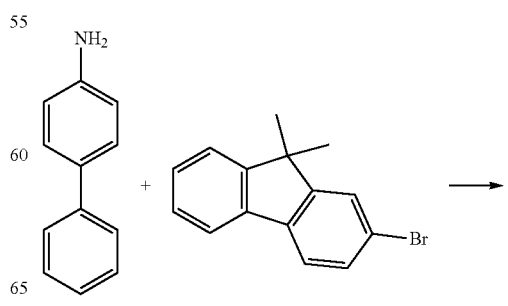

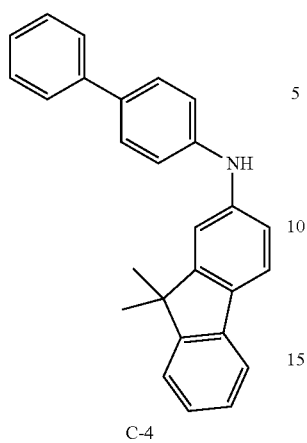

C-4

Synthesis of Intermediate C-4

5.08 g (30 mmol) of 4-aminobiphenyl, 5.46 g (20.0 mmol) of 2-bromo-9,9-dimethylfluorene, 0.37 g (0.4 mmol) of Pd$_2$(dba)$_3$, 0.08 g (0.4 mmol) of P(tBu)$_3$, and 5.76 g (60 mmol) of KOtBu were dissolved in 200 mL of toluene, and then, the resulting mixed solution was stirred at a temperature of 85° C. for 4 hours. After the obtained reaction solution was cooled to room temperature, an extraction process was performed thereon using 50 mL of water and 50 mL of diethylether. An organic layer obtained from the resulting solution was dried using magnesium sulfate, and a solvent was removed therefrom by evaporation. The residue obtained therefrom was separation-purified by silica gel column chromatography, thereby completing the preparation of 6.07 g (yield: 84%) of Intermediate C-4. The prepared compound was identified by LC-MS.

(C$_{27}$H$_{23}$N: M+ 361.49)

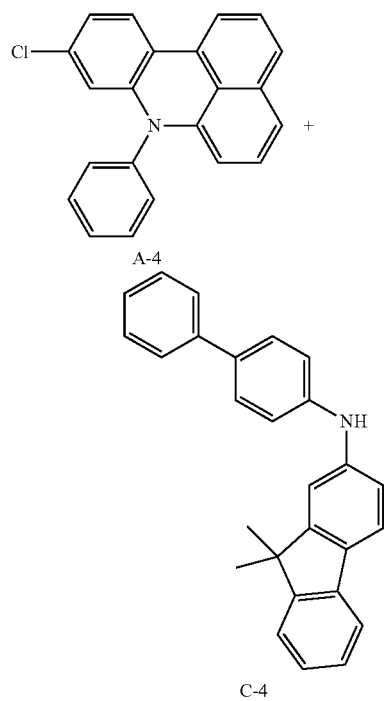

A-4

C-4

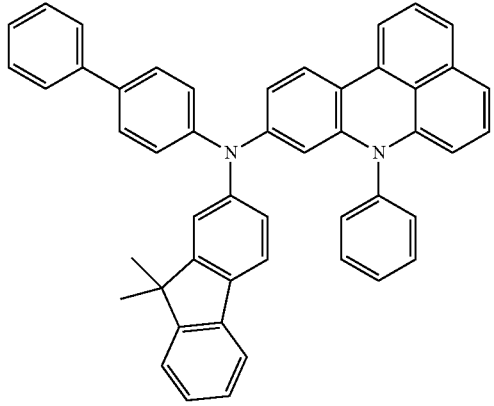

22

Synthesis of Compound 22

2.68 g (yield: 82%) of Compound 22 was obtained in the same (or substantially the same) manner as in Synthesis of Compound 10, except that 1.81 g (5 mmol) of Intermediate C-4 was used instead of Intermediate C-1. The prepared compound was identified by LC-MS and NMR.

(C$_{49}$H$_{36}$N$_2$: M+ 652.84)

Synthesis Example 5: Synthesis of Compound 29

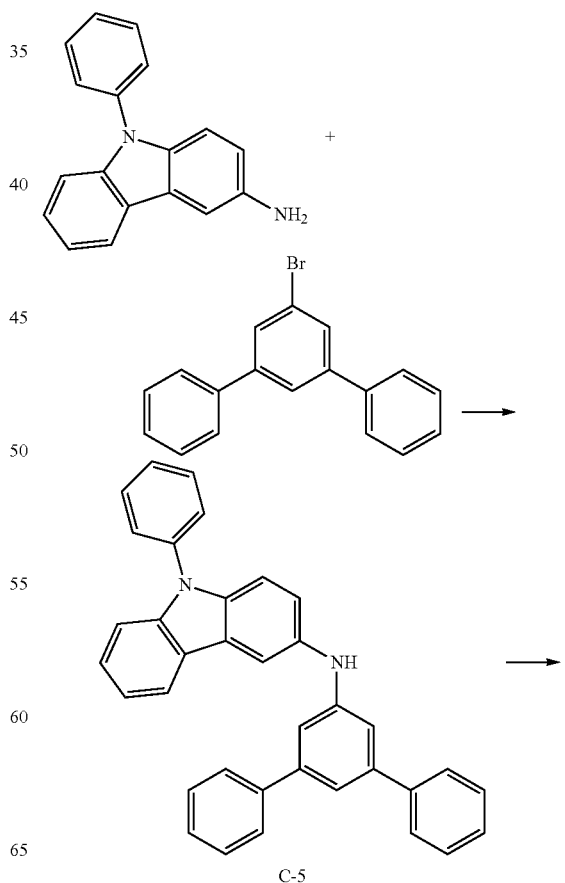

C-5

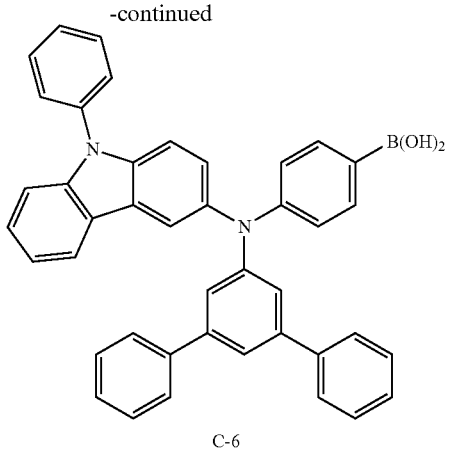

C-6

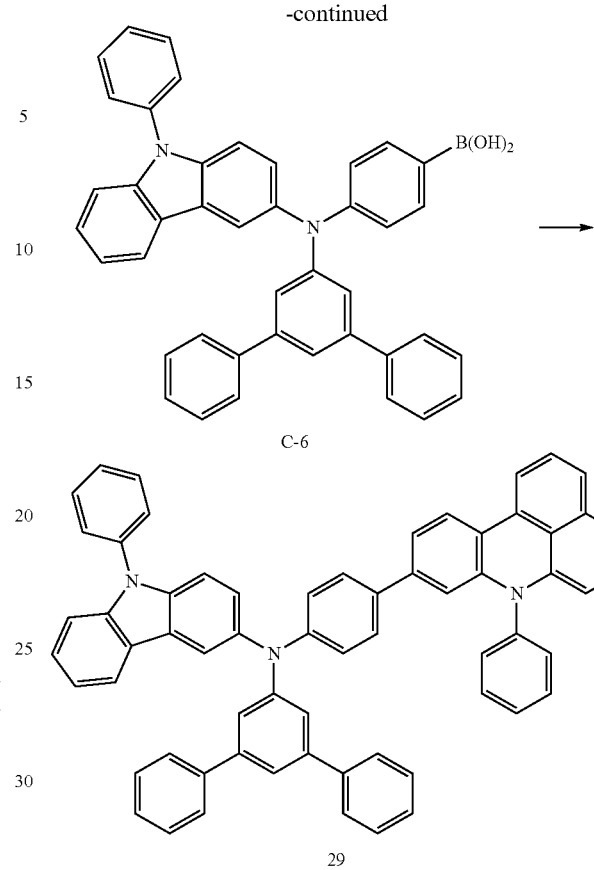

C-6

29

Synthesis of Intermediate C-5

7.75 g (30 mmol) of 9-phenyl-9H-carbazol-3-amine, 6.18 g (20.0 mmol) of 5'-bromo-1,1':3',1''-terphenyl, 0.37 g (0.4 mmol) of Pd$_2$(dba)$_3$, 0.08 g (0.4 mmol) of P(tBu)$_3$, and 5.76 g (60 mmol) of KOtBu were dissolved in 200 mL of toluene, and then, the resulting mixed solution was stirred at a temperature of 85° C. for 4 hours. After the obtained reaction solution was cooled to room temperature, an extraction process was performed thereon using 50 mL of water and 50 mL of diethylether. An organic layer obtained from the resulting solution was dried using magnesium sulfate, and a solvent was removed therefrom by evaporation. The residue obtained therefrom was separation-purified by silica gel column chromatography, thereby completing the preparation of 7.69 g (yield: 79%) of Intermediate C-5. The prepared compound was identified by LC-MS.

(C$_{36}$H$_{26}$N$_2$: M+ 486.62)

Synthesis of Intermediate C-6

9.73 g (20 mmol) of Intermediate C-5, 4.02 g (20.0 mmol) of (4-bromophenyl)boronic acid, 0.37 g (0.4 mmol) of Pd$_2$(dba)$_3$, 0.08 g (0.4 mmol) of P(tBu)$_3$, and 5.76 g (60 mmol) of KOtBu were dissolved in 200 mL of toluene, and then, the resulting mixed solution was stirred at a temperature of 85° C. for 4 hours. After the obtained reaction solution was cooled to room temperature, an extraction process was performed thereon using 50 mL of water and 50 mL of diethylether. An organic layer obtained from the resulting solution was dried using magnesium sulfate, and a solvent was removed therefrom by evaporation. The residue obtained therefrom was separation-purified by silica gel column chromatography, thereby completing the preparation of 7.69 g (yield: 79%) of Intermediate C-6. The prepared compound was identified by LC-MS.

(C$_{42}$H$_{31}$BN$_2$O$_2$: M+ 606.53)

Synthesis of Compound 29

1.64 g (5.00 mmol) of Intermediate A-4, 2.43 g (5 mmol) of Intermediate C-6, 0.58 g (0.50 mmol) of Pd(PPh$_3$)$_4$, and 2.08 g (15 mmol) of K$_2$CO$_3$ were dissolved in 200 mL of a THF/H$_2$O (2/1 volume ratio) mixed solution, and then, the resulting solution was stirred at a temperature of 70° C. for 5 hours. After the obtained reaction solution was cooled to room temperature, 60 mL of water was added thereto, followed by three times of extraction using 60 mL of ethylether. An organic layer obtained from the resulting solution was dried using magnesium sulfate, and then, a solvent was removed therefrom by evaporation. The residue obtained therefrom was separation-purified by silica gel column chromatography, thereby completing the preparation of 3.07 g (yield: 72%) of Compound 29. The prepared compound was identified by LC-MS and NMR.

(C$_{64}$H$_{43}$N$_3$: M+ 854.07)

Synthesis Example 6: Synthesis of Compound 36

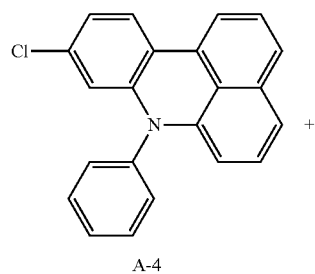

A-4

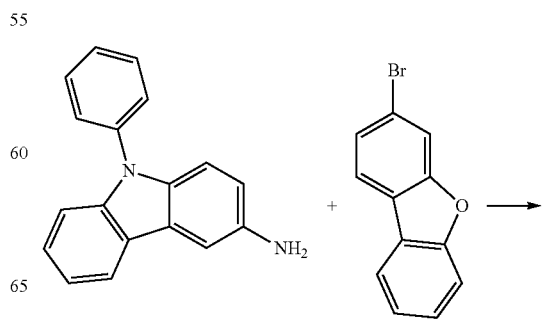

-continued

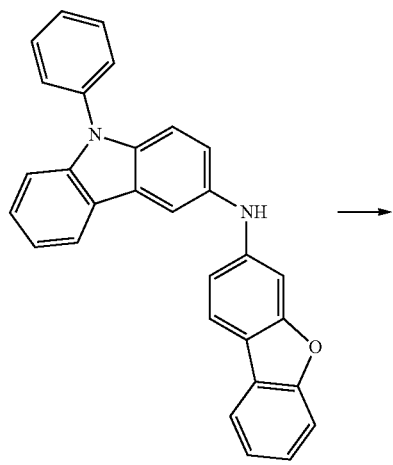

C-7

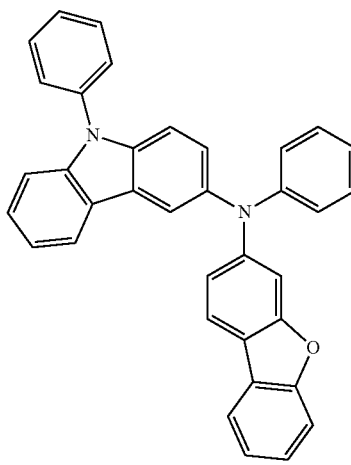

C-8

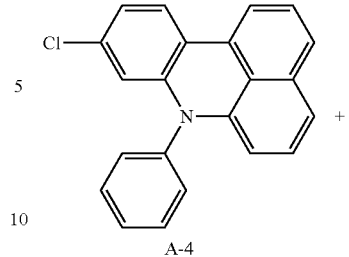

A-4

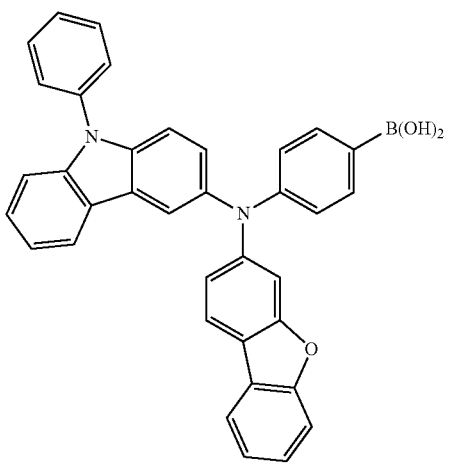

C-8

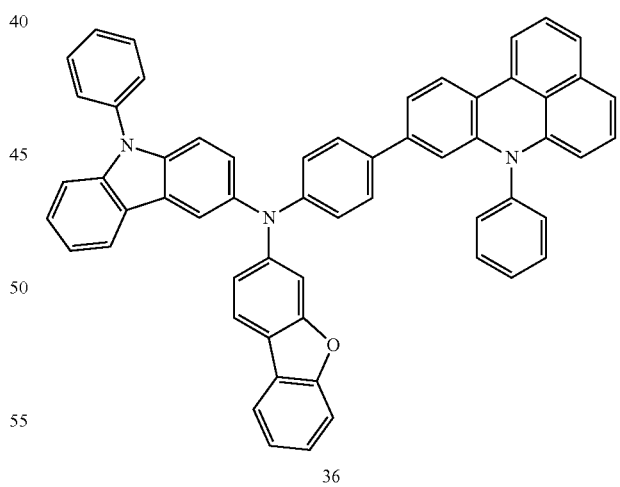

36

Synthesis of Intermediate C-7

7.75 g (30 mmol) of 9-phenyl-9H-carbazol-3-amine, 4.94 g (20.0 mmol) of 3-bromodibenzo[b,d]furan, 0.37 g (0.4 mmol) of $Pd_2(dba)_3$, 0.08 g (0.4 mmol) of $P(tBu)_3$, and 5.76 g (60 mmol) of KOtBu were dissolved in 200 mL of toluene, and then, the resulting mixed solution was stirred at a temperature of 85° C. for 4 hours. After the obtained reaction solution was cooled to room temperature, an extraction process was performed thereon using 50 mL of water and 50 mL of diethylether. An organic layer obtained from the resulting solution was dried using magnesium sulfate, and a solvent was removed therefrom by evaporation. The residue obtained therefrom was separation-purified by silica gel column chromatography, thereby completing the preparation of 6.96 g (yield: 82%) of Intermediate C-7. The prepared compound was identified by LC-MS.

($C_{30}H_{20}N_2O$: M+ 424.50)

Synthesis of Intermediate C-8

8.49 g (yield: 78%) of Intermediate C-8 was obtained in the same (or substantially the same) manner as in Synthesis of Intermediate C-6, except that 12.12 g (20 mmol) of Intermediate C-7 was used instead of Intermediate C-5. The prepared compound was identified by LC-MS.

($C_{36}H_{25}BN_2O_3$: M+ 544.42)

Synthesis of Compound 36

2.93 g (yield: 74%) of Compound 36 was obtained in the same (or substantially the same) manner as in Synthesis of Compound 29, except that 2.72 g (5 mmol) of Intermediate C-8 was used instead of Intermediate C-6. The prepared compound was identified by LC-MS and NMR.

($C_{58}H_{37}N_3O$: M+ 791.95)

Synthesis Example 7: Synthesis of Compound 41

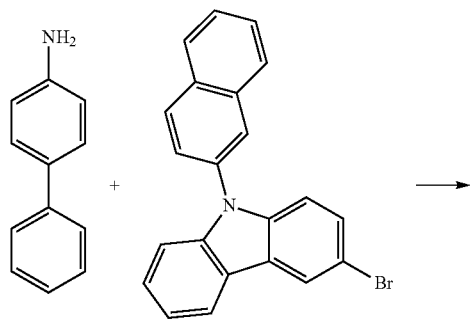

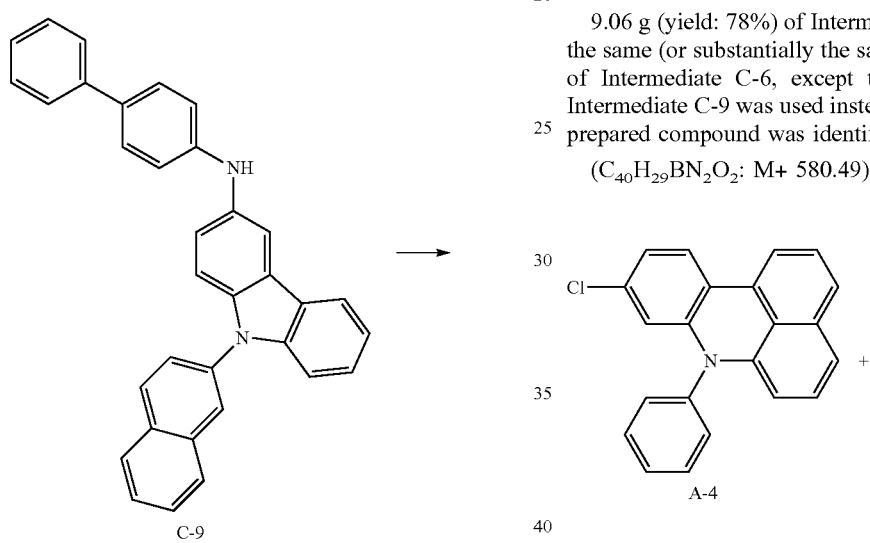

Synthesis of Intermediate C-9

5.08 g (30 mmol) of 4-aminobiphenyl, 7.45 g (20.0 mmol) of 3-bromo-9-(naphthalen-2-yl)-9H-carbazole, 0.37 g (0.4 mmol) of $Pd_2(dba)_3$, 0.08 g (0.4 mmol) of $P(tBu)_3$, and 5.76 g (60 mmol) of KOtBu were dissolved in 200 mL of toluene, and then, the resulting mixed solution was stirred at a temperature of 85° C. for 4 hours. After the obtained reaction solution was cooled to room temperature, an extraction process was performed thereon using 50 mL of water and 50 mL of diethylether. An organic layer obtained from the resulting solution was dried using magnesium sulfate, and a solvent was removed therefrom by evaporation. The residue obtained therefrom was separation-purified by silica gel column chromatography, thereby completing the preparation of 7.36 g (yield: 80%) of Intermediate C-9. The prepared compound was identified by LC-MS.

($C_{34}H_{24}N_2$: M+ 460.58)

Synthesis of Intermediate C-10

9.06 g (yield: 78%) of Intermediate C-10 was obtained in the same (or substantially the same) manner as in Synthesis of Intermediate C-6, except that 9.21 g (20 mmol) of Intermediate C-9 was used instead of Intermediate C-5. The prepared compound was identified by LC-MS.

($C_{40}H_{29}BN_2O_2$: M+ 580.49)

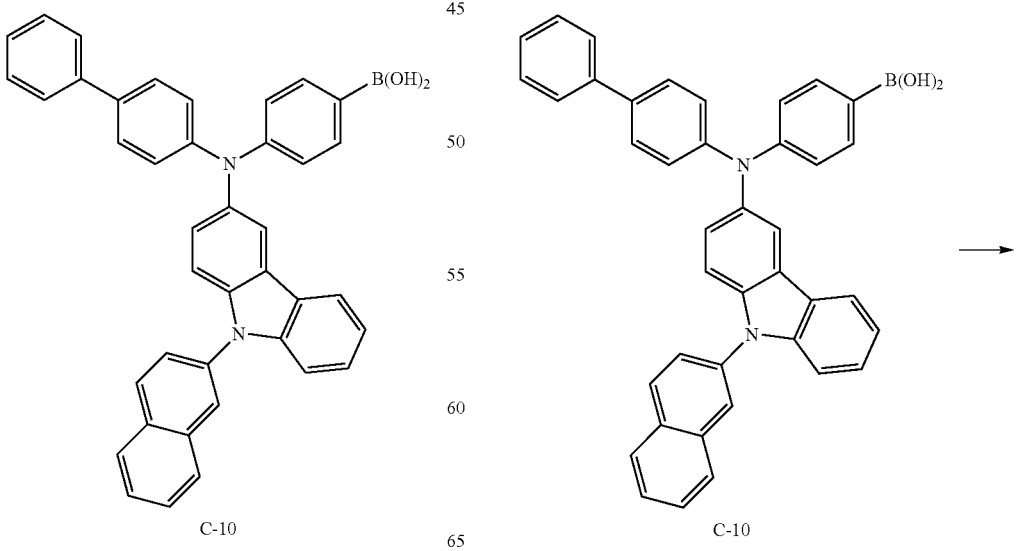

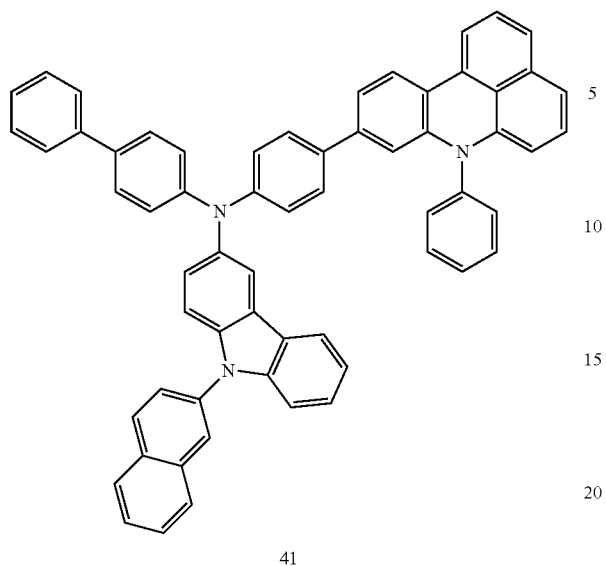

41

Synthesis of Compound 41

3.27 g (yield: 79%) of Compound 41 was obtained in the same (or substantially the same) manner as in Synthesis of Compound 29, except that 2.90 g (5 mmol) of Intermediate C-10 was used instead of Intermediate C-6. The prepared compound was identified by LC-MS and NMR.

($C_{62}H_{41}N_3$: M+ 828.03)

Synthesis Example 8: Synthesis of Compound 48

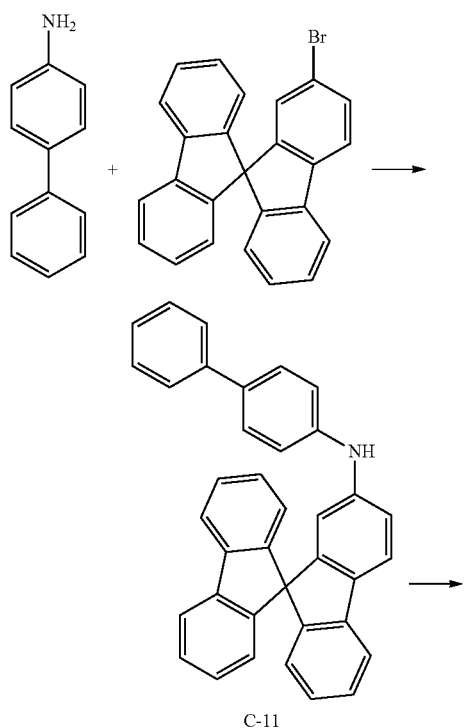

C-11

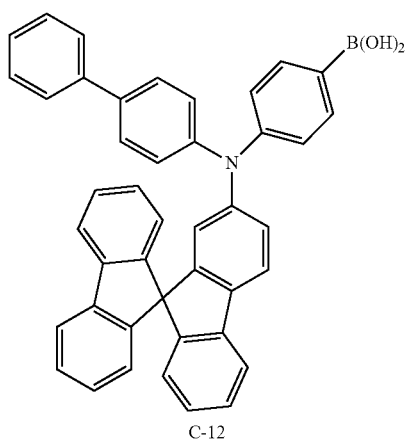

C-12

Synthesis of Intermediate C-11

5.08 g (30 mmol) of 4-aminobiphenyl, 7.90 g (20.0 mmol) of 2-bromo-9,9'-spirobifluorene, 0.37 g (0.4 mmol) of $Pd_2(dba)_3$, 0.08 g (0.4 mmol) of $P(tBu)_3$, and 5.76 g (60 mmol) of KOtBu were dissolved in 200 mL of toluene, and then, the resulting mixed solution was stirred at a temperature of 85° C. for 4 hours. After the obtained reaction solution was cooled to room temperature, an extraction process was performed thereon using 50 mL of water and 50 mL of diethylether. An organic layer obtained from the resulting solution was dried using magnesium sulfate, and a solvent was removed therefrom by evaporation. The residue obtained therefrom was separation-purified by silica gel column chromatography, thereby completing the preparation of 7.25 g (yield: 75%) of Intermediate C-11. The prepared compound was identified by LC-MS.

($C_{37}H_{25}N$: M+ 483.61)

Synthesis of Intermediate C-12

8.93 g (yield: 74%) of Intermediate C-12 was obtained in the same (or substantially the same) manner as in Synthesis of Intermediate C-6, except that 9.67 g (20 mmol) of Intermediate C-11 was used instead of Intermediate C-5. The prepared compound was identified by LC-MS.

($C_{43}H_{30}BNO_2$: M+ 603.53)

Synthesis of Compound 48

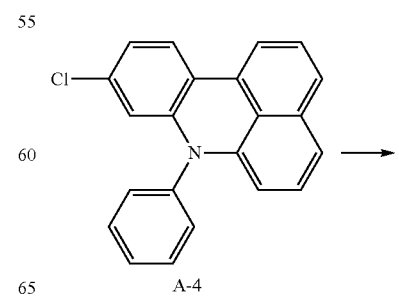

A-4

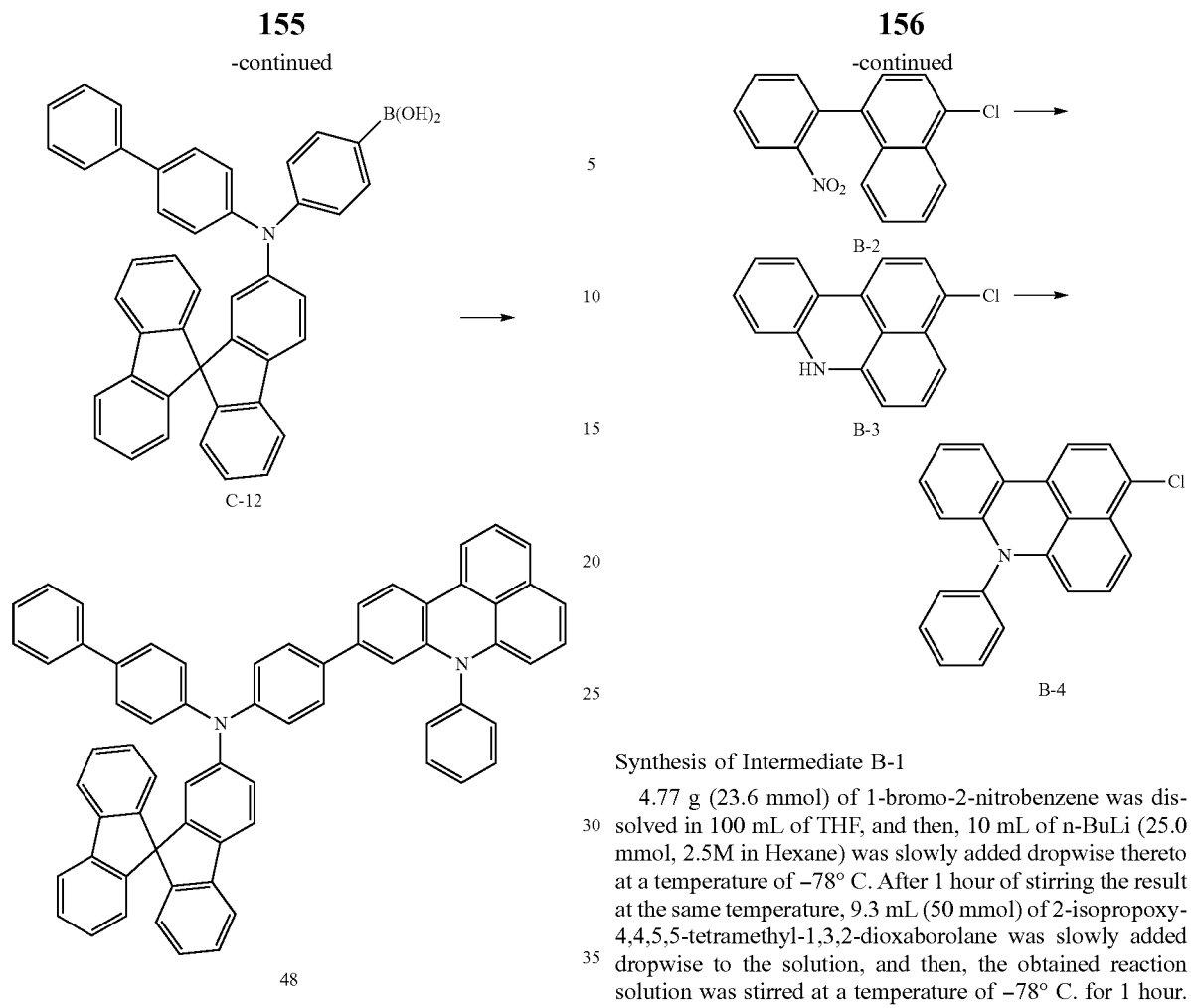

3.23 g (yield: 76%) of Compound 48 was obtained in the same (or substantially the same) manner as in Synthesis of Compound 29, except that 3.02 g (5 mmol) Intermediate C-12 was used instead of Intermediate C-6. The prepared compound was identified by LC-MS and NMR.

($C_{65}H_{42}N_2$: M+ 851.07)

Synthesis Example 9: Synthesis of Compound 54

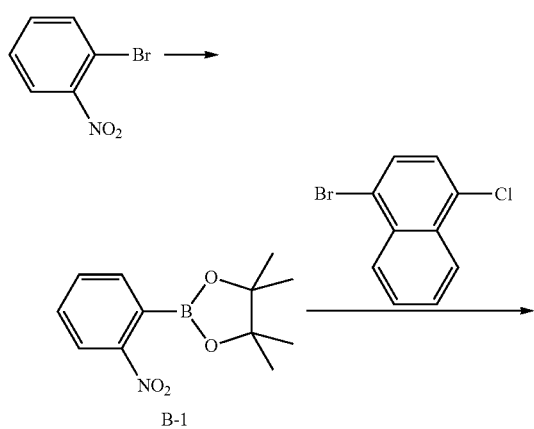

Synthesis of Intermediate B-1

4.77 g (23.6 mmol) of 1-bromo-2-nitrobenzene was dissolved in 100 mL of THF, and then, 10 mL of n-BuLi (25.0 mmol, 2.5M in Hexane) was slowly added dropwise thereto at a temperature of −78° C. After 1 hour of stirring the result at the same temperature, 9.3 mL (50 mmol) of 2-isopropoxy-4,4,5,5-tetramethyl-1,3,2-dioxaborolane was slowly added dropwise to the solution, and then, the obtained reaction solution was stirred at a temperature of −78° C. for 1 hour. The resulting solution was additionally stirred for 24 hours at room temperature, and once the reaction was completed, 50 mL of a 10% HCl aqueous solution and 50 mL of $H_2O$ were added thereto, followed by three times of extraction using 80 mL of diethylether. An organic layer collected from the resulting solution was dried using magnesium sulfate, and a solvent was removed therefrom by evaporation. The residue obtained therefrom was separation-purified by silica gel column chromatography, thereby completing the preparation of 5.29 g (yield: 90%) of Intermediate B-1. The prepared compound was identified by LC-MS.

($C_{12}H_{16}BNO_4$: M+ 249.07)

Synthesis of Intermediate B-2

5.48 g (22.0 mmol) of Intermediate B-1, 5.31 g (22.0 mmol) of 1-bromo-4-chloronaphthalene, 1.27 g (1.1 mmol) of Pd(PPh$_3$)$_4$, and 4.5 g (33 mmol) of $K_2CO_3$ were dissolved in 200 mL of a THF/$H_2O$ (2/1 volume ratio) mixed solution, and then, the resulting solution was stirred at a temperature of 70° C. for 5 hours. After the obtained reaction solution was cooled to room temperature, 60 mL of water was added thereto, followed by three times of extraction using 60 mL of ethylether. An organic layer obtained from the resulting solution was dried using magnesium sulfate, and then, a solvent was removed therefrom by evaporation. The residue obtained therefrom was separation-purified by silica gel column chromatography, thereby completing the preparation of 4.68 g (yield: 75%) of Intermediate B-2. The prepared compound was identified by LC-MS.

($C_{16}H_{10}ClNO_2$: M+ 283.04)

Synthesis of Intermediate B-3

2.83 g (10.00 mmol) of Intermediate B-2 and 8.3 g (50 mmol) of triethylphosphite were dissolved in 250 mL of cumene, and then, the resulting mixed solution was stirred under reflux in a nitrogen atmosphere for 24 hours. After the reaction was completed, an organic layer obtained by concentration under reduced pressure in high vacuum was separation-purified by silica gel column chromatography, thereby completing the preparation of 1.76 g (yield: 70%) of Intermediate B-3. The prepared compound was identified by LC-MS.

($C_{16}H_{10}ClN$: M+ 251.71)

Synthesis of Intermediate B-4

1.26 g (5.00 mmol) of Intermediate B-3, 0.95 g (6 mmol) of bromobenzene, 0.003 g (0.1 mmol) of $Pd(OAc)_2$, 0.1 g (0.5 mmol) of $P(tBu)_3$, and 0.84 g (7.5 mmol) of KOtBu were dissolved in 100 mL of toluene, and then, the resulting mixed solution was stirred under reflux in a nitrogen atmosphere for 24 hours. After the reaction was completed, an extraction process was performed thereon three times using 50 mL of water and 50 mL of diethylether. An organic layer obtained from the resulting solution was dried using magnesium sulfate, and a solvent was removed therefrom by evaporation. The residue obtained therefrom was separation-purified by silica gel column chromatography, thereby completing the preparation of 1.31 g (yield: 80%) of Intermediate B-4. The prepared compound was identified by LC-MS.

($C_{22}H_{14}ClN$: M+ 327.81)

Synthesis Example 10: Synthesis of Compound 59 and then, the resulting mixed solution was stirred at a temperature of 85° C. for 4 hours. After the obtained reaction solution was cooled to room temperature, an extraction process was performed thereon using 50 mL of water and 50 mL of diethylether. An organic layer obtained from the resulting solution was dried using magnesium sulfate, and a solvent was removed therefrom by evaporation. The residue obtained therefrom was separation-purified by silica gel column chromatography, thereby completing the preparation of 7.40 g (yield: 84%) of Intermediate D-1. The prepared compound was identified by LC-MS.

($C_{30}H_{20}N_2S$: M+ 440.56)

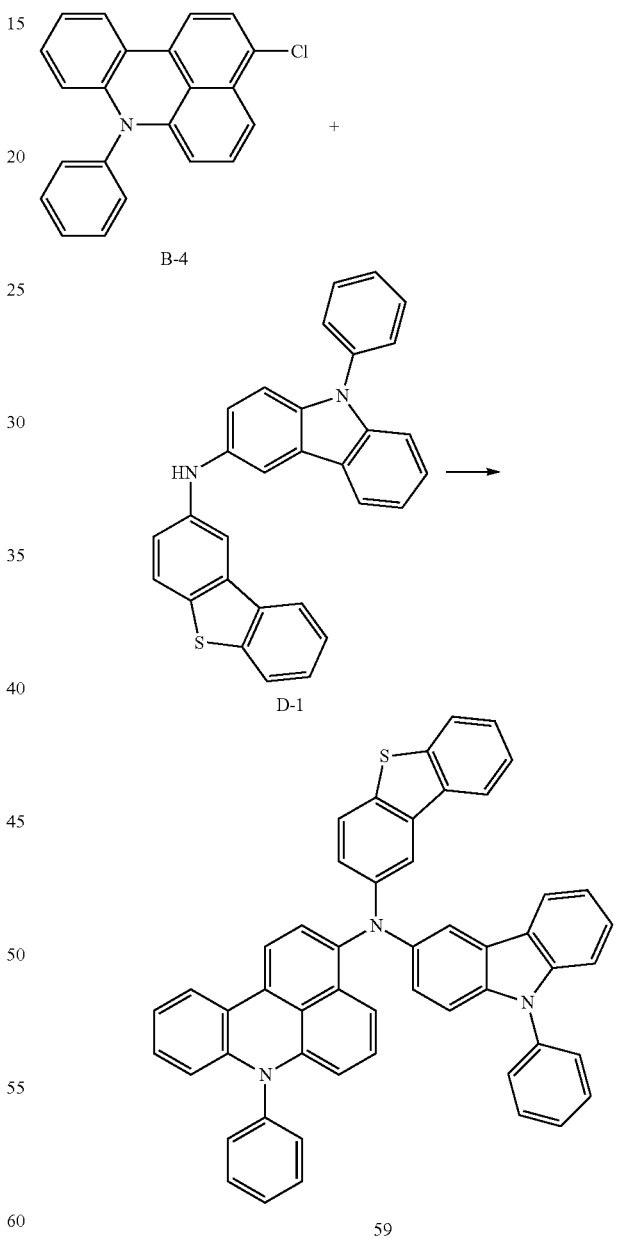

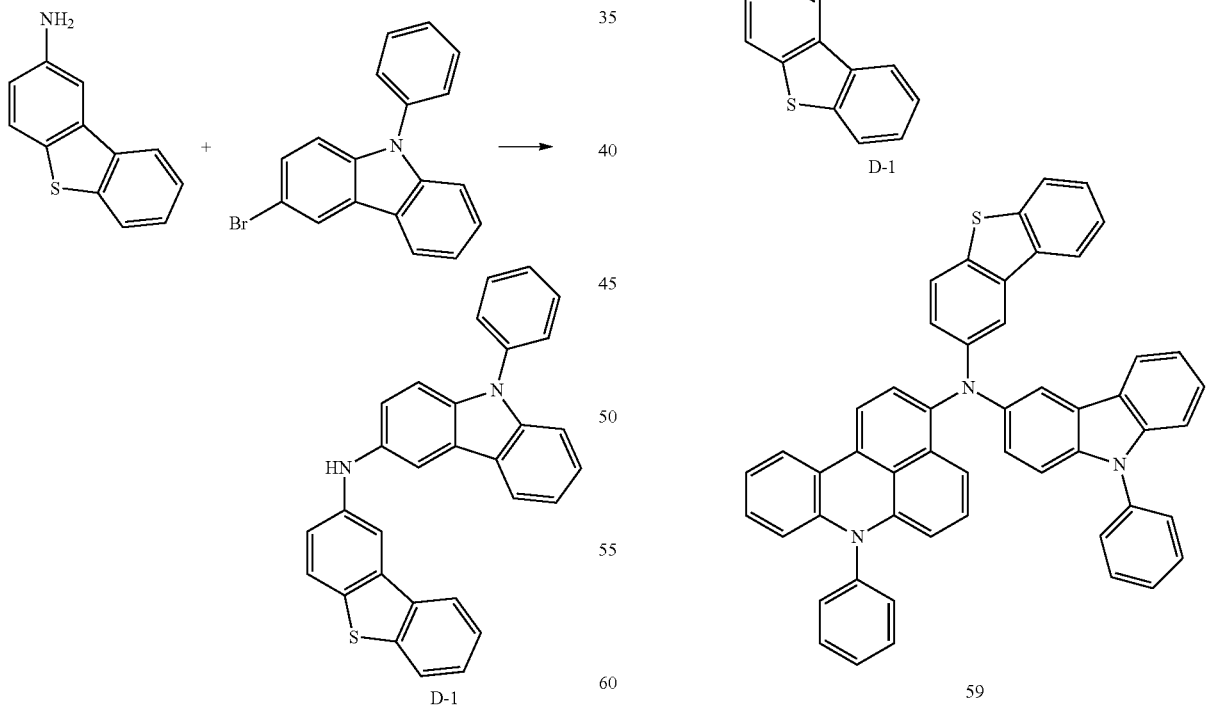

Synthesis of Intermediate D-1

5.98 g (30 mmol) of dibenzothiophene-2-amine, 6.44 g (20.0 mmol) of 3-bromo-9-phenyl-9H-carbazole, 0.37 g (0.4 mmol) of $Pd_2(dba)_3$, 0.08 g (0.4 mmol) of $P(tBu)_3$, and 5.76 g (60 mmol) of KOtBu were dissolved in 200 mL of toluene, Synthesis of Compound 59

2.93 g (yield: 80%) of Compound 59 was obtained in the same (or substantially the same) manner as in Synthesis of Compound 10, except that 1.64 g (5 mmol) of Intermediate B-4 and 2.20 g (5 mmol) of Intermediate D-1 were used instead of Intermediate A-4 and Intermediate C-1, respectively. The prepared compound was identified by LC-MS and NMR.

($C_{52}H_{33}N_3S$: M+ 731.92)

Synthesis Example 11: Synthesis of Compound 66

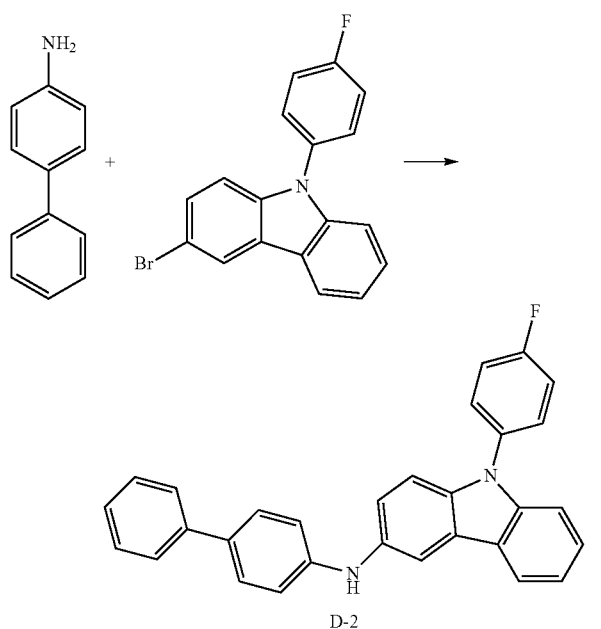

D-2

Synthesis of Intermediate D-2

5.08 g (30 mmol) of [1,1'-biphenyl]-4-amine, 6.80 g (20.0 mmol) of 3-bromo-9-(4-fluorophenyl)-9H-carbazole, 0.37 g (0.4 mmol) of $Pd_2(dba)_3$, 0.08 g (0.4 mmol) of $P(tBu)_3$, and 5.76 g (60 mmol) of KOtBu were dissolved in 150 mL of toluene, and then, the resulting mixed solution was stirred at a temperature of 85° C. for 4 hours. After the obtained reaction solution was cooled to room temperature, an extraction process was performed thereon three times using 50 mL of water and 50 mL of diethylether. An organic layer obtained from the resulting solution was dried using magnesium sulfate, and a solvent was removed therefrom by evaporation. The residue obtained therefrom was separation-purified by silica gel column chromatography, thereby completing the preparation of 7.28 g (yield: 85%) of Intermediate D-2. The prepared compound was identified by LC-MS.

($C_{30}H_{21}FN_2$: M+ 428.51)

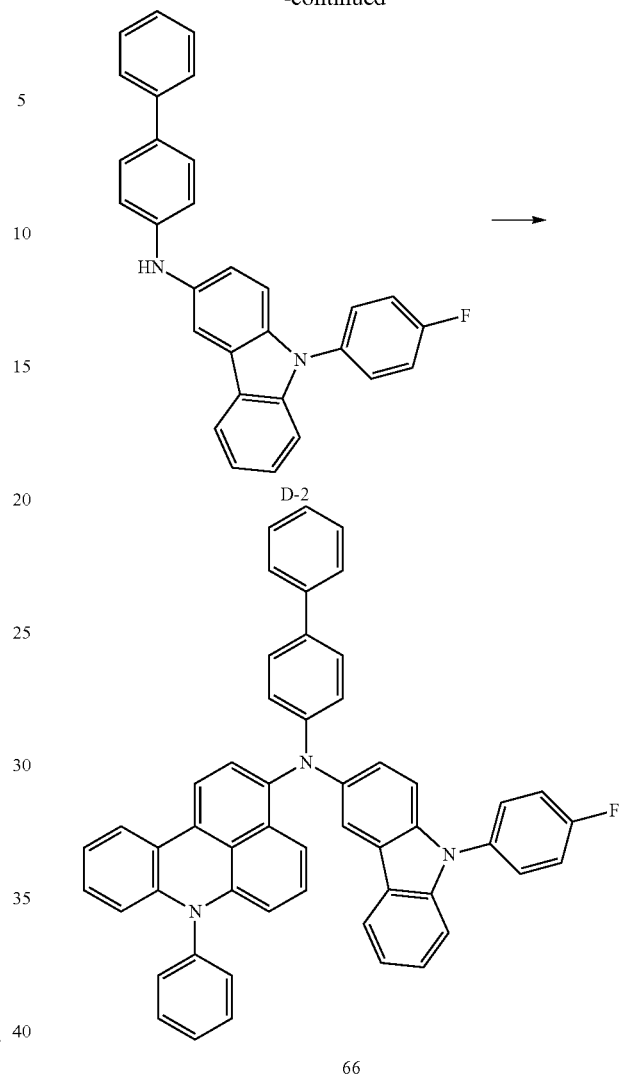

Synthesis of Compound 66

2.95 g (yield: 82%) of Compound 66 was obtained in the same (or substantially the same) manner as in Synthesis of Compound 10, except that 1.64 g (5 mmol) of Intermediate B-4 and 2.14 g (5 mmol) of Intermediate D-2 were used instead of Intermediate A-4 and Intermediate C-1, respectively. The prepared compound was identified by LC-MS and NMR. ($C_{52}H_{34}FN_3$: M+ 719.86)

Synthesis Example 12: Synthesis of Compound 69

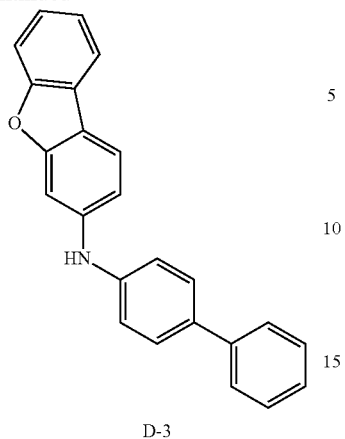

D-3

Synthesis of Intermediate D-3

5.08 g (30 mmol) of [1,1'-biphenyl]-4-amine, 4.94 g (20.0 mmol) of 3-bromodibenzo[b,d]furan, 0.37 g (0.4 mmol) of Pd$_2$(dba)$_3$, 0.08 g (0.4 mmol) of P(tBu)$_3$, and 5.76 g (60 mmol) of KOtBu were dissolved in 150 mL of toluene, and then, the resulting mixed solution was stirred at a temperature of 85° C. for 4 hours. After the obtained reaction solution was cooled to room temperature, an extraction process was performed thereon three times using 50 mL of water and 50 mL of diethylether. An organic layer obtained from the resulting solution was dried using magnesium sulfate, and a solvent was removed therefrom by evaporation. The residue obtained therefrom was separation-purified by silica gel column chromatography, thereby completing the preparation of 5.84 g (yield: 87%) of Intermediate D-3. The prepared compound was identified by LC-MS.

(C$_{24}$H$_{17}$NO: M+ 335.41)

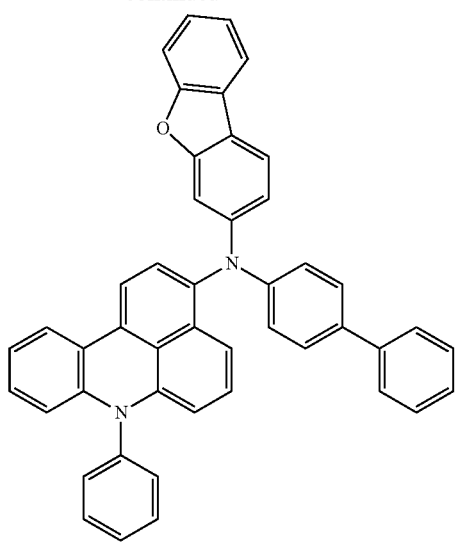

69

Synthesis of Compound 69

2.60 g (yield: 83%) of Compound 69 was obtained in the same (or substantially the same) manner as in Synthesis of Compound 10, except that 1.64 g (5 mmol) of Intermediate B-4 and 1.68 g (5 mmol) of Intermediate D-3 were used instead of Intermediate A-4 and Intermediate C-1, respectively. The prepared compound was identified by LC-MS and NMR. (C$_{46}$H$_{30}$N$_2$O: M+ 626.76)

Synthesis Example 13: Synthesis of Compound 82

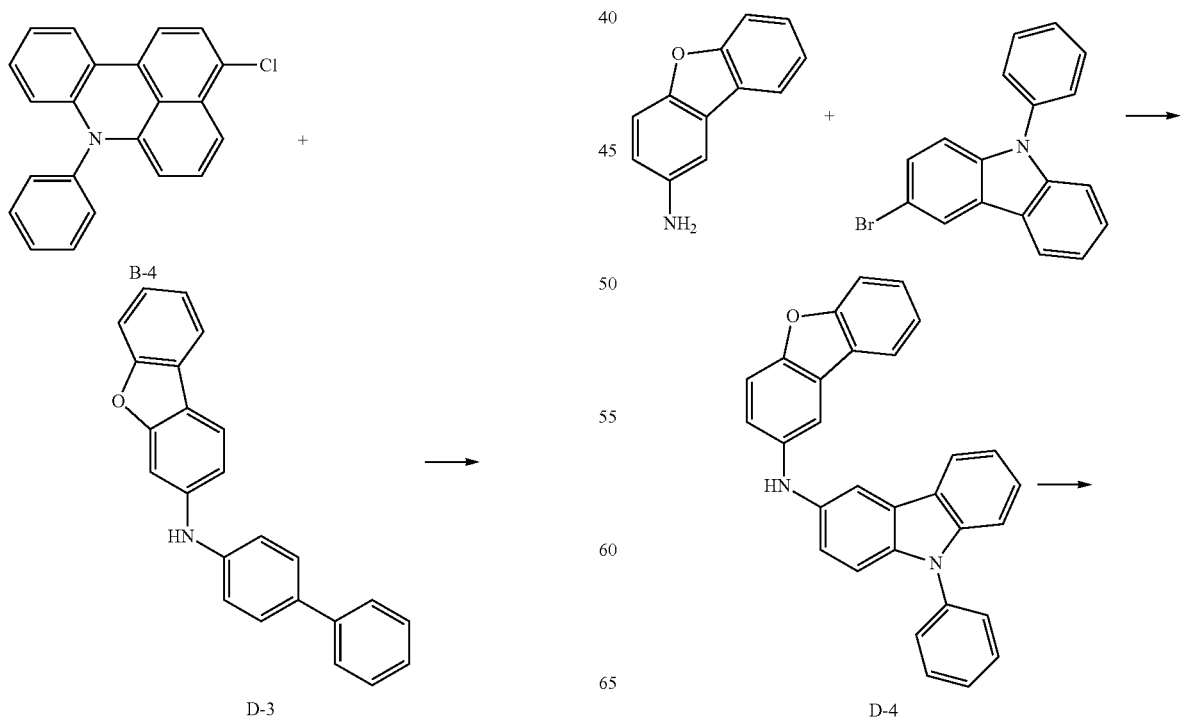

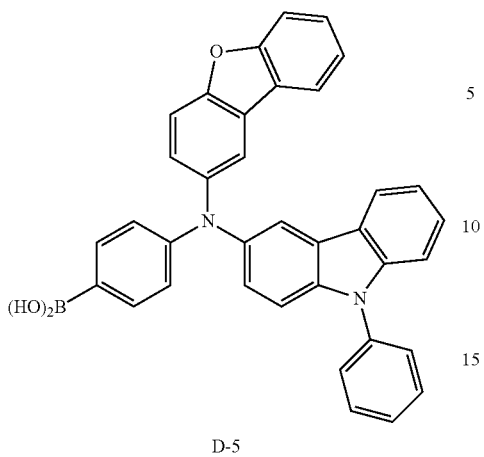

D-5

Synthesis of Intermediate D-4

5.50 g (30 mmol) of dibenzo[b,d]furan-2-amine, 6.44 g (20.0 mmol) of 3-bromo-9-phenyl-9H-carbazole, 0.37 g (0.4 mmol) of $Pd_2(dba)_3$, 0.08 g (0.4 mmol) of $P(tBu)_3$, and 5.76 g (60 mmol) of KOtBu were dissolved in 150 mL of toluene, and then, the resulting mixed solution was stirred at a temperature of 85° C. for 4 hours. After the obtained reaction solution was cooled to room temperature, an extraction process was performed thereon three times using 50 mL of water and 50 mL of diethylether. An organic layer obtained from the resulting solution was dried using magnesium sulfate, and a solvent was removed therefrom by evaporation. The residue obtained therefrom was separation-purified by silica gel column chromatography, thereby completing the preparation of 7.13 g (yield: 84%) of Intermediate D-4. The prepared compound was identified by LC-MS. ($C_{30}H_{20}N_2O$: M+ 424.50)

Synthesis of Intermediate D-5

8.17 g (yield: 75%) of Intermediate D-5 was obtained in the same (or substantially the same) manner as in Synthesis of Intermediate C-6, except that 8.49 g (20 mmol) of Intermediate D-4 was used instead of Intermediate C-5. The prepared compound was identified by LC-MS.

($C_{36}H_{25}BN_2O_3$: M+ 544.42)

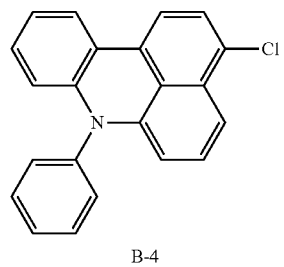

B-4

+

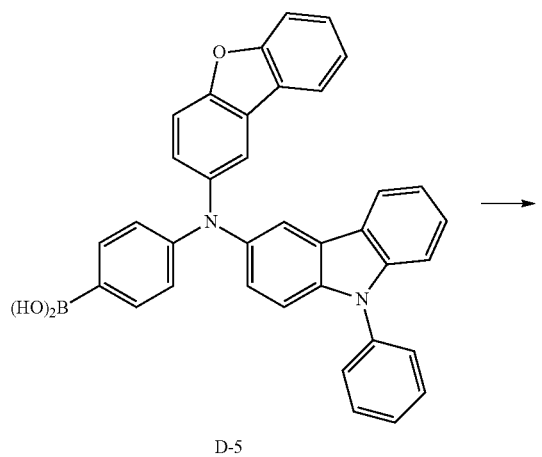

D-5

→

82

Synthesis of Compound 82

3.01 g (yield: 76%) of Compound 82 was obtained in the same (or substantially the same) manner as in Synthesis of Compound 29, except that 2.72 g (5 mmol) of Intermediate D-5 was used instead of Intermediate C-6, and Intermediate B-4 was used instead of Intermediate A-4. The prepared compound was identified by LC-MS and NMR.

($C_{58}H_{37}N_3O$: M+ 791.95)

Synthesis Example 14: Synthesis of Compound 84

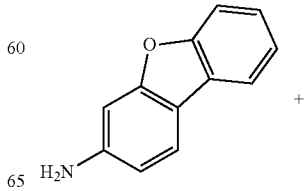

+

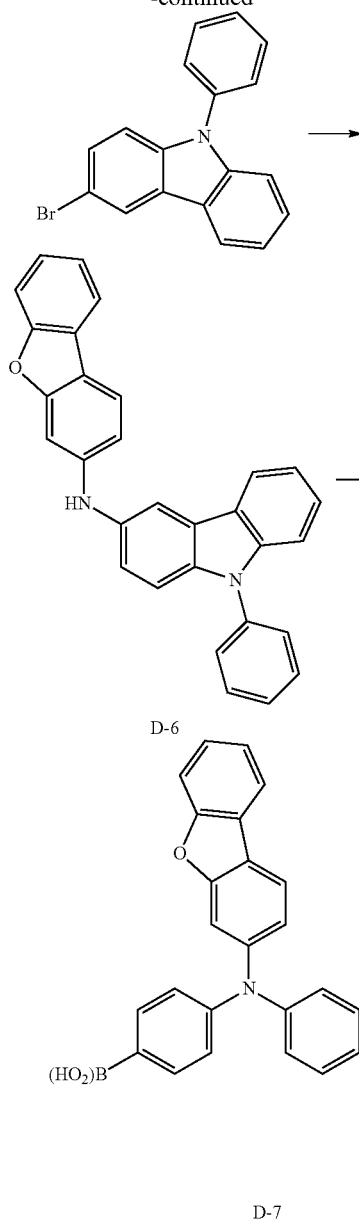

D-6

D-7

Synthesis of Intermediate D-6

5.50 g (30 mmol) of dibenzo[b,d]furan-3-amine, 6.44 g (20.0 mmol) of 3-bromo-9-phenyl-9H-carbazole, 0.37 g (0.4 mmol) of $Pd_2(dba)_3$, 0.08 g (0.4 mmol) of $P(tBu)_3$, and 5.76 g (60 mmol) of KOtBu were dissolved in 150 mL of toluene, and then, the resulting mixed solution was stirred at a temperature of 85° C. for 4 hours. After the obtained reaction solution was cooled to room temperature, an extraction process was performed thereon three times using 50 mL of water and 50 mL of diethylether. An organic layer obtained from the resulting solution was dried using magnesium sulfate, and a solvent was removed therefrom by evaporation. The residue obtained therefrom was separation-purified by silica gel column chromatography, thereby completing the preparation of 6.79 g (yield: 80%) of Intermediate D-6. The prepared compound was identified by LC-MS.

($C_{30}H_{20}N_2O$: M+ 424.50)

Synthesis of Intermediate D-7

7.73 g (yield: 71%) of Intermediate D-7 was obtained in the same (or substantially the same) manner as in Synthesis of Intermediate C-6, except that 8.49 g (20 mmol) of Intermediate D-6 was used instead of Intermediate C-5. The prepared compound was identified by LC-MS.

($C_{36}H_{25}BN_2O_3$: M+ 544.42)

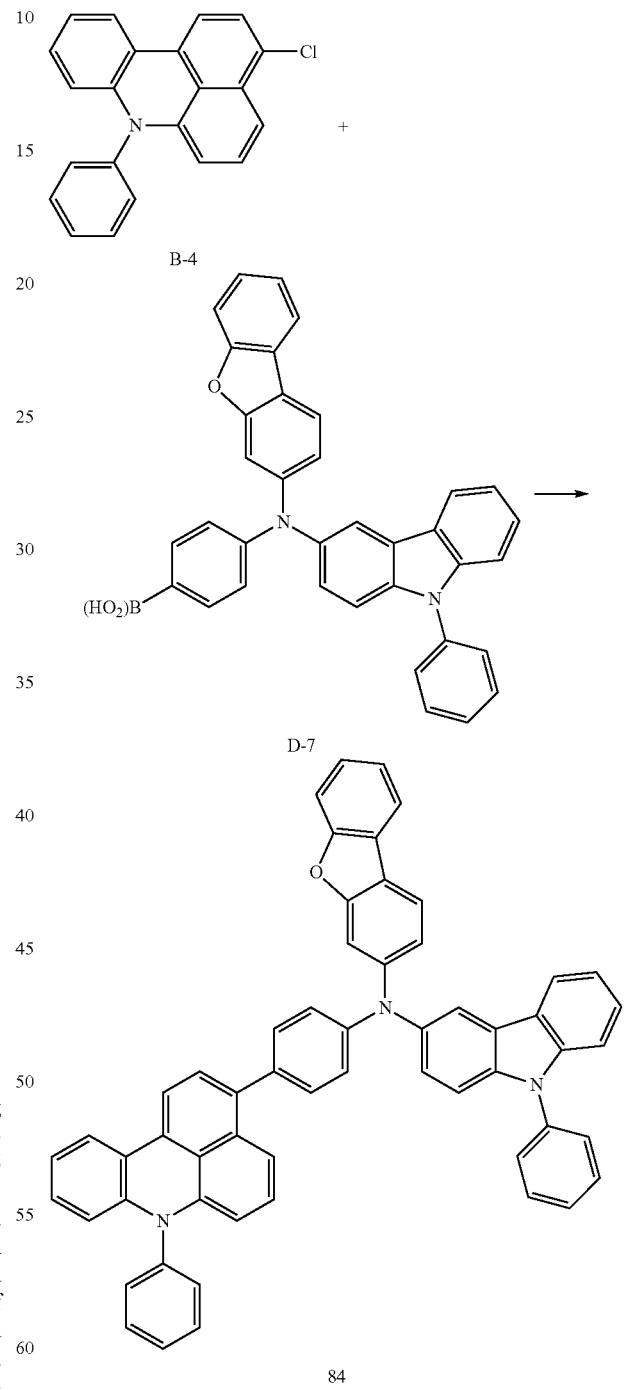

B-4

D-7

84

Synthesis of Compound 84

2.93 g (yield: 74%) of Compound 84 was obtained in the same (or substantially the same) manner as in Synthesis of Compound 29, except that 2.72 g (5 mmol) of Intermediate D-7 was used instead of Intermediate C-6. The prepared compound was identified by LC-MS and NMR. ($C_{58}H_{37}N_3O$: M+ 791.95)

Synthesis Example 15: Synthesis of Compound 89

Synthesis of Intermediate D-8

5.08 g (30 mmol) of [1,1'-biphenyl]-4-amine, 7.45 g (20.0 mmol) of 3-bromo-9-(naphthalen-2-yl)-9H-carbazole, 0.37 g (0.4 mmol) of $Pd_2(dba)_3$, 0.08 g (0.4 mmol) of $P(tBu)_3$, and 5.76 g (60 mmol) of KOtBu were dissolved in 150 mL of toluene, and then, the resulting mixed solution was stirred at a temperature of 85° C. for 4 hours. After the obtained reaction solution was cooled to room temperature, an extraction process was performed thereon three times using 50 mL of water and 50 mL of diethylether. An organic layer obtained from the resulting solution was dried using magnesium sulfate, and a solvent was removed therefrom by evaporation. The residue obtained therefrom was separation-purified by silica gel column chromatography, thereby completing the preparation of 6.91 g (yield: 75%) of Intermediate D-8. The prepared compound was identified by LC-MS.

($C_{34}H_{24}N_2$: M+ 460.58)

Synthesis of Intermediate D-9

8.48 g (yield: 73%) of Intermediate D-9 was obtained in the same (or substantially the same) manner as in Synthesis of Intermediate C-6, except that 9.21 g (20 mmol) of Intermediate D-8 was used instead of Intermediate C-5 The prepared compound was identified by LC-MS.

($C_{40}H_{29}BN_2O_2$: M+ 580.49)

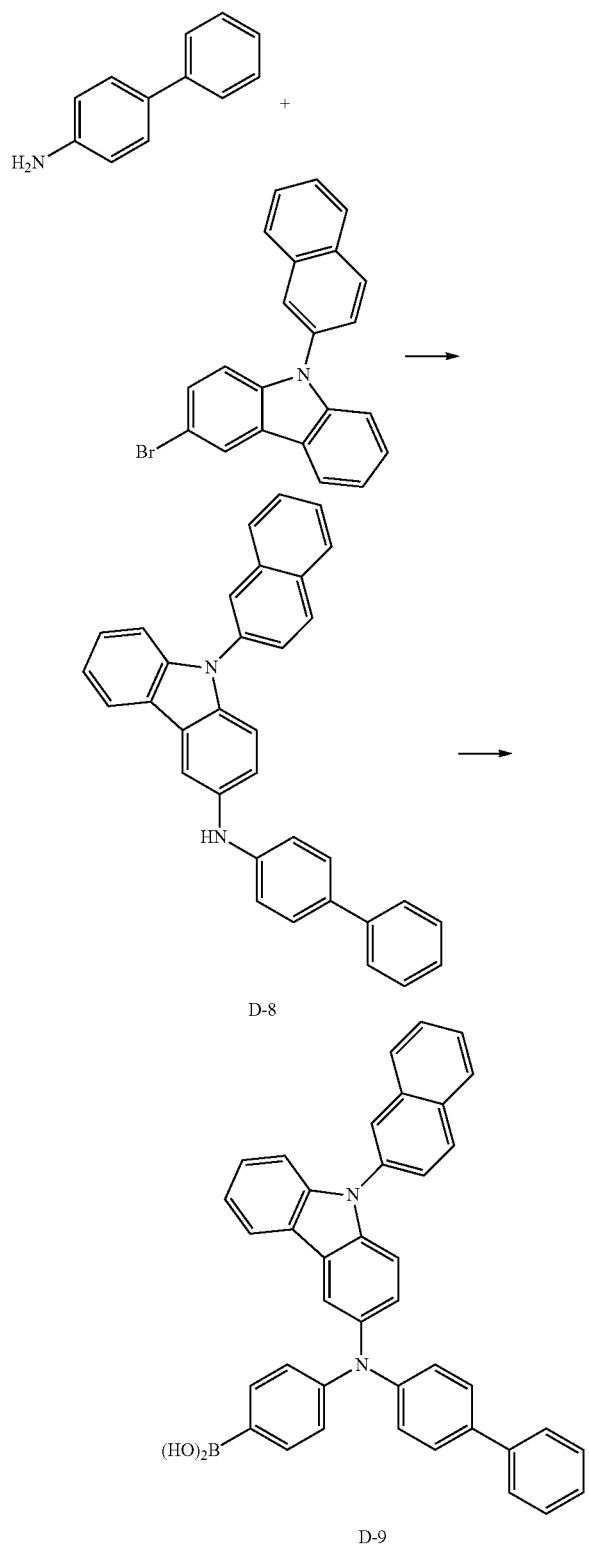

Synthesis of Compound 89

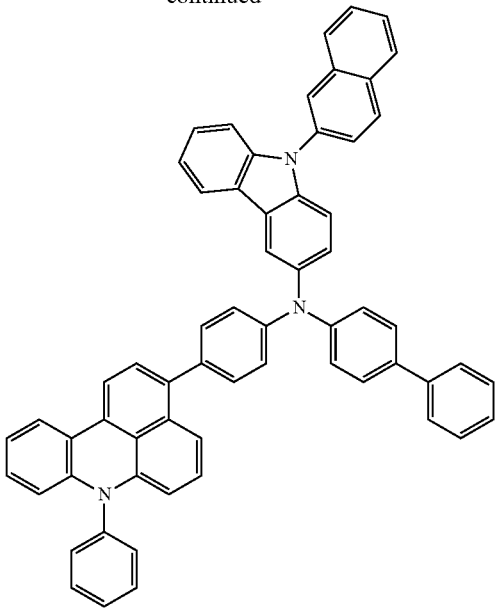

89

3.23 g (yield: 78%) of Compound 89 was obtained in the same (or substantially the same) manner as in Synthesis of Compound 29, except that 2.90 g (5 mmol) of Intermediate D-9 was used instead of Intermediate C-6, and Intermediate B-4 was used instead of Intermediate A-4. The prepared compound was identified by LC-MS and NMR. ($C_{62}H_{41}N_3$: M+ 828.03)

The compounds synthesized according to Synthesis Examples 1 to 15 were identified by $^1$H NMR and mass spectrometry/fast atom bombardment (MS/FAB), and results are shown in Table 1 below.

TABLE 1

| Compound | $^1$H NMR (CDCl$_3$, 400 MHz) | MS/FAB found | MS/FAB calc. |
|---|---|---|---|
| 10 | 8.21 (d, 1H), 8.03 (d, 1H), 7.82 (1H, d), 7.67 (dd, 2H), 7.67-7.49 (m, 7H), 7.40-7.36 (m, 6H), 7.30-7.24 (m, 5H), 7.11-7.07 (m, 3H), 6.94 (d, 1h), 6.62-6.57 (m, 2H), 6.40-6.37 (m, 2H), 6.19 (dd, 2H) | 715.86 | 715.26 |
| 14 | 8.21 (d, 1H), 8.03 (d, 1H), 7.85 (d, 1H), 7.67 (dd, 2H), 7.57-7.49 (m, 5H), 7.44-7.29 (m, 5H), 7.27-7.07 (m, 19H), 6.96 (d, 1H), 6.80 (d, 1H), 6.67-6.61 (m, 3H), 6.35-6.31 (m, 2H), 6.19 (dd, 2H) | 866.08 | 865.35 |
| 18 | 8.21 (d, 1H), 8.03 (d, 1H), 7.85 (d, 1H), 7.67 (dd, 2H), 7.57 (d, 1H), 7.50-7.48 (m, 4H), 7.44-7.29 (m, 5H), 7.27-7.23 (m, 10H), 7.23-7.07 (m, 9H), 6.96 (d, 1H), 6.80 (d, 1H), 6.67-6.61 (m, 3H), 6.35-6.31 (m, 2H), 6.19 (dd, 2H) | 719.86 | 719.27 |
| 22 | 8.03 (d, 1H), 7.76 (d, 1H), 7.67 (dd, 2H), 7.58-7.56 (m, 3H), 7.46-7.45 (m, 5H), 7.37-7.24 (m, 4H), 7.11-7.07 (m, 5H), 6.67-6.73 (m, 2H), 6.62-6.35 (m, 5H), 6.19 (dd, 2H), 1.61 (m, 6H) | 652.84 | 652.29 |
| 29 | 8.21 (d, 1H), 7.92 (d, 1H), 7.80-7.77 (m, 3H), 7.67-7.57 (m, 7H), 7.50-7.24 (m, 20H), 7.15-7.07 (m, 3H), 6.84 (d, 2H), 6.70-6.48 (m, 6H) | 854.07 | 853.35 |
| 36 | 8.21 (d, 1H), 7.92 (d, 1H), 7.81-7.79 (m, 4H), 7.67 (dd, 2H), 7.57-7.49 (m, 6H), 7.43-7.36 (m, 7H), 7.30-7.23 (m, 5H), 7.15-7.03 (m, 5H), 6.79 (d, 2H), 6.62-6.57 (m, 2H), 6.48 (dd, 2H) | 791.95 | 791.29 |
| 41 | 8.25 (d, 1H), 7.92-7.87 (m, 3H), 7.80-7.79 (d, 2H), 7.71-7.67 (m, 3H), 7.57-7.51 (m, 6H), 7.46-7.42 (m, 8H), 7.38-7.37 (m, 4H), 7.27-7.25 (m, 3H), 7.15-7.07 (m, 3H), 6.66-6.59 (m, 6H), 6.48 (dd, 2H) | 828.03 | 827.33 |
| 48 | 7.92-7.88 (m, 4H), 7.80-7.79 (d, 2H), 7.67-7.65 (d, 2H), 7.57-7.54 (m, 3H), 7.46-7.42 (m, 10H), 7.37-7.15 (m, 7H), 7.07-7.05 (m, 2H), 6.85-6.74 (m, 4H), 6.62-6.46 (m, 8H) | 851.07 | 850.33 |
| 54 | 8.21 (d, 1H), 7.99-7.97 (d, 2H), 7.86-7.76 (d, 2H), 7.68-7.50 (m, 7H), 7.49-7.37 (m, 8H), 7.36-7.04 (m, 10H), 7.01-6.62 (m, 4H), 6.52-6.50 (m, 2H), 6.40-6.38 (d, 1H) | 751.93 | 751.30 |

TABLE 1-continued

| Compound | $^1$H NMR (CDCl$_3$, 400 MHz) | MS/FAB found | calc. |
|---|---|---|---|
| 59 | 8.21 (d, 1H), 8.05 (d, 1H), 7.88-7.70 (m, 4H), 7.67-7.60 (m, 2H), 7.53-7.44 (m, 6H), 7.41-7.22 (m, 7H), 7.13-7.01 (m, 6H), 6.85-6.81 (m, 2H), 6.62-6.60 (m, 2H), 6.52-6.50 (m, 2H) | 731.92 | 731.24 |
| 66 | 8.21 (d, 1H), 7.88 (d, 1H), 7.76 (d, 1H), 7.67 (d, 1H), 7.57-7.55 (m, 2H), 7.46-7.22 (m, 13H), 7.13-7.01 (m, 8H), 6.91-6.88 (m, 2H), 6.62-6.52 (m, 5H) | 719.86 | 719.27 |
| 69 | 7.88 (d, 1H), 7.81 (d, 1H), 7.76 (d, 2H), 7.67 (d, 1H), 7.57-7.53 (m, 3H), 7.46-7.43 (m, 4H), 7.38-7.36 (m, 2H), 7.23-7.21 (m, 2H), 7.13-7.01 (m, 8H), 6.91 (d, 1H), 6.65-6.62 (m, 3H), 6.52-6.50 (m, 2H) | 626.76 | 626.24 |
| 82 | 8.21 (d, 1H), 8.09 (d, 1H), 7.82-7.80 (d, 2H), 7.63 (d, 1H), 7.53-7.49 (m, 8H), 7.40-7.00 (m, 18H), 6.62-6.60 (m, 4H), 6.52-6.50 (m, 2H) | 791.95 | 791.29 |
| 84 | 8.21 (d, 1H), 8.09 (d, 1H), 7.81-7.79 (m, 3H), 7.63 (d, 1H), 7.53-7.48 (m, 7H), 7.39-7.23 (m, 10H), 7.16-7.01 (m, 8H), 6.73-6.71 (m, 2H), 6.62-6.52 (m, 4H) | 791.95 | 791.29 |
| 89 | 8.25 (d, 1H), 8.09 (d, 1H), 7.79-7.87 (m, 2H), 7.80-7.71 (m, 2H), 7.63-7.25 (m, 21H), 7.16-7.02 (m, 6H), 6.65-6.52 (m, 8H) | 828.03 | 827.33 |

Example 1

An anode was prepared by cutting an indium tin oxide (ITO) glass substrate (manufactured by Corning Inc.) on which ITO was formed to a thickness of 15 Ω/cm$^2$ (1,200 Å) to a size of 50 mm×50 mm×0.7 mm, ultrasonically cleaning the ITO glass substrate using isopropyl alcohol and pure water, for 5 minutes in each, and then, exposing to irradiation of UV light for 30 minutes and ozone to clean. Then, the obtained ITO glass substrate was loaded into a vacuum deposition apparatus.

2-TNATA was vacuum deposited on the ITO glass substrate to form a hole injection layer having a thickness of 600 Å, and then, Compound 10 was vacuum deposited on the hole injection layer to form a hole transport layer having a thickness of 300 Å, thereby forming a hole transport region.

9,10-di-naphthalene-2-yl-anthracene (ADN) and N,N,N′, N′-tetraphenyl-pyrene-1,6-diamine (TPD) were co-deposited on the hole transport region at a weight ratio of 98:2 to form an emission layer having a thickness of 300 Å.

Alq$_3$ was deposited on the emission layer to form an electron transport layer having a thickness of 300 Å, LiF was deposited on the electron transport layer to form an electron injection layer having a thickness of 10 Å, and Al was vacuum deposited on the electron injection layer to form a cathode (i.e., a cathode electrode) having a thickness of 3,000 Å, thereby completing the manufacture of an organic light-emitting device.

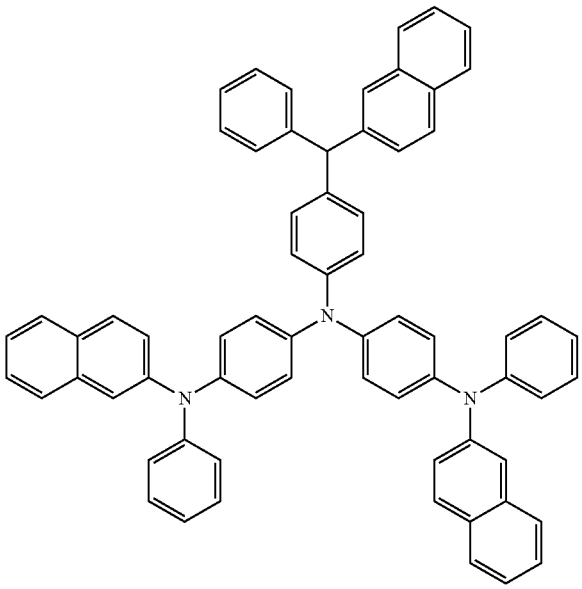

2-TNATA

-continued

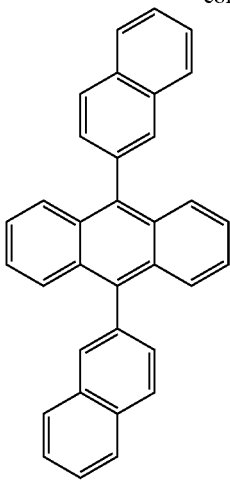

ADN

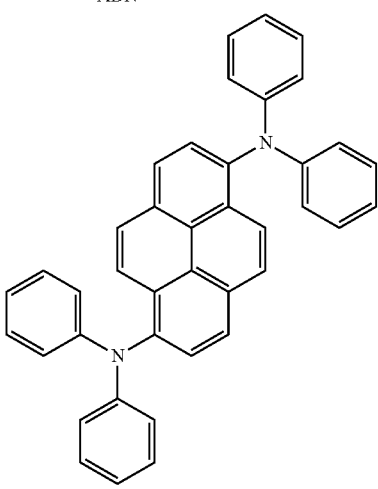

TPD

Examples 2 to 15 and Comparative Examples 1 to 3

Organic light-emitting devices were each manufactured in the same (or substantially the same) manner as in Synthesis of Example 1, except that Compounds 14, 18, 22, 29, 36, 41, 48, 54, 59, 66, 69, 82, 84, and 89, NPB, Compound A, and Compound B were used instead of Compound 10 in forming the hole transport layer.

Evaluation Example 1

The driving voltage, current density, brightness, efficiency, and half-lifespan of the organic light-emitting devices of Examples 1 to 15 and Comparative Examples 1 to 3 were evaluated by using a Keithley SMU 236 meter and a PR650 brightness measuring meter. Results thereof are shown in Table 2. Here, the half-lifespan results were obtained by measuring the time at which the brightness of the organic light-emitting device reached 50% of the initial brightness after being driven.

TABLE 2

|  | Material for forming a hole transport layer | Driving voltage (V) | Current density (mA/cm$^2$) | Brightness (cd/cm$^2$) | Efficiency (cd/A) | Emission color | Half-life span (hr @100 mA/cm$^2$) |
|---|---|---|---|---|---|---|---|
| Example 1 | Compound 10 | 5.71 | 50 | 3040 | 6.08 | Blue | 345 |
| Example 2 | Compound 14 | 5.65 | 50 | 3085 | 6.17 | Blue | 355 |
| Example 3 | Compound 18 | 5.54 | 50 | 3125 | 6.25 | Blue | 334 |
| Example 4 | Compound 22 | 5.50 | 50 | 3155 | 6.31 | Blue | 340 |
| Example 5 | Compound 29 | 5.48 | 50 | 3110 | 6.22 | Blue | 325 |
| Example 6 | Compound 36 | 5.39 | 50 | 3210 | 6.42 | Blue | 351 |
| Example 7 | Compound 41 | 5.43 | 50 | 3170 | 6.34 | Blue | 338 |
| Example 8 | Compound 48 | 5.53 | 50 | 3135 | 6.27 | Blue | 375 |
| Example 9 | Compound 54 | 5.70 | 50 | 3060 | 6.12 | Blue | 348 |
| Example 10 | Compound 59 | 5.68 | 50 | 3095 | 6.19 | Blue | 342 |
| Example 11 | Compound 66 | 5.65 | 50 | 3120 | 6.24 | Blue | 352 |
| Example 12 | Compound 69 | 5.60 | 50 | 3190 | 6.38 | Blue | 364 |
| Example 13 | Compound 82 | 5.40 | 50 | 3275 | 6.55 | Blue | 365 |
| Example 14 | Compound 84 | 5.42 | 50 | 3235 | 6.47 | Blue | 378 |
| Example 15 | Compound 89 | 5.51 | 50 | 3210 | 6.42 | Blue | 342 |
| Comparative Example 1 | NPB | 7.01 | 50 | 2645 | 5.29 | Blue | 258 |
| Comparative Example 2 | Compound A | 7.24 | 50 | 2550 | 5.10 | Blue | 243 |
| Comparative Example 3 | Compound B | 6.28 | 50 | 3020 | 6.04 | Blue | 284 |

10
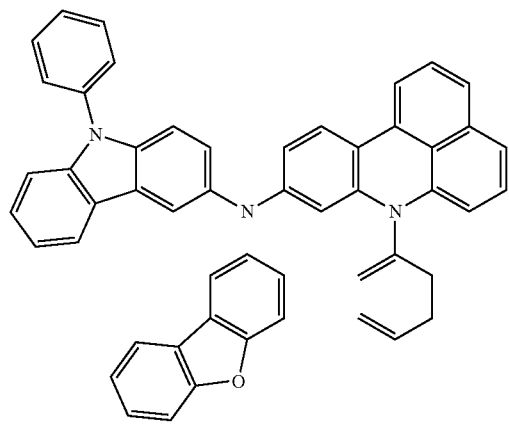
14
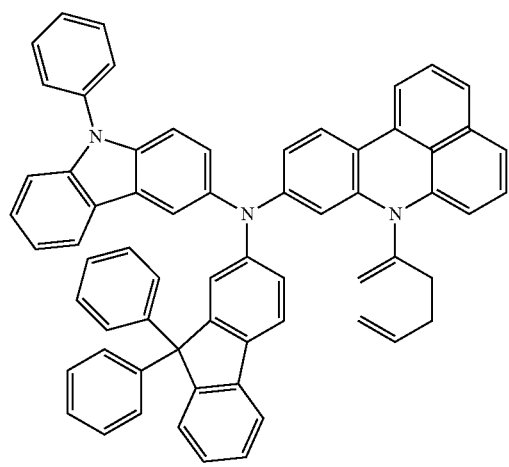
18
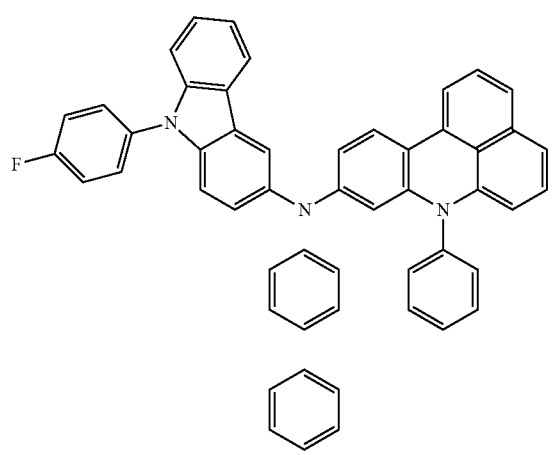
22
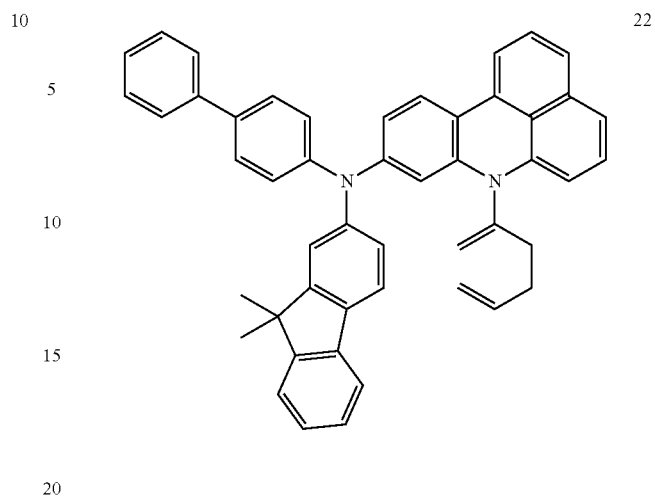
29
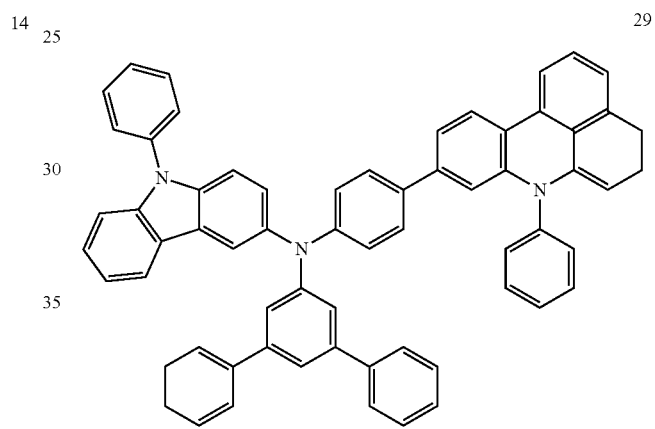
36
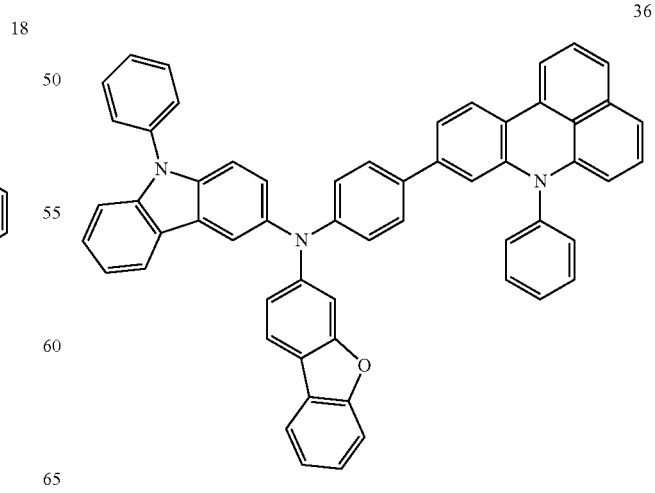

41
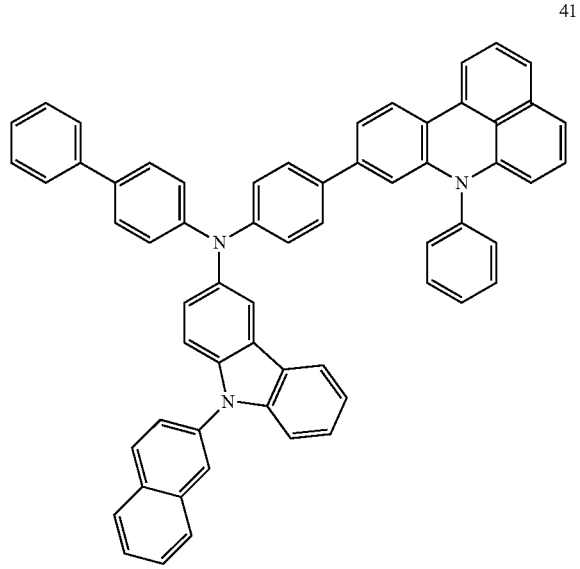
48
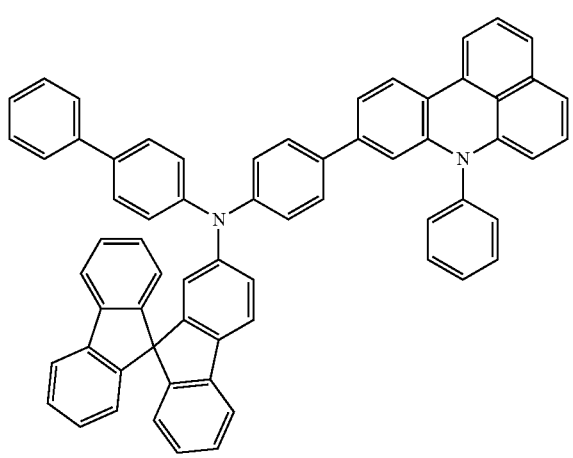
54
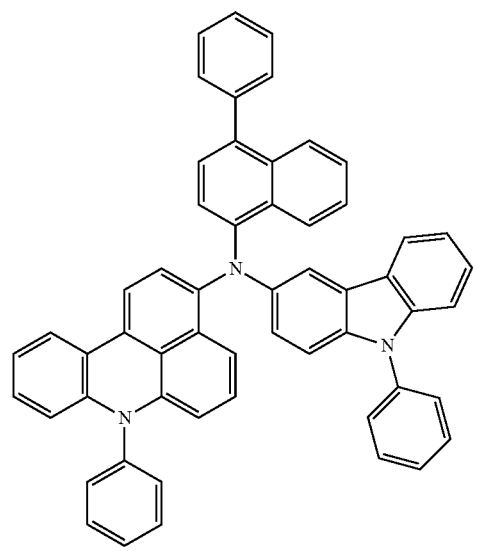
59
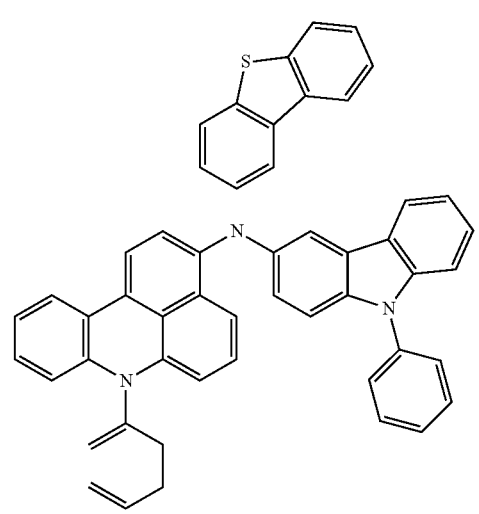
66
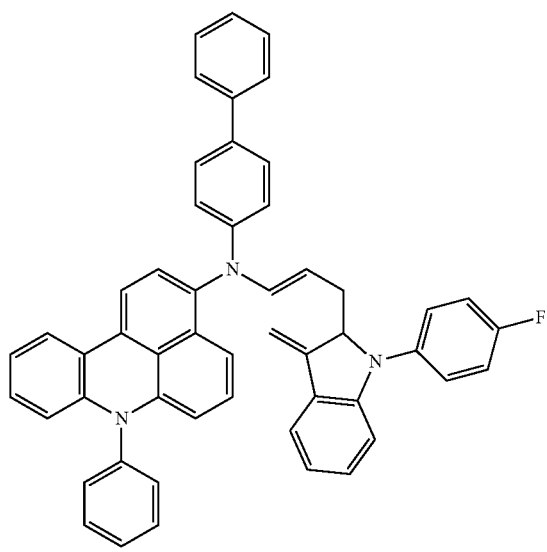
69
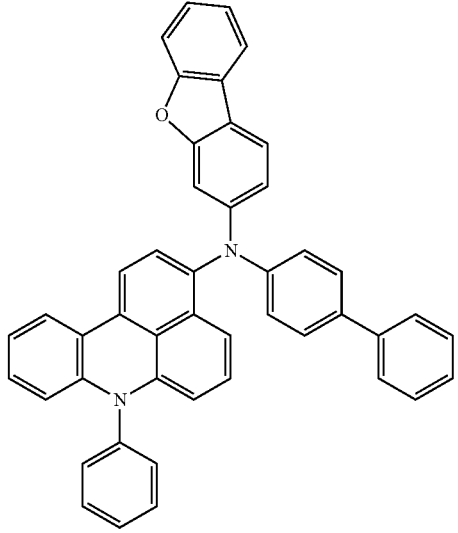

-continued
82
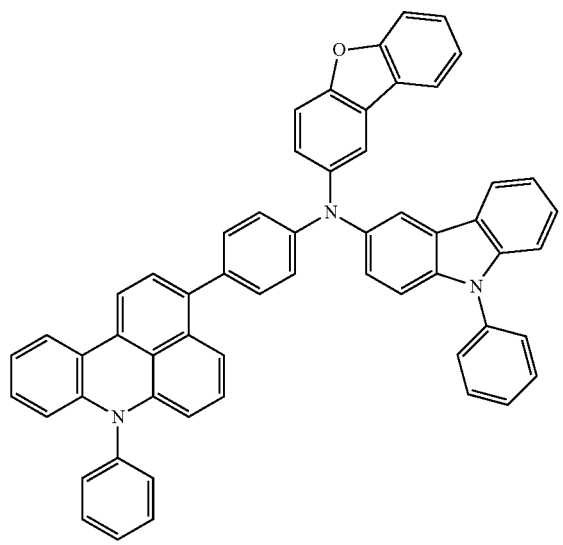
89
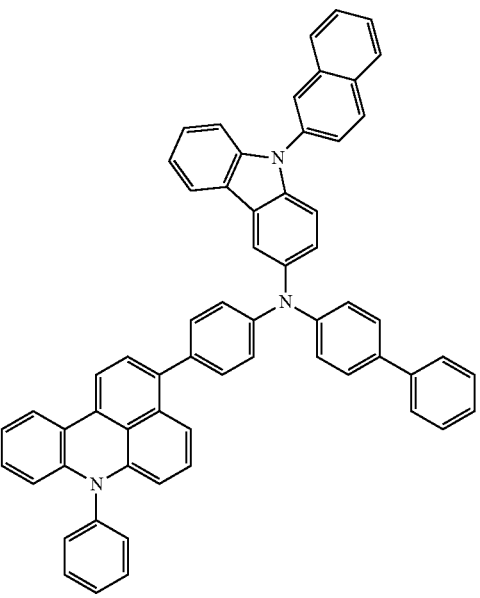
Compound A
Compound B
84
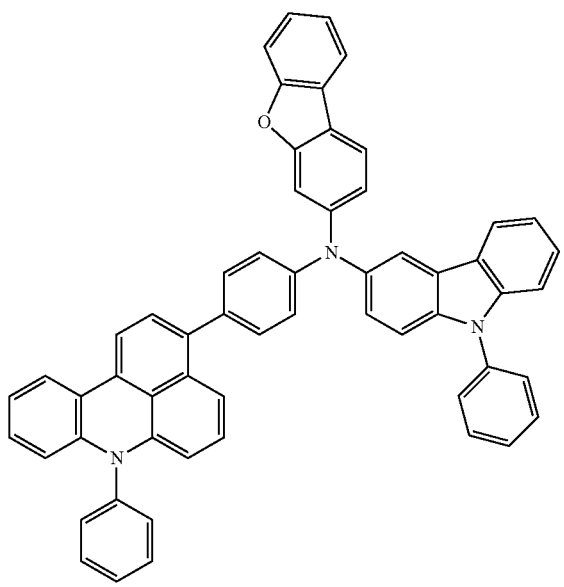
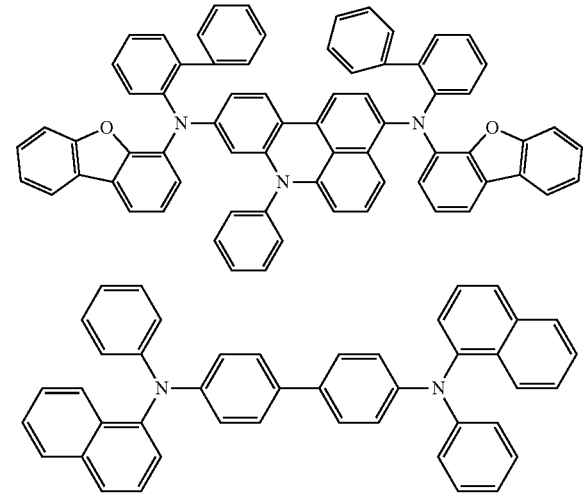
NPB
Referring to the results shown in Table 2, it can be seen that the organic light-emitting devices of Examples 1 to 15 had low driving voltage and improved brightness, efficiency, and half-lifespans, as compared to those of the organic light-emitting devices of Comparative Examples 1 to 3.

As used herein, the terms "use," "using," and "used" may be considered synonymous with the terms "utilize," "utilizing," and "utilized," respectively.

In addition, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

It should be understood that example embodiments described herein should be considered in a descriptive sense only and not for purposes of limitation. Descriptions of features or aspects within each example embodiment should typically be considered as available for other similar features or aspects in other example embodiments.

The novel condensed cyclic compound according to embodiments of the present disclosure may have excellent hole injection characteristics. Accordingly, the novel condensed cyclic compound is suitable for use as a hole transport material for red, green, and/or white fluorescent and/or phosphorescent devices. An organic light-emitting device including the condensed cyclic compound according to the present embodiments may have high efficiency, low driving voltage, high luminance, and a long lifespan.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the drawing, it will be understood by those of ordinary skill in the art that various changes in form and details may be made therein without departing from the spirit and scope of the present disclosure as defined by the following claims and equivalents thereof.

What is claimed is:

1. An organic light-emitting device comprising:
a first electrode;
a second electrode facing the first electrode; and
an organic layer between the first electrode and the second electrode, the organic layer comprising:
i) an emission layer,
ii) a hole transport region between the first electrode and the emission layer, the hole transport region comprising at least one selected from a hole injection layer, a hole transport layer, a buffer layer, and an electron blocking layer, and
iii) an electron transport region between the emission layer and the second electrode, the electron transport region comprising at least one selected from a hole blocking layer, an electron transport layer, and an electron injection layer,
wherein the emission layer is to emit blue fluorescence,
wherein the hole transport region comprises a condensed cyclic compound represented by Formula 1:

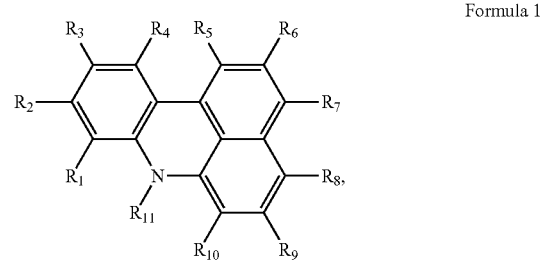

Formula 1 wherein, in Formula 1,
$R_1$ to $R_6$ and $R_8$ to $R_{11}$ are each independently selected from hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$), and
$R_7$ is a group represented by Formula 2:

Formula 2 wherein in Formula 2,
$L_1$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;
a1 is an integer selected from 0 to 3, wherein when a1 is two or more, two or more $L_1$(s) are identical to or different from each other; and Ar$_1$ and Ar$_2$ are each independently selected from a substituted or unsubstituted fluorenyl group, a substituted or unsubstituted spiro-bifluorenyl group, a substituted or unsubstituted carbazolyl group, a substituted or unsubstituted dibenzofuranyl group, a substituted or unsubstituted dibenzothiophenyl group, and a substituted or unsubstituted dibenzosilolyl group, provided that Ar$_1$ and Ar$_2$ are different from each other, and provided that at least one selected from Ar$_1$ and Ar$_2$ is a carbazolyl group substituted with a C$_6$-C$_{60}$ aryl group substituted with at least one selected from —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, and a phosphoric acid group or a salt thereof, wherein at least one substituent of the substituted fluorenyl group, substituted spiro-bifluorenyl group, substituted carbazolyl group, substituted dibenzofuranyl group, substituted dibenzothiophenyl group, substituted dibenzosilolyl group, substituted C$_3$-C$_{10}$ cycloalkylene group, substituted C$_1$-C$_{10}$ heterocycloalkylene group, substituted C$_3$-C$_{10}$ cycloalkenylene group, substituted C$_1$-C$_{10}$ heterocycloalkenylene group, substituted C$_6$-C$_{60}$ arylene group, substituted C$_1$-C$_{60}$ heteroarylene group, substituted divalent non-aromatic condensed polycyclic group, substituted divalent non-aromatic condensed heteropolycyclic group, substituted C$_1$-C$_{60}$ alkyl group, substituted C$_2$-C$_{60}$ alkenyl group, substituted C$_2$-C$_{60}$ alkynyl group, substituted C$_1$-C$_{60}$ alkoxy group, substituted C$_3$-C$_{10}$ cycloalkyl group, substituted C$_1$-C$_{10}$ heterocycloalkyl group, substituted C$_3$-C$_{10}$ cycloalkenyl group, substituted C$_1$-C$_{10}$ heterocycloalkenyl group, substituted C$_6$-C$_{60}$ aryl group, substituted C$_6$-C$_{60}$ aryloxy group, substituted C$_6$-C$_{60}$ arylthio group, substituted C$_1$-C$_{60}$ heteroaryl group, substituted monovalent non-aromatic condensed polycyclic group, and substituted monovalent non-aromatic condensed heteropolycyclic group is selected from the group consisting of:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, and a C$_1$-C$_{60}$ alkoxy group, a C$_1$-C$_{60}$ alkyl group, a C$_2$-C$_{60}$ alkenyl group, a C$_2$-C$_{60}$ alkynyl group, and a C$_1$-C$_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, and —Si(Q$_{11}$)(Q$_{12}$)(Q$_{13}$), a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, a biphenyl group, and a terphenyl group, and a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, a biphenyl group, a terphenyl group, and —Si(Q$_{21}$)(Q$_{22}$)(Q$_{23}$); and —Si(Q$_{31}$)(Q$_{32}$)(Q$_{33}$), wherein Q$_1$ to Q$_3$, Q$_{11}$ to Q$_{13}$, Q$_{21}$ to Q$_{23}$, and Q$_{31}$ to Q$_{33}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_1$-C$_{60}$ heteroaryl group, a monovalent non-aromatic condensed polycyclic group, a monovalent non-aromatic condensed heteropolycyclic group, a biphenyl group, and a terphenyl group.

2. The organic light-emitting device of claim 1, wherein L$_1$ is selected from the group consisting of:

a phenylene group, a pentalenylene group, an indenylene group, a naphthylene group, an azulenylene group, a heptalenylene group, an indacenylene group, an acenaphthylene group, a fluorenylene group, spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a benzocarbazolylene group, a dibenzocarbazolylene group, a thiadiazolylene group, an imidazopyridinylene group, and an imidazopyrimidinylene group, and a phenylene group, a pentalenylene group, an indenylene group, a naphthylene group, an azulenylene group, a heptalenylene group, an indacenylene group, an acenaphthylene group, a fluorenylene group, spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolylene group, a benzocarbazolyl group, a dibenzocarbazolyl group, a thiadiazolyl group, an imidazopyridinyl group, and an imidazopyrimidinyl group.

3. The organic light-emitting device of claim 1, wherein $L_1$ is selected from groups represented by Formula 3-1 to Formula 3-42:

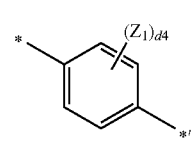

Formula 3-1

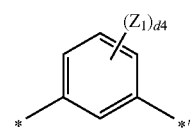

Formula 3-2

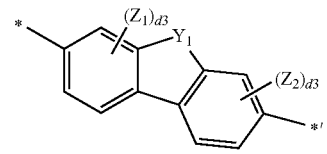

Formula 3-3

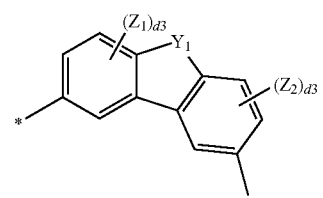

Formula 3-4

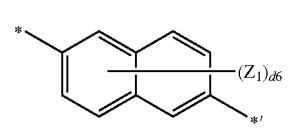

Formula 3-5

Formula 3-6
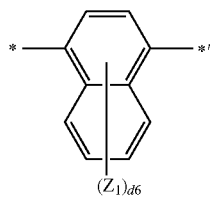
Formula 3-7
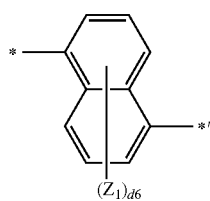
Formula 3-8
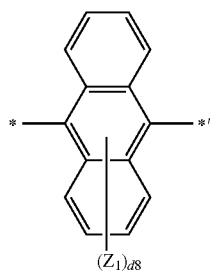
Formula 3-9
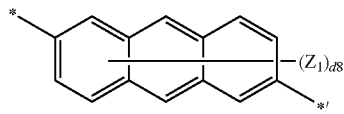
Formula 3-10
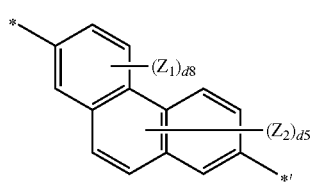
Formula 3-11
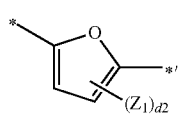
Formula 3-12
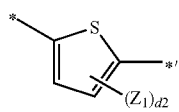
Formula 3-13
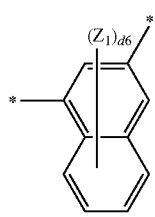
Formula 3-14
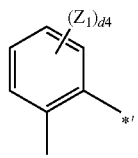
Formula 3-15
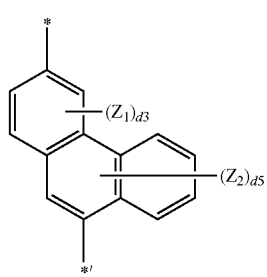
Formula 3-16
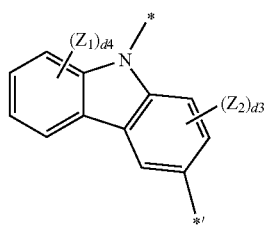
Formula 3-17
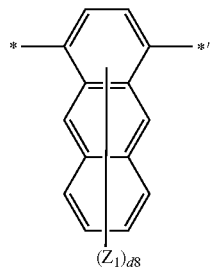
Formula 3-18
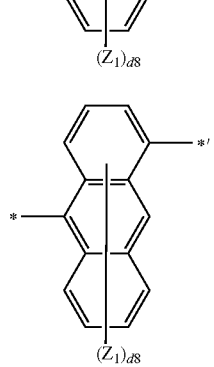
Formula 3-19
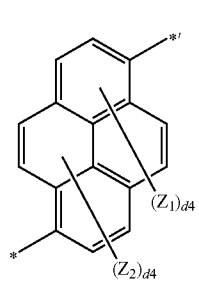

-continued
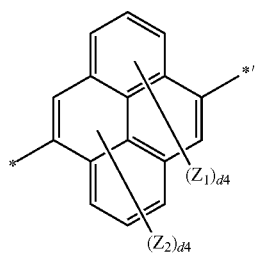
Formula 3-20
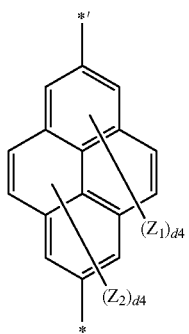
Formula 3-21
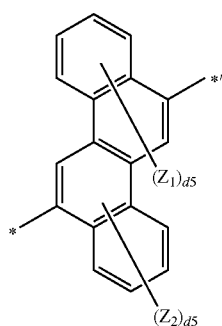
Formula 3-22
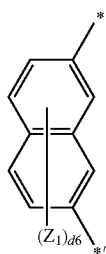
Formula 3-23
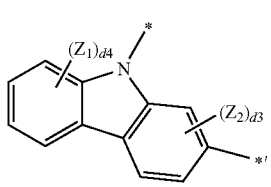
Formula 3-24
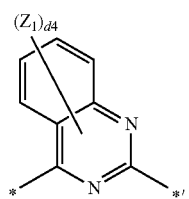
Formula 3-25
-continued
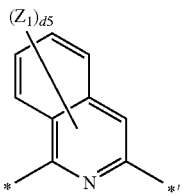
Formula 3-26
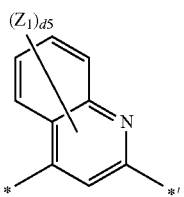
Formula 3-27
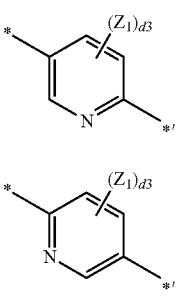
Formula 3-28
Formula 3-29
Formula 3-30
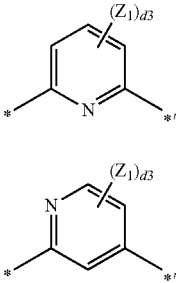
Formula 3-31
Formula 3-32
Formula 3-33
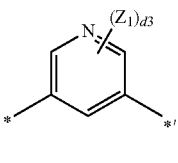
Formula 3-34
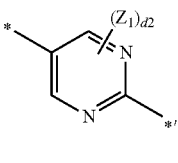
Formula 3-35
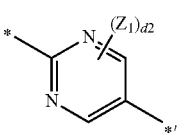

-continued

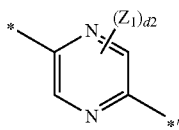
Formula 3-36

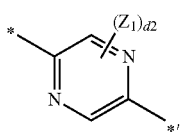
Formula 3-37

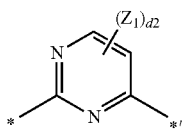
Formula 3-38

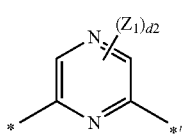
Formula 3-39

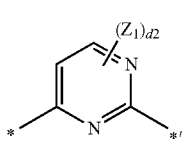
Formula 3-40

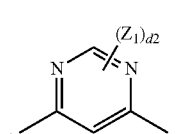
Formula 3-41

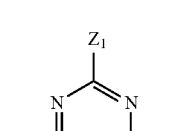
Formula 3-42 wherein, in Formula 3-1 to Formula 3-42,
$Y_1$ is selected from O, S, C($Z_3$)($Z_4$), N($Z_5$), and Si($Z_6$)($Z_7$);
$Z_1$ to $Z_7$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group;

d2 is 1 or 2;
d3 is an integer selected from 1 to 3;
d4 is an integer selected from 1 to 4;
d5 is an integer selected from 1 to 5;
d6 is an integer selected from 1 to 6;
d8 is an integer selected from 1 to 8; and
* and *' each indicate a binding site to a neighboring atom.

4. The organic light-emitting device of claim 1, wherein Li is selected from groups represented by Formula 4-1 to Formula 4-29:

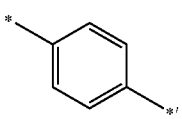
Formula 4-1

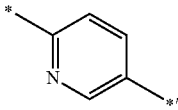
Formula 4-2

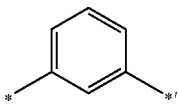
Formula 4-3

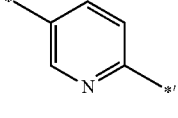
Formula 4-4

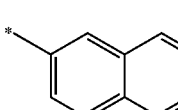
Formula 4-5

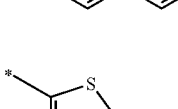
Formula 4-6

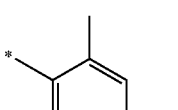
Formula 4-7

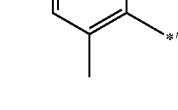
Formula 4-8

-continued
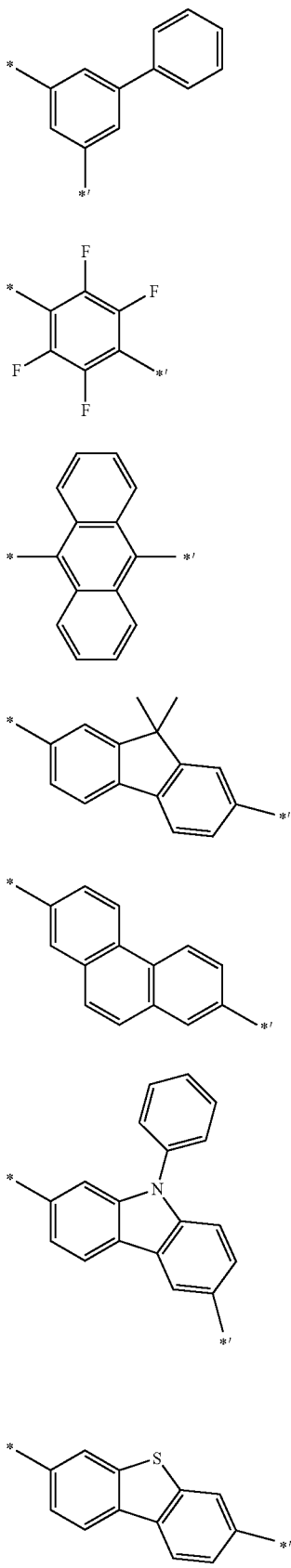
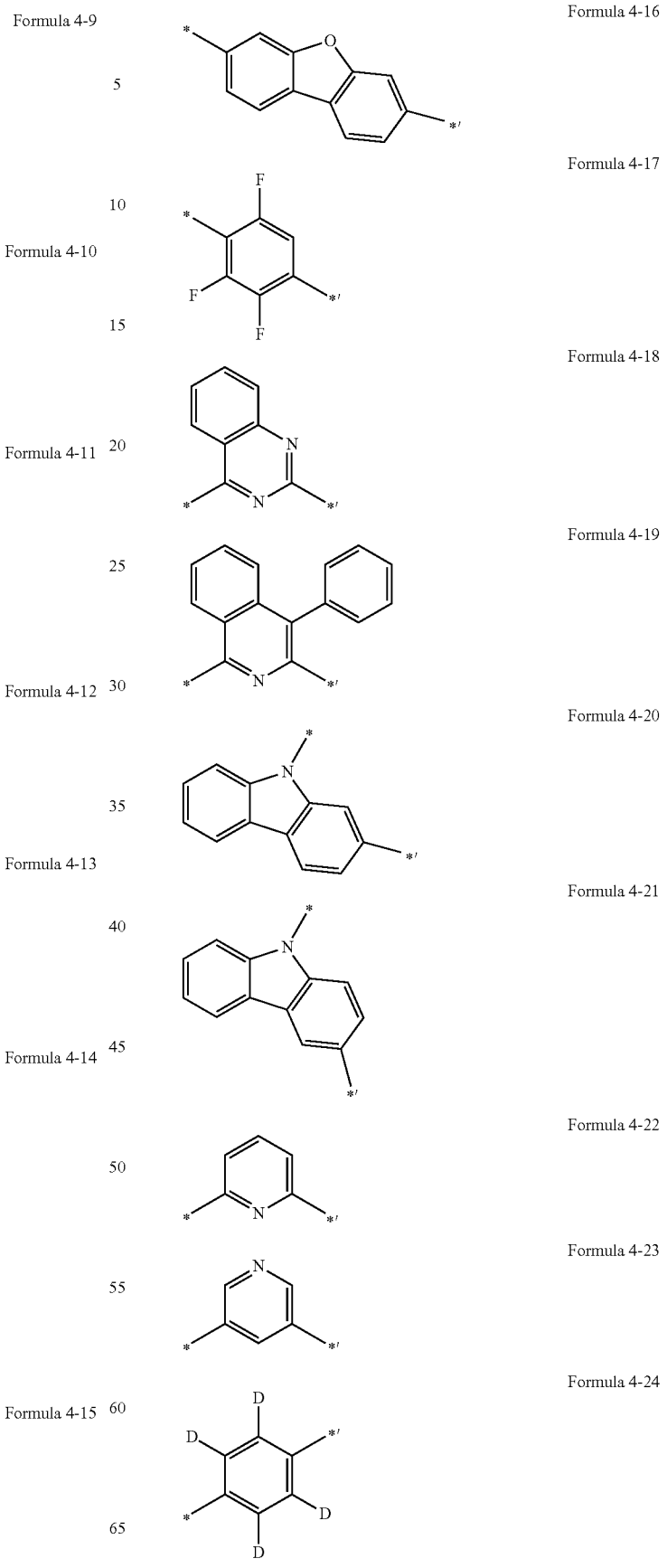
Formula 4-9
Formula 4-10
Formula 4-11
Formula 4-12
Formula 4-13
Formula 4-14
Formula 4-15
Formula 4-16
Formula 4-17
Formula 4-18
Formula 4-19
Formula 4-20
Formula 4-21
Formula 4-22
Formula 4-23
Formula 4-24

-continued

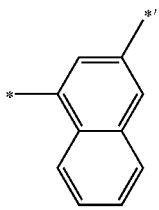

Formula 4-25

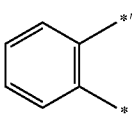

Formula 4-26

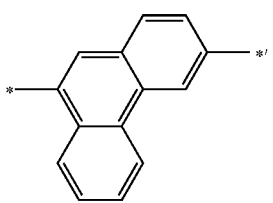

Formula 4-27

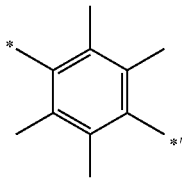

Formula 4-28

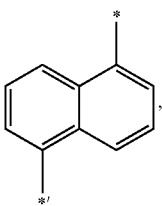

Formula 4-29 wherein, in Formulae 4-1 to 4-29, * and *' each indicate a binding site to a neighboring atom.

5. The organic light-emitting device of claim 1, wherein $L_1$ is selected from the group consisting of:
a phenylene group, a naphthylene group, a fluorenylene group, a phenanthrenylene group, an anthracenylene group, a triphenylenylene group, and a pyrenylene group, and
a phenylene group, a naphthylene group, a fluorenylene group, a phenanthrenylene group, an anthracenylene group, a triphenylenylene group, and a pyrenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, and a naphthyl group.

6. The organic light-emitting device of claim 1, wherein a1 is 0 or 1.

7. The organic light-emitting device of claim 1, wherein $R_1$ to $R_6$ and $R_8$ to $R_{10}$ are each independently selected from the group consisting of:
hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group,
a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, a dibenzosilolyl group, an imidazopyridinyl group, and an imidazopyrimidinyl group,
a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, a dibenzosilolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, a dibenzosilolyl group, an imidazopyridinyl group, an imidazopyrimidinyl group, and $-Si(Q_{31})(Q_{32})(Q_{33})$, and
$-Si(Q_1)(Q_2)(Q_3)$,
wherein $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group.

8. The organic light-emitting device of claim 1, wherein $R_1$ to $R_6$ and $R_8$ to $R_{10}$ are each independently selected from the group consisting of:
hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group,
a phenyl group, a biphenyl group, a terphenyl group, a naphthyl group, a pyridinyl group, a pyrimidinyl group, and a triazinyl group,
a phenyl group, a biphenyl group, a terphenyl group, a naphthyl group, a pyridinyl group, a pyrimidinyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a triazinyl group, and $-Si(Q_{31})(Q_{32})(Q_{33})$, and
$-Si(Q_1)(Q_2)(Q_3)$,
wherein $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group.

9. The organic light-emitting device of claim 1, wherein $R_{11}$ is selected from the group consisting of:
a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, a dibenzosilolyl group, an imidazopyridinyl group, and an imidazopyrimidinyl group, and
a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, a dibenzosilolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, a dibenzosilolyl group, an imidazopyridinyl group, and an imidazopyrimidinyl group, and $-Si(Q_{31})(Q_{32})(Q_{33})$.

10. The organic light-emitting device of claim 1, wherein the condensed cyclic compound is represented by one selected from Formulae 1-2(A) and 1-2(B):

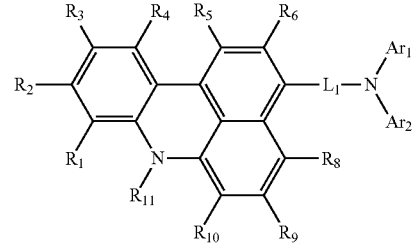

Formula 1-2(A)

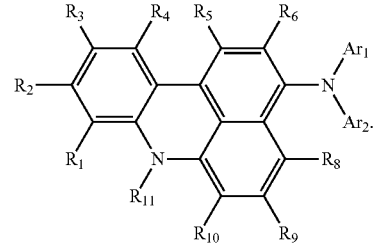

Formula 1-2(B)

11. The organic light-emitting device of claim 10, wherein $R_1$ to $R_6$ and $R_8$ to $R_{10}$ are each independently hydrogen;
$L_1$ is selected from a substituted or unsubstituted phenylene group, a substituted or unsubstituted naphthylene group, a substituted or unsubstituted fluorenylene group, a substituted or unsubstituted phenanthrenylene group, a substituted or unsubstituted anthracenylene group, a substituted or unsubstituted triphenylenylene group, and a substituted or unsubstituted pyrenylene group;

$R_{11}$ is selected from a substituted or unsubstituted phenyl group, a substituted or unsubstituted biphenyl group, a substituted or unsubstituted terphenyl group, a substituted or unsubstituted naphthyl group, a substituted or unsubstituted fluorenyl group, a substituted or unsubstituted phenanthrenyl group, a substituted or unsubstituted anthracenyl group, a substituted or unsubstituted triphenylenyl group, a substituted or unsubstituted pyrenyl group, a substituted or unsubstituted fluorenyl group, a substituted or unsubstituted spiro-bifluorenyl group, a substituted or unsubstituted carbazolyl group, a substituted or unsubstituted dibenzofuranyl group, a substituted or unsubstituted dibenzothiophenyl group, and a substituted or unsubstituted dibenzosilolyl group; and at least one substituent of the substituted phenylene group, substituted naphthylene group, substituted fluorenylene group, substituted phenanthrenylene group, substituted anthracenylene group, substituted triphenylenylene group, substituted pyrenylene group, substituted phenyl group, substituted biphenyl group, substituted terphenyl group, substituted naphthyl group, substituted fluorenyl group, substituted phenanthrenyl group, substituted anthracenyl group, substituted triphenylenyl group, substituted pyrenyl group, substituted fluorenyl group, substituted spiro-bifluorenyl group, substituted carbazolyl group, substituted dibenzofuranyl group, substituted dibenzothiophenyl group, and substituted dibenzosilolyl group is selected from the group consisting of:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{20}$ alkyl group, and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group, a phenyl group, a biphenyl group, a terphenyl group, a naphthyl group, a pyridinyl group, a fluorenyl group, spiro-bifluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, and a pyridinyl group, and —Si($Q_{31}$)($Q_{32}$)($Q_{33}$), wherein $Q_{31}$ to $Q_{33}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, spiro-bifluorenyl group, a benzofluorenyl group, a dibenzofluorenyl group, a phenanthrenyl group, an anthracenyl group, a pyrenyl group, a chrysenyl group, and a carbazolyl group.

12. An organic light-emitting device comprising:

a first electrode;

a second electrode facing the first electrode; and an organic layer between the first electrode and the second electrode, the organic layer comprising:

i) an emission layer, ii) a hole transport region between the first electrode and the emission layer, the hole transport region comprising at least one selected from a hole injection layer, a hole transport layer, a buffer layer, and an electron blocking layer, and iii) an electron transport region between the emission layer and the second electrode, the electron transport region comprising at least one selected from a hole blocking layer, an electron transport layer, and an electron injection layer, wherein the emission layer is to emit blue fluorescence, wherein the hole transport region comprises a condensed cyclic compound selected from Compounds 57, 66, 81, and 90:

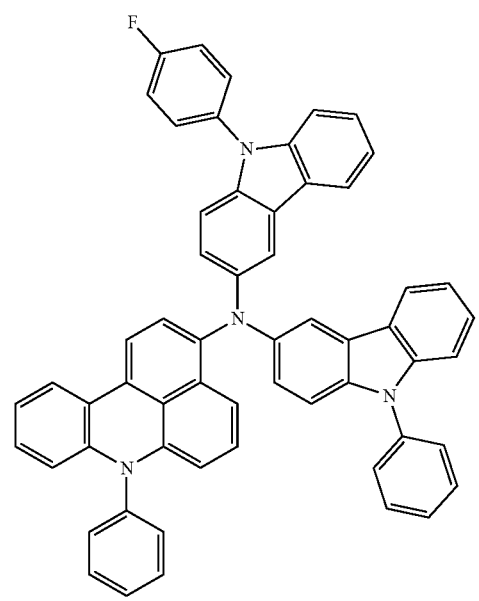
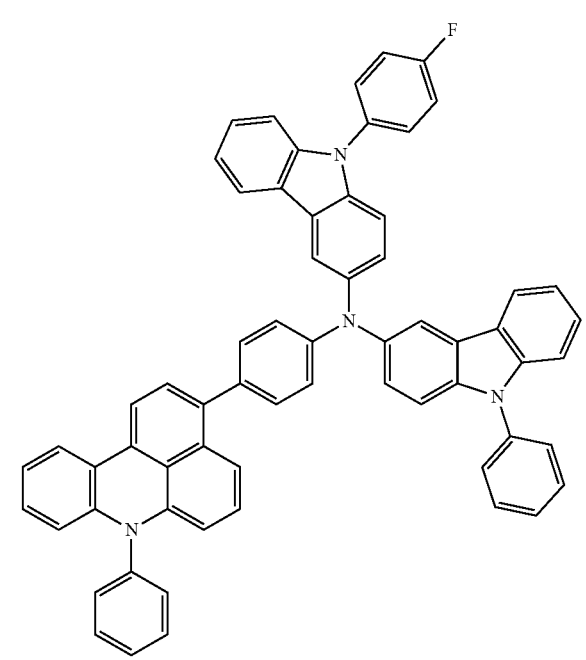
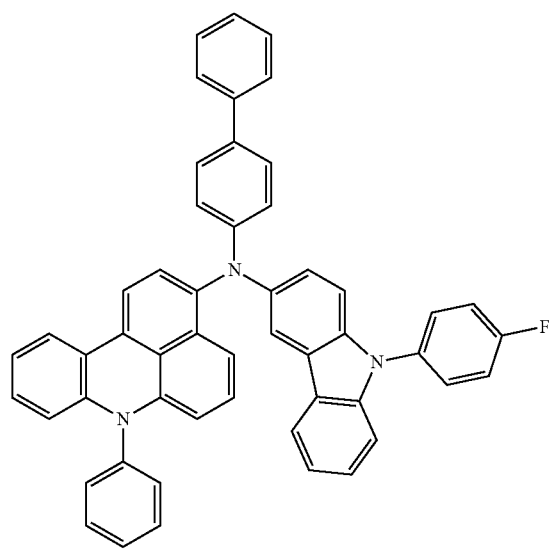
13. The organic light-emitting device of claim 1, wherein the hole transport region comprises a charge-generating material.
* * * * *